United States Patent [19]

Satow et al.

[11] Patent Number: 5,127,935

[45] Date of Patent: Jul. 7, 1992

[54] URACIL DERIVATIVES AND HERBICIDES CONTAINING THE SAME AS ACTIVE INGREDIENT

[75] Inventors: Jun Satow; Kenzou Fukuda; Kaoru Itoh, all of Funabashi; Koichi Suzuki, Urawa; Tsutomu Nawamaki, Yono; Shigeomi Watanabe, Omiya, all of Japan

[73] Assignee: Nissan Chemical Industries Ltd., Tokyo, Japan

[21] Appl. No.: 682,370

[22] Filed: Apr. 9, 1991

Related U.S. Application Data

[63] Continuation of Ser. No. 549,140, Jul. 6, 1990, abandoned.

[30] Foreign Application Priority Data

Jul. 14, 1989 [JP] Japan ................................ 1-181824
Jul. 19, 1989 [JP] Japan ................................ 1-187065
Oct. 20, 1989 [JP] Japan ................................ 1-274662
Jun. 27, 1990 [JP] Japan ................................ 1-168688

[51] Int. Cl.$^5$ .................... A01N 43/48; C07D 239/55
[52] U.S. Cl. ............................................ 71/92; 71/90;
544/309; 544/310; 544/311; 544/312; 544/313; 544/314
[58] Field of Search ............... 544/309, 310, 311, 313, 544/314, 312; 71/90, 92

[56] References Cited

U.S. PATENT DOCUMENTS

| 4,266,056 | 5/1981 | Henrick et al. | 544/311 |
| 4,338,318 | 7/1982 | Henrick et al. | 544/314 |
| 4,760,163 | 7/1988 | Wenger et al. | 71/92 |
| 4,812,164 | 3/1989 | Wenger et al. | 71/92 |
| 4,859,229 | 8/1989 | Wenger et al. | 71/92 |
| 4,941,909 | 7/1990 | Wenger et al. | 71/92 |
| 4,981,508 | 1/1991 | Strunk et al. | 71/92 |
| 5,017,211 | 5/1991 | Wenger et al. | 71/92 |
| 5,041,156 | 8/1991 | Wenger et al. | 71/92 |

FOREIGN PATENT DOCUMENTS 0255047 2/1988 European Pat. Off. .
0311135 4/1989 European Pat. Off. .
9015057 12/1990 World Int. Prop. O. .

Primary Examiner—Cecilia Shen
Attorney, Agent, or Firm—Oblon, Spivak, McClelland, Maier & Neustadt

[57] ABSTRACT

Disclosed herein is uracil derivatives having a haloalkyl group at the 5-position and a phenyl group at the 2-position which has a specific substituent, which are represented by the formula (I) and showing penetrative translocation activity and a very high herbicidal activity, in which as compared with the conventional herbicidal compounds, the said uracil derivatives can be applied for either soil treatment or foliage treatment, thereby producing a quick and high herbicidal effect even at a very low dosage against a large variety of weeds including perennial weeds, and have the property to residual effect for an appropriate period of time.

9 Claims, No Drawings

URACIL DERIVATIVES AND HERBICIDES CONTAINING THE SAME AS ACTIVE INGREDIENT

This is a continuation of application Ser. No. 07/549,140, filed on Jul. 6, 1990, abandoned.

BACKGROUND OF THE INVENTION

The present invention relates to novel uracil derivatives and herbicides having an selectivity and containing the uracil derivatives as active ingredients.

A large variety of herbicides have been prepared and practically used for protecting important crop plants such as rice, soybean, wheat, corn, cotton, beet, etc., from weeds and for enhancing productivity of these crop plant. The herbicides may be roughly classified into the following three types according to the locality of application: ① herbicides for upland cropping, ② herbicides for paddy field and ③ herbicides for non-arable land. Each kind of herbicides can be further classified into subclasses such as soil incorporation treatment type, pre-emergence treatment type and post-emergence treatment type (foliage treatment) according to the method of application.

With increase of global population in recent years, there is no denying the fact that productivity of principal crop plants gives a serious influence to food economy of each country, and thus enhancement of productivity of principal crop plants is now a matter of paramount importance. In fact, for the people engaged in farming, it is still more necessary to develop herbicides which are capable of economical and efficient killing or controlling of growth of weeds which do harm to cultivation of crop plants.

As such herbicides, there are demanded the ones which can meet the following requirements:

(1) Herbicidal effect is high with small amount of application. (It is necessary, especially from the viewpoint of environmental protection, to kill the weeds by application of as small as amount of herbicide as possible.)

(2) Residual effect is appropriate. (Recently, the problem is pointed out that the chemicals retaining their effect in soil for a long time could give damage to the next crop plants. It is thus important that the chemicals keep an appropriate residual effect after application).

(3) Weeds are killed quickly after application. (It is made possible to perform seeding and transplantation of the next crop plant in a short time after chemicals treatment.)

(4) The number of times of herbicide treatment (application) required is small. (It is of much account for the farmers that the number of times of weed-controlling work be minimized.)

(5) Weeds killed or controlled by one of herbicide is of wide range. (It is desirable that different weeds such as broad-leaved weeds, graminaceous weeds and perennial weeds can be killed or controlled by application of one of herbicide.)

(6) The application method is diversified. (The herbicidal effect is intensified when it can be applied in various ways, such as soil treatment, foliage treatment, etc.)

(7) No damage to crop plants is given. (In a cultivated field where both crop plants and weeds co-exist, it is desirable that weeds alone are killed selectively by a herbicide.)

Nevertheless, there is yet available no herbicide which can meet all of the above requirements.

It is known that certain compounds of uracil derivatives have a herbicidal activity. For instance, in the Pesticide Manual, 8th Ed., p. 89 (published by The British Crop Protection Council, 1987), Bromacil as one the herbicides having uracil skeleton is disclosed.

There are also known the following hetero-ring derivatives which can serve as active ingredient for herbicides:

(1) 3-Aryluracil-alkyl, alkenyl and alkinylenol ethers represented by the following general formula:

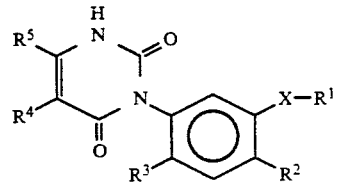

wherein
$R^1$ represents $C_{1-8}$ alkyl, $C_{2-6}$ alkenyl, $C_{2-6}$ alkynyl, $C_{2-8}$ alkoxyalkyl or

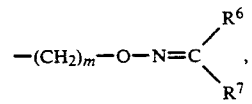

$R^2$ represents halogen or cyano, $R^3$ represents hydrogen or halogen, $R^4$ represents hydrogen, fluorine or $C_{1-4}$ alkyl, $R^5$ represents $C_{1-4}$ alkyl or $C_{1-4}$ haloalkyl, or $R^4$ and $R^5$ may combine to represent tri- or tetra-methylene (in which $R^6$ and $R^7$ represent independently $C_{1-4}$ alkyl, and m is 1 or 2), and X is O, O—C(O), O—C(O)—O or C(O)—O (Japanese Patent Application Laid-Open (Kokai) No. 63-107967).

(2) Compounds represented by the following general formula:

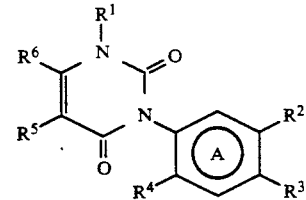

wherein
$R^1$ represents hydrogen, $C_{1-4}$ alkyl, $C_{1-4}$ haloalkyl, formyl or $C_{2-6}$ alkanonyl, $R^2$ represents ether or a residue containing (thio)carbonyloxy or sulfonyloxy, the residue being directly linked to benzene nucleus A through oxygen atom, $R^3$ represents halogen or cyano, $R^4$ represents hydrogen or halogen, $R^5$ represents hydrogen, halogen or $C_{1-4}$ alkyl, and $R^6$ represents $C_{1-4}$ alkyl or $C_{1-4}$ haloalkyl, or $R^5$ and $R^6$ may be combined together to represent tri- or tetrametylene, and salts of the compounds of the said formula wherein $R^1$ is hydrogen (Japanese Patent Application Laid-Open (Kokai) No. 63-41466).

(3) Benzothiazolone derivatives represented by the general formula:

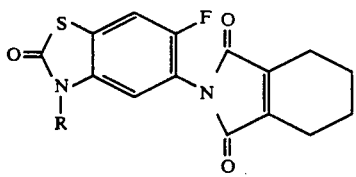

wherein R represents hydrogen, lower alkyl, lower alkenyl, lower alkynyl, lower haloalkyl, lower haloalkenyl, lower haloalkynyl, lower alkoxy-lower alkyl, lower alkoxy-lower alkoxy-lower alkyl, cinnamyl or lower cyanoalkyl (Japanese Patent Application Laid-Open (Kokai) No. 62-155276).

(4) Condensed hetero-ring derivatives represented by the general formula:

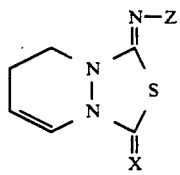

wherein X represents oxygen atom or sulfur atom, and Z represents

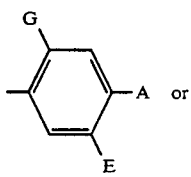 (Z1)

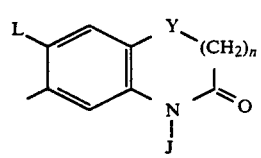 (Z2)

in which G represents hydrogen atom or halogen atom, A represents halogen atom or $NO_2$, E represents hydrogen atom, halogen atom, $C \equiv N$, $NO_2$, $NH_2$, OH, SH, $OR_1$ [wherein $R_1$ represents $C_{1-5}$ alkyl, $C_{3-6}$ cycloalkyl, $C_{3-6}$ cycloalkyl-$(C_{1-2})$ alkyl, $C_{2-4}$ alkenyl, $C_{3-4}$ alkynyl,

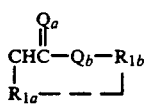

in which $Q_a$ and $Q_b$ represent independently oxygen atom or sulfur atom, $R_{1a}$ represents hydrogen atom or $C_{1-3}$ alkyl, and $R_{1b}$ represents hydrogen atom, $C_{1-5}$ alkyl, $C_{2-5}$ alkenyl, $C_{3-5}$ alkynyl, $C_{2-3}$ haloalkyl, $C_{1-2}$ alkoxy $(C_{1-2})$ alkyl, $C_{3-4}$ cycloalkyl-$(C_{1-2})$ alkyl, $C_{3-6}$ cycloalkyl, $CH_2CO_2$—$(C_{1-3}$ alkyl), or $CH(CH_3)$—$CO_2$—$(C_{1-2}$ alkyl), or $R_{1a}$ and $R_{1b}$ are combined to form a 4- to 6-membered ring lactone constituted by methylene chain),

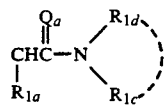

(in which $R_{1a}$ and $Q_a$ are the same meaning as defined above, and $R_{1c}$ and $R_{1d}$ represent independently hydrogen atom, $C_{1-5}$ alkyl, $C_{2-5}$ alkenyl, $C_{3-5}$ alkynyl, $C_{2-5}$ haloalkyl, $C_{3-6}$ cycloalkyl or $C_{3-6}$ cycloalkyl-$(C_{1-2})$ alkyl, or $R_{1d}$ and $R_{1c}$ are combined to form a 5- to 7-membered ring constituted by methylene chain), $CH_2C \equiv N$, tetrahydropyranyl, tetrahydrothiopyranyl, $CH_2COR_{1e}$,

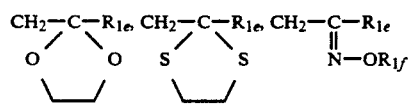

(in which $R_{1e}$ represents $C_{1-3}$ alkyl, $R_{1f}$ represents hydrogen atom, $C_{1-3}$ alkyl, $CH_2CO_2$—$(C_{1-3})$ alkyl or $COCH_3$), or $C_{1-2}$ alkoxy-$(C_{1-2})$ alkyl], $SR_3$ (in which $R_3$ is the same meaning as $R_1$ described above), $CO_2R_5$ (in which $R_5$ represents hydrogen atom, $C_{1-5}$ alkyl, $C_{3-6}$ cycloalkyl or $C_{3-6}$ cycloalkyl-$(C_{1-2})$ alkyl), $NHR_6$ (in which $R_6$ represents $C_{1-5}$ alkyl, $C_{3-6}$ cycloalkyl, $C_{3-6}$ cycloalkyl-$(C_{1-2})$ alkyl, $C_{2-4}$ alkenyl or $C_{3-4}$ alkynyl), or $CH|NOR_7$ (in which $R_7$ is hydrogen atom, $C_{1-5}$ alkyl, $C_{3-6}$ cycloalkyl, $C_{3-6}$ cycloalkyl- alkyl, $C_{2-4}$ alkenyl or $C_{3-4}$ alkynyl), L represents hydrogen atom or halogen atom, Y represents oxygen atom or sulfur atom, n is 0 or 1, and J represents hydrogen atom, halogen atom, $C_{1-5}$ alkyl, $C_{3-6}$ cycloalkyl, $C_{3-6}$ cycloalkyl-$(C_{1-2})$ alkyl, $C_{2-4}$ alkenyl, $C_{3-4}$ alkynyl, $C_{1-5}$ haloalkyl, $C_{3-4}$ haloalkenyl, $C_{3-4}$ haloalkynyl, $C_{1-2}$ alkoxy-$(C_{1-2})$ alkyl, $CH_2C \equiv N$, $CH_2CO_2R_8$ (in which $R_8$ is hydrogen atom, $C_{1-5}$ alkyl, $C_{3-6}$ cycloalkyl or $C_{3-6}$ cycloalkyl-$(C_{1-2})$ alkyl), or $CH_2CH_2CO_2R_9$ (in which $R_9$ is hydrogen atom, $C_{1-5}$ alkyl, $C_{3-6}$ cycloalkyl or $C_{3-6}$ cycloalkyl-$(C_{1-2})$ alkyl) (Japanese Patent Application Laid-Open (Kokai) No. 1-250388).

(5) Compounds represented by the following formula:

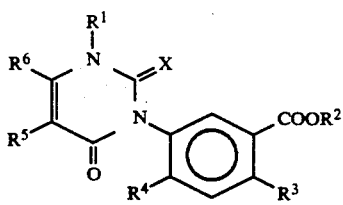

wherein $R^1$ represents hydrogen, $C_{1-4}$ alkyl, $C_{2-4}$ alkenyl, $C_{2-4}$ alkynyl, $C_{2-6}$ alkoxyalkyl, formyl, $C_{2-6}$ alkanoyl or $C_{2-6}$ alkoxycarbonyl; $R^2$ represents hydrogen, $C_{1-6}$ alkyl, $C_{2-4}$ alkenyl, $C_{2-4}$ alkynyl or $C_{2-6}$ alkoxyalkyl; $R^3$ represents halogen or nitro; $R^4$ represents hydrogen or halogen; $R^5$ represents hydrogen, halogen, $C_{1-4}$ alkyl, chloromethyl, bromomethyl, hydroxymethyl, $(C_{1-5}$ alkoxy)-methyl, $(C_{1-5}$ alkylthio)methyl, cyano, nitro or thiocyanato; $R^6$ represents hydrogen, $C_{1-4}$ alkyl or $C_{1-4}$ fluoroalkyl, or $R^5$ and $R^6$ are combined to represent tri- or tetramethylene, in which one of the said methylene groups may be substituted with oxygen or sulfur, or these groups may be substituted with $C_{1-3}$ alkyl; and X represents oxygen or sulfur, in which (i) when $R^5$ is fluorine, $R^6$ is $C_{1-4}$ alkyl or $C_{1-4}$ fluoroalkyl, and (ii) when $R^5$ is cyano, $R^6$ is hydrogen or $C_{1-4}$ alkyl, and X is oxygen, and salts of the compounds of the said formula wherein $R^1$ and/or $R^2$ represent(s) hydrogen (Japanese Patent Application Laid-Open (Kokai) No. 61-221178).

(6) Tetrahydrophthalimide derivatives represented by the following formula:

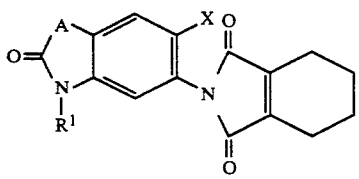

wherein $R^1$ represents $C_{1-5}$ alkyl, $C_{3-5}$ alkenyl, $C_{3-5}$ alkynyl or $C_{1-3}$ alkoxymethyl, X is hydrogen, fluorine or chlorine, and A represents

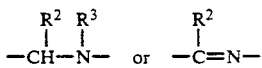

in which $R^2$ represents hydrogen or methyl, $R^3$ represents hydrogen or methyl, and nitrogen atom is bonded to benzene ring (Japanese Patent Application Laid-Open (Kokai) No. 61-85385).

(7) Tetrahydrophthalimide derivatives represented by the following formula:

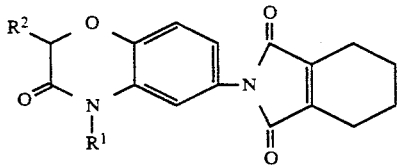

wherein $R^1$ represents alkyl, alkenyl, alkynyl, alkoxyalkyl or alkoxyalkoxyalkyl, and $R^2$ represents hydrogen or methyl (Japanese Patent Application Laid-Open (Kokai) No. 61-30586).

(8) Tetrahydrophthalimide derivatives represented by the following formula:

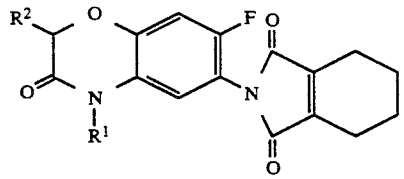

wherein $R^1$ represents alkyl, alkenyl, alkynyl, alkoxyalkyl or alkoxyalkoxyalkyl, and $R^2$ represents hydrogen or methyl (Japanese Patent Application Laid-Open (Kokai) No. 61-76486).

(9) Tetrahydrophthalimide derivatives represented by the following formula:

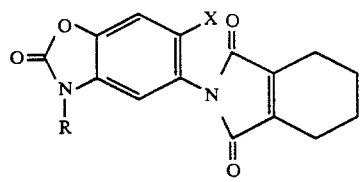

wherein R represents $C_{1-5}$ alkyl, $C_{3-5}$ alkenyl, $C_{3-5}$ alkynyl or $C_{1-3}$ alkoxymethyl, and X represents hydrogen or fluorine (Japanese Patent Application Laid-Open (Kokai) No. 61-43188).

(10) Herbicidal compounds having the general formula:

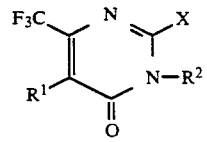

wherein X is hydrogen or hydroxy, $R^1$ is hydrogen or halo and $R^2$ is alkyl, cycloalkyl, phenyl, alkenyl, and substituted derivatives of the above (U.S. Pat. No. 3,981,715).

(11) Herbicidal compounds having the general formula:

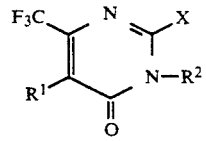

wherein X is hydrogen or hydroxy, $R^1$ is hydrogen or halo and $R^2$ is alkyl, cycloalkyl, phenyl, alkenyl, and substituted derivatives of the above (U.S. Pat. No. 3,869,457).

(12) Compounds of formula (I):

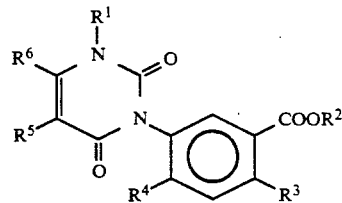

wherein $R^1$ represents hydrogen, $C_{1-4}$ alkyl, $C_{3-4}$ alkenyl, $C_{3-4}$ alkynyl or $C_{1-4}$ haloalkyl, $R^2$ represents

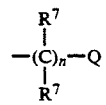

or, when $R^1$ represents haloalkyl, hydrogen, $C_{1-8}$ alkyl, $C_{2-8}$ alkenyl, $C_{2-8}$ alkynyl or $C_{2-8}$ alkoxyalkyl, $R^3$ represents halogen or cyano, $R^4$ represents hydrogen or halogen and $R^5$ represents hydrogen, fluorine or $C_{1-4}$ haloalkyl, as well as their enol ethers and salts (WO 88/10254).

Keen request is heard for the presentation of a herbicide which can meet the above-mentioned requirements (1)-(7), namely a herbicide which shows selectivity in potency, with no fear of giving any damage to crop plants (crop injury), exhibits excellent herbicidal effect at low dosage against a vide variety of weeds, and is also capable of exhibiting desired effect in both soil treatment and foliage treatment.

As a result of the present inventors, extensive studies, it has been found that the uracil derivatives having a haloalkyl group at the 5-position and a phenyl group at the 2-position which has a specific substituent, which are represented by the following formula (I) have penetrative translocation activity and a very high herbicidal activity, and as compared with the conventional herbicidal compounds, the said uracil derivatives can be applied for either soil treatment or foliage treatment, thereby producing a quick and high herbicidal effect even at a very low dosage against a large variety of weeds including perennial weeds, and have the property to residual effect for an appropriate period of time. The present invention was attained on the basis of the said finding.

SUMMARY OF THE INVENTION

In a first aspect of the present invention, there are provided uracil derivatives represented by the formula (I):

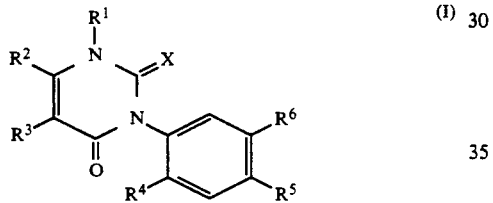

wherein
$R^1$ represents hydrogen, $C_{1-3}$ alkyl, hydroxymethyl or $C_{1-3}$ haloalkyl,
$R^2$ represents $C_{1-6}$ haloalkyl,
$R^3$ represents hydrogen, $C_{1-6}$ alkyl, $C_{1-6}$ haloalkyl, hydroxymethyl, halogen or nitro,
$R^4$ represents hydrogen or halogen,
(i) when $R^5$ and $R^6$ are taken separately,
$R^5$ represents halogen, nitro or cyano,
$R^6$ represents $-S-B^1$ [wherein $B^1$ represents hydrogen, $C_{1-5}$ alkyl, $C_{3-6}$ cycloalkyl, $C_{2-4}$ alkenyl, $C_{3-4}$ alkynyl, cyanomethyl, hydroxymethyl, chloromethyl, benzyl,

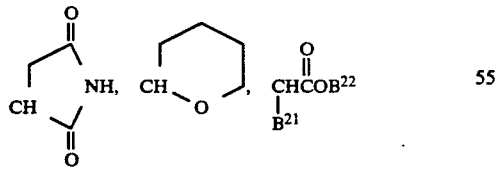

in which $B^{21}$ represents hydrogen, $C_{1-3}$ alkyl, methylthio, phenylthio or methoxymethyl, and $B^{22}$ represents hydrogen, sodium, potassium, ammonium, isopropylammonium, $C_{1-5}$ alkyl, $C_{2-5}$ alkenyl, $C_{3-5}$ alkynyl, $C_{3-6}$ cycloalkyl, $C_{3-6}$ cycloalkyl-$C_{1-2}$ alkyl, $C_{2-3}$ haloalkyl, phenethyl, α-methylbenzyl, 3-dimethylaminopropyl, phenyl which may be substituted with one or more substituent (the substituent is at least one of halogen, $C_{1-4}$ alkyl, $C_{1-3}$ alkoxyl, $C_{1-2}$ alkylamino, dimethylamino, $C_{1-2}$ alkoxy-carbonyl, $C_{2-3}$ acyl, $C_{1-2}$ haloalkyl or $C_{1-2}$ haloalkyloxyl), or benzyl which may be substituted with one or more substituent (the substituent(s) is at least one of halogen, $C_{1-4}$ alkyl, $C_{1-3}$ alkoxyl, $C_{1-2}$ alkylamino, dimethylamino, $C_{2-3}$ acyl, trifluoroacetylamino, $C_{1-2}$ alkoxy-carbonyl, methylsulfonyl, trifluoromethylsulfonyl, $C_{1-2}$ haloalkyl or $C_{1-2}$ haloalkyloxyl)], $CH_2$-$(CH_2)_n$-$CO_2B^{22}$ [wherein $B^{22}$ is the same meaning as defined above, and n is an integer of 1 to 4), $CH_2$—Y—$B^{23}$ (wherein $B^{23}$ is hydrogen, $C_{1-5}$ alkyl, cyanomethyl, $C_{2-5}$ acyl, chloroacetyl or dimethylcarbamoyl, and Y is oxygen or sulfur, $CH_2$—Y—$CH(B^{21})CO_2B^{22}$ (wherein $B^{21}$, $B^{22}$ and Y are the same meanings as defined above), or $CH_2$—Y—$(CH_2CH_2)_n$-$CO_2B^{22}$ (wherein $B^{22}$, n and Y are the same meanings as defined above)];

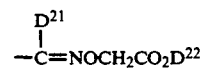

[wherein $D^{21}$ represents hydrogen, $C_{1-3}$ alkyl, $C_{1-3}$ alkoxyl or $C_{1-3}$ alkoxy-$C_{1-2}$ alkyl, and $D^{22}$ represents hydrogen, $C_{1-4}$ alkyl, $C_{3-6}$ cycloalkyl, $C_{2-3}$ haloalkyl, phenyl or benzyl];

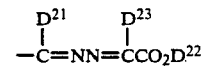

[wherein $D^{21}$ and $D^{22}$ are the same meanings as above, and $D^{23}$ represents hydrogen or $C_{1-3}$ alkyl];

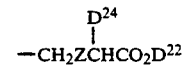

[wherein $D^{22}$ is the same meaning as defined above, $D^{24}$ represents hydrogen, $C_{1-3}$ alkyl or $C_{1-3}$ alkoxy-$C_{1-2}$ alkyl, and Z represents oxygen, sulfur or NH];

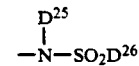

[wherein $D^{25}$ represents hydrogen, sodium, $C_{1-4}$ alkyl, $C_{2-5}$ alkenyl, $C_{3-5}$ alkynyl, $C_{2-5}$ acyl, $C_{1-4}$ alkylsulfonyl or $C_{1-3}$ alkoxy-$C_{1-2}$ alkyl, and $D^{26}$ represents $C_{1-4}$ alkyl or $C_{1-3}$ haloalkyl];

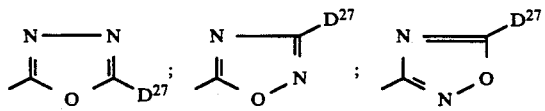

[wherein $D^{27}$ represents hydrogen, $C_{1-6}$ alkyl, $C_{3-6}$ cycloalkyl, $C_{1-3}$ haloalkyl, $C_{1-4}$ alkoxyl, $C_{1-4}$ alkylthio, $C_{1-4}$ alkoxy-carbonyl, mercapto, hydroxyl, $C_{1-3}$ alkoxy-$C_{1-2}$ alkyl, $C_{1-4}$ alkylamino, $ND^{28}(D^{29})$ (wherein $D^{28}$ and $D^{29}$ represent independently $C_{1-4}$ alkyl), dimethylcarbamoyl, $CONHSO_2CH_3$, $C_{1-4}$ alkylsulfonyl, or $N(D^{30})SO_2D^{31}$ (wherein $D^{30}$ represents hydrogen, sodium, $C_{1-4}$ alkyl, $C_{1-4}$ alkylsulfonyl, $C_{1-3}$ alkoxy-$C_{1-2}$ alkyl, and $D^{31}$ represents $C_{1-4}$ alkyl or $C_{1-3}$ haloalkyl)];

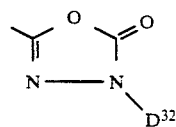

[wherein $D^{32}$ represents $C_{1-6}$ alkyl or $C_{3-6}$ cycloalkyl];

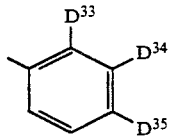

[wherein $D^{33}$, $D^{34}$ and $D^{35}$ represent independently hydrogen or $C_{1-6}$ alkyl];

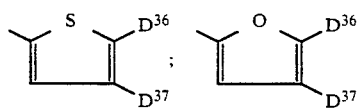

[wherein $D^{36}$ and $D^{37}$ represent independently hydrogen, $C_{1-6}$ alkyl or dimethylamino];

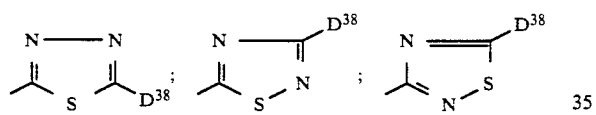

[wherein $D^{38}$ represents hydrogen, halogen, mercapto, hydroxyl, $C_{1-6}$ alkyl, $C_{3-6}$ cycloalkyl, $C_{1-3}$ haloalkyl, $C_{1-4}$ alkoxyl, $C_{1-4}$ alkylthio, $C_{1-4}$ alkoxycarbonyl, dimethylcarbamoyl, $C_{1-3}$ alkoxy-$C_{1-2}$ alkyl, $C_{1-4}$ alkylamino, $ND^{28}(D^{29})$ (wherein $D^{28}$ and $D^{29}$ are the same meanings as defined above), $CONHSO_2CH_3$, $C_{1-4}$ alkylsulfonyl, phenyl, benzyl or $N(D^{39})SO_2D^{31}$ (wherein $D^{31}$ is the same meaning as defined above, and $D^{39}$ represents hydrogen, $C_{1-4}$ alkyl, sodium, potassium, $C_{1-4}$ alkylsulfonyl or $C_{1-3}$ alkoxy-$C_{1-2}$ alkyl)];

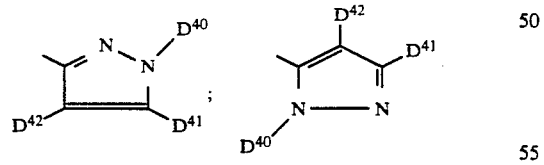

[wherein $D^{40}$ represents hydrogen, $C_{1-6}$ alkyl, $C_{3-6}$ cycloalkyl, phenyl, benzyl or 2-pyridyl, $D^{41}$ represents hydrogen, halogen, mercapto, hydroxyl, amino, $C_{1-6}$ alkyl, $C_{1-4}$ alkylamino, $ND^{28}(D^{29})$ (wherein -$D^{28}$ and $D^{29}$ are the same meanings as defined above), $C_{1-4}$ alkylthio, $CO_2D^{28}$ (wherein $D^{28}$ is the same meaning as defined above), $C_{1-4}$ alkylsulfonyl, $C_{1-4}$ alkoxyl or $N(D^{39})SO_2D^{31}$ (wherein $D^{31}$ and $D^{39}$ are the same meanings as defined above), and $D^{42}$ represents hydrogen, halogen, nitro, amino, cyano, $C_{1-4}$ alkylamino, $N(D^{28})D^{29}$ (wherein $D^{28}$ and $D^{29}$ are the same meanings as defined above), $C_{1-4}$ alkylcarbonyl or $C_{1-4}$ alkoxy-carbonyl];

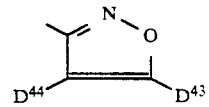

[wherein $D^{43}$ represents hydrogen, hydroxyl, methoxy, amino, benzoyl or $C_{1-4}$ alkyl, and $D^{44}$ represents hydrogen, cyano, acetyl, $C_{1-4}$ alkyl, carboxyl or $C_{1-4}$ alkoxy-carbonyl];

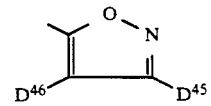

[wherein $D^{45}$ and $D^{46}$ represent independently hydrogen, phenyl, hydroxyl, methoxy or $C_{1-4}$ alkyl]; or

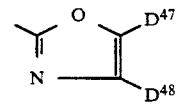

[wherein $D^{47}$ and $D^{48}$ represent independently hydrogen or $C_{1-4}$ alkyl], and X represents oxygen or sulfur, (ii) when $R^5$ and $R^6$ form a ring, the said urasil derivatives are represented by either of the following formula (II), (IV-1), (IV-2), (IV-3) or (IV-4):

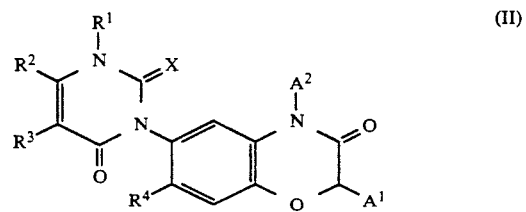

(II)

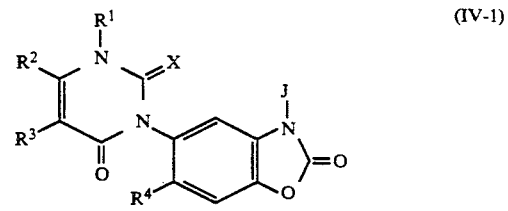

(IV-1)

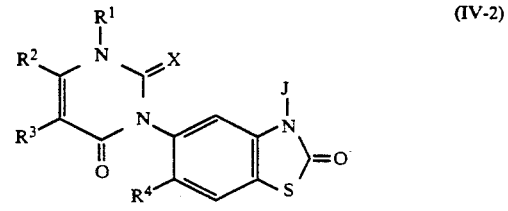

(IV-2)

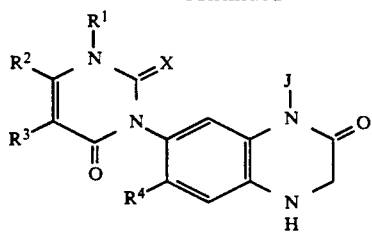
(IV-3)

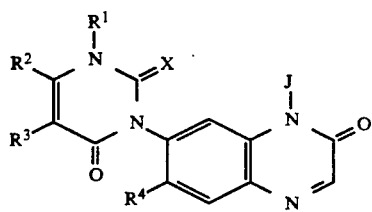
(IV-4)

wherein
R$^1$, R$^2$, R$^3$, R$^4$ and X are the same meanings as defined above, A$^1$ represents hydrogen and C$_{1-4}$ alkyl, A$^2$ represents hydrogen, C$_{1-5}$ alkyl, C$_{2-5}$ alkenyl, C$_{3-5}$ alkynyl, C$_{3-6}$ cycloalkyl-C$_{1-2}$ alkyl, C$_{1-6}$ haloalkyl, C$_{1-6}$ haloalkenyl, C$_{1-6}$ haloalkynyl, cyanomethyl, hydroxymethyl, chloromethyl, C$_{1-3}$ alkoxy-C$_{1-2}$ alkyl, —CH$_2$CO$_2$A$^{21}$ [wherein A$^{21}$ represents hydrogen, C$_{1-5}$ alkyl, sodium, phenyl which may be substituted with halogen, or benzyl which may be substituted with halogen], —CH$_2$CON(A$^{22}$)A$^{23}$ [wherein A$^{22}$ and A$^{23}$ represent independently hydrogen or C$_{1-3}$ alkyl], phenyl which may be substituted (the substituent is C$_{1-4}$ alkyl, C$_{1-4}$ haloalkyl, C$_{1-4}$ alkoxy or halogen), benzyl which may be substituted (the substituent is C$_{1-4}$ alkyl, C$_{1-4}$ haloalkyl, C$_{1-4}$ alkoxy, C$_{1-4}$ alkoxy-carbonyl, C$_{1-3}$ alkoxy-C$_{1-2}$ alkyl or halogen), or —CH$_2$A$^{24}$ [wherein A$^{24}$ represents 2-pyridyl which may be substituted (the substituent is C$_{1-4}$ alkyl or halogen), 2-pyridazyl which may be substituted (the substituent is C$_{1-4}$ alkyl or halogen), 3-isothiazole or 3-isoxazole], and J represents hydrogen, C$_{1-4}$ alkyl, C$_{2-4}$ alkenyl, C$_{3-4}$ alkynyl, hydroxymethyl, chloromethyl, carbamoylmethyl, cyanomethyl, C$_{1-4}$ alkoxy-carbonylmethyl,

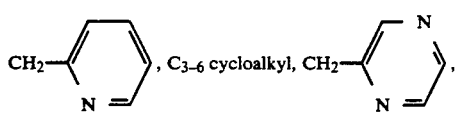

C$_{3-6}$ cycloalkyl-C$_{1-2}$ alkyl, C$_{1-2}$ alkoxy-C$_{1-2}$ alkyl, phenyl which may be substituted (the substituent is C$_{1-4}$ alkyl, C$_{1-4}$ alkoxy, C$_{1-4}$ alkoxy-carbonyl, C$_{1-4}$ alkoxy-C$_{1-2}$ alkyl or halogen), or benzyl which may be substituted (the substituent is C$_{1-4}$ alkyl, C$_{1-4}$ alkoxyl, C$_{1-4}$ alkoxy- carbonyl, C$_{1-4}$ alkoxy-C$_{1-2}$ alkyl or halogen).

In a second aspect of the present invention, there is provided a herbicidal composition comprising a herbicidally effective amount of an uracil derivative as defined in the first aspect and a herbicidally acceptable carrier or diluent therefor.

In a third aspect of the present invention, there is provided a method for killing weeds or inhibiting growth of weeds comprising applying a herbicidally effective amount of an uracil derivative as defined in the first aspect.

DETAILED DESCRIPTION OF THE INVENTION

The uracil derivatives represented by the formula (I) shown above according to the present invention are novel.

Among the uracil derivatives represented by the formula (I), those of the formulae (II), (III) and (IV) are preferred for the object of the invention. Namely, uracil derivatives represented by the formula (I) are set forth below:

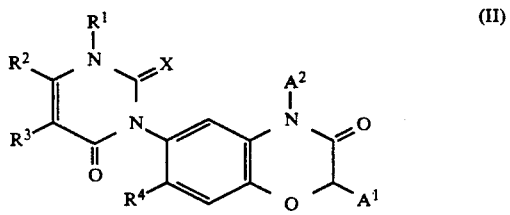
(II)

wherein
R$^1$ represents hydrogen, C$_{1-3}$ alkyl, hydroxymethyl or halomethyl, R$^2$ represents C$_{1-6}$ haloalkyl, R$^3$ represents hydrogen, C$_{1-6}$ alkyl, C$_{1-6}$ haloalkyl, hydroxymethyl, halogen or nitro, R$^4$ represents hydrogen or halogen, A$^1$ represents hydrogen or C$_{1-4}$ alkyl, A$^2$ represents hydrogen, C$_{1-5}$ alkyl, C$_{2-5}$ alkenyl, C$_{3-5}$ alkynyl, C$_{3-6}$ cycloalkyl-C$_{1-2}$ alkyl, C$_{1-6}$ haloalkyl, C$_{1-6}$ haloalkenyl, C$_{1-6}$ haloalkynyl, cyanomethyl, hydroxymethyl, chloromethyl, C$_{1-3}$ alkoxy-C$_{1-2}$ alkyl, —CH$_2$CO$_2$A$^{21}$ [wherein A$^{21}$ represents hydrogen, C$_{1-5}$ alkyl, sodium, phenyl which may be substituted with halogen, or benzyl which may be substituted with halogen], —CH$_2$CON(A$^{22}$)A$^{23}$ [wherein A$^{22}$ and A23 represent independently hydrogen or C$_{1-3}$ alkyl], phenyl which may be substituted (the substituent is C$_{1-4}$ alkyl, C$_{1-4}$ haloalkyl, C$_{1-4}$ alkoxyl or halogen), benzyl which may be substituted (the substituent is C$_{1-4}$ alkyl, C$_{1-4}$ haloalkyl, C$_{1-4}$ alkoxyl, C$_{1-4}$ alkoxy-carbonyl, C$_{1-3}$ alkoxy-C$_{1-2}$ alkyl or halogen), or —CH$_2$A$^{24}$ [wherein A$^{24}$ represents 2-pyridyl which may be substituted (the substituent is C$_{1-4}$ alkyl or halogen), 2-pyridazyl which may be substituted (the substituent is C$_{1-4}$ alkyl or halogen), 3-isothiazole or 3-isoxazole], and X represents oxygen or sulfur.

The uracil derivatives represented by the formula (III) are set forth below:

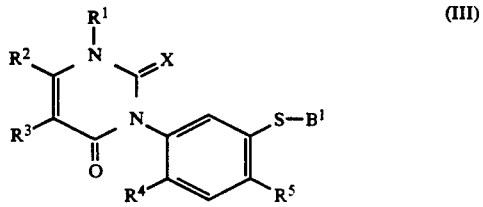
(III)

wherein
R¹ represents hydrogen, $C_{1-3}$ alkyl, hydroxymethyl or halomethyl,
R² represents $C_{1-6}$ haloalkyl,
R³ represents hydrogen, $C_{1-6}$ alkyl, $C_{1-6}$ haloalkyl, hydroxymethyl, halogen or nitro,
R⁴ represents hydrogen or halogen,
R⁵ represents halogen, nitro or cyano,
B¹ represents hydrogen, $C_{1-5}$ alkyl, $C_{3-6}$ cycloalkyl, $C_{2-4}$ alkenyl, $C_{3-4}$ alkynyl, cyanomethyl, hydroxymethyl, chloromethyl, benzyl,

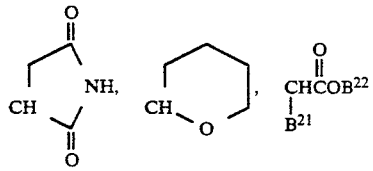

[wherein B²¹ represents hydrogen, $C_{1-3}$ alkyl, methylthio, phenylthio or methoxymethyl, and B²² represents hydrogen, sodium, potassium, ammonium, isopropylammonium, $C_{1-5}$ alkyl, $C_{2-5}$ alkenyl, $C_{3-5}$ alkynyl, $C_{3-6}$ cycloalkyl, $C_{3-6}$ cycloalkyl-$C_{1-2}$ alkyl, $C_{2-3}$ haloalkyl, phenethyl, α-methylbenzyl, 3-dimethylaminopropyl, phenyl which may be substituted with one or more substituent (the substituent is at least one of halogen, $C_{1-4}$ alkyl, $C_{1-3}$ alkoxyl, $C_{1-2}$ alkylamino, dimethylamino, $C_{1-2}$ alkoxy-carbonyl, $C_{2-3}$ acyl, $C_{1-2}$ haloalkyl or $C_{1-2}$ haloalkyloxyl), or benzyl which may be substituted with one or more substituent (the substituent is at least one of halogen, $C_{1-4}$ alkyl, $C_{1-3}$ alkoxyl, $C_{1-2}$ alkylamino, dimethylamino, $C_{2-3}$ acyl, trifluoroacetylamino, $C_{1-2}$ alkoxy-carbonyl, methylsulfonyl, trifluoromethylsulfonyl, $C_{1-2}$ haloalkyl or $C_{1-2}$ haloalkyloxyl)], $CH_2$-$(CH_2)_n$-$CO_2B^{22}$ [wherein -$B_{22}$ is the same meaning as defined above, and n is an integer of 1 to 4], $CH_2$—Y—$B^{23}$ [wherein B²³ represents hydrogen, $C_{1-5}$ alkyl, cyanomethyl, $C_{2-5}$ acyl, chloroacetyl or dimethyl-carbamoyl, and Y is oxygen or sulfur], $CH_2$—Y—$CH(B^{21})CO_2B^{22}$ [wherein B²¹, and B²² and Y are the same meanings as defined above], or $CH_2$—Y-$(CH_2CH_2)_r$-$CO_2B^{22}$ [wherein B²², n and r are the same meanings as defined above], and
X represents oxygen or sulfur.
The uracil derivatives represented by the formula (IV) are set forth below.

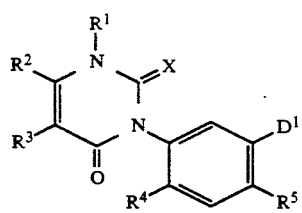

wherein
R¹ represents hydrogen, $C_{1-3}$ alkyl or $C_{1-3}$ haloalkyl,
R² represents $C_{1-6}$ haloalkyl,
R³ represents hydrogen, $C_{1-6}$ alkyl, $C_{1-6}$ haloalkyl, hydroxymethyl, halogen or nitro,
R⁴ represents hydrogen or halogen,
(i) when R⁵ and D¹ are taken separately,
R⁵ represents halogen, nitro or cyano, D¹ represents

[wherein D²¹ represents hydrogen, $C_{1-3}$ alkyl, $C_{1-3}$ alkoxyl or $C_{1-3}$ alkoxy-$C_{1-2}$ alkyl, and D²² represents hydrogen, $C_{1-4}$ alkyl, $C_{3-6}$ cycloalkyl, $C_{2-3}$ haloalkyl, phenyl or benzyl],

[wherein D²¹ and D²² are the same meanings as defined above, and D²³ represents hydrogen or $C_{1-3}$ alkyl],

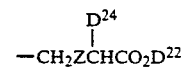

[wherein D²² is the same meaning as defined above, and D²⁴ represents hydrogen, $C_{1-3}$ alkyl or $C_{1-3}$ alkoxy-$C_{1-2}$ alkyl, and Z represents oxygen, sulfur or NH],

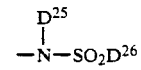

[wherein D²⁵ represents hydrogen, sodium, $C_{1-4}$ alkyl, $C_{2-5}$ alkenyl, $C_{3-5}$ alkynyl, $C_{2-5}$ acyl, $C_{1-4}$ alkylsulfonyl or $C_{1-3}$ alkoxy-$C_{1-2}$ alkyl, and D²⁶ represents $C_{1-4}$ alkyl or $C_{1-3}$ haloalkyl],

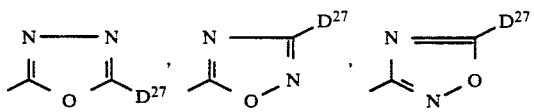

[wherein D²⁷ represents hydrogen, $C_{1-6}$ alkyl, $C_{3-6}$ cycloalkyl, $C_{1-3}$ haloalkyl, $C_{1-4}$ alkoxyl, $C_{1-4}$ alkylthio, $C_{1-4}$ alkoxy-carbonyl, mercapto, hydroxyl, $C_{1-3}$ alkoxy-$C_{1-2}$ alkyl, $C_{1-4}$ alkylamino, $ND^{28}(D^{29})$ (wherein D²⁸ and D²⁹ represent each independently $C_{1-4}$ alkyl), dimethylcarbamoyl, CONHSO $C_{1-4}$ alkylsulfonyl, or $N(D^{30})SO_2D^{31}$ (wherein D³⁰ represents hydrogen, sodium, $C_{1-4}$ alkyl, $C_{1-4}$ alkylsulfonyl or $C_{1-3}$ alkoxy-$C_{1-2}$ alkyl, and D³¹ represents $C_{1-4}$ alkyl or $C_{1-3}$ haloalkyl)

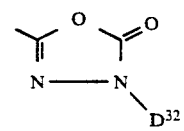

[wherein D³² represents $C_{1-6}$ alkyl or $C_{3-6}$ cycloalkyl],

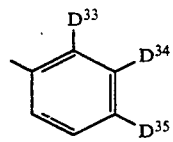

[wherein $D^{33}$, $D^{34}$ and $D^{35}$ represents each independently hydrogen or $C_{1-6}$ alkyl],

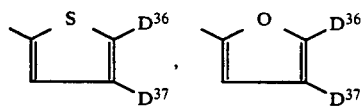

[wherein $D^{36}$ and $D^{37}$ represent each independently hydrogen, $C_{1-6}$ alkyl or dimethylamino],

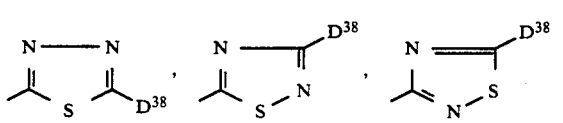

[wherein $D^{38}$ represents hydrogen, halogen, mercapto, hydroxyl, $C_{1-6}$ alkyl, $C_{3-6}$ cycloalkyl, $C_{1-3}$ haloalkyl, $C_{1-4}$ alkoxyl, $C_{1-4}$ alkylthio, $C_{1-4}$ alkoxycarbonyl, dimethylcarbamoyl, $C_{1-3}$ alkoxy-$C_{1-2}$ alkyl, $C_{1-4}$ alkylamino, $ND^{28}(D^{29})$ (wherein $D^{28}$ and $D^{29}$ are the same meanings as defined above), $CONHSO_2CH_3$, $C_{1-4}$ alkylsulfonyl, phenyl, benzyl or $N(D^{39})SO_2D^{31}$ (wherein $D^{31}$ is the same meaning as defined above, and $D^{39}$ represents hydrogen, $C_{1-4}$ alkyl, sodium, potassium, $C_{1-4}$ alkylsulfonyl or $C_{1-3}$ alkoxy-$C_{1-2}$ alkyl)],

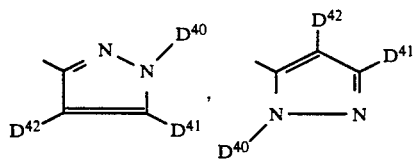

[wherein $D^{40}$ represents hydrogen, $C_{1-6}$ alkyl, $C_{3-6}$ cycloalkyl, phenyl, benzyl or 2-pyridyl, $D^{41}$ represents hydrogen, halogen, mercapto, hydroxyl, amino, $C_{1-6}$ alkyl, $C_{1-4}$ alkylamino, $ND^{28}(D^{29})$ (wherein $D^{28}$ and $D^{29}$ are the same meanings as defined above), $C_{1-4}$ alkylthio, $CO_2D^{28}$ (wherein $D^{28}$ is the same meaning as defined above), $C_{1-4}$ alkylsulfonyl, $C_{1-4}$ alkoxyl or $N(D^{29})SO_2D^{31}$ (wherein $D^{31}$ and $D^{39}$ are the same meanings as defined above), and $D^{42}$ represents hydrogen, halogen, nitro, amino, cyano, $C_{1-4}$ alkylamino, $N(D^{28})D^{29}$ (wherein $D^{28}$ and $D^{29}$ are the same meanings as defined above), $C_{1-4}$ alkylcarbonyl or $C_{1-4}$ alkoxy-carbonyl],

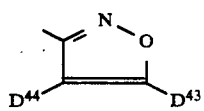

[wherein $D^{43}$ represents hydrogen, hydroxyl, methoxy, amino, benzoyl or $C_{1-4}$ alkyl, and $D^{44}$ represents hydrogen, cyano, acetyl, $C_{1-4}$ alkyl, carboxyl or $C_{1-4}$ alkoxy-carbonyl];

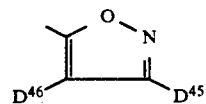

[wherein $D^{45}$ and $D^{46}$ represent each independently hydrogen, phenyl, hydroxyl, methoxy or $C_{1-4}$ alkyl]or

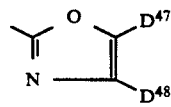

[wherein $D^{47}$ and $D^{48}$ represent each independently hydrogen or $C_{1-4}$ alkyl], and X represents oxygen or sulfur, (ii) when $R^5$ and $D^1$ form a ring, the said uracil derivatives are represented by either of the following formulae (IV-1), (IV-2), (IV-3) or (IV-4):

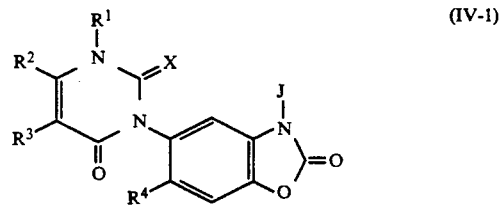

(IV-1)

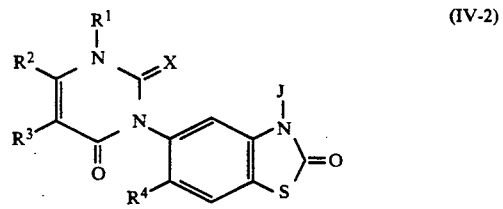

(IV-2)

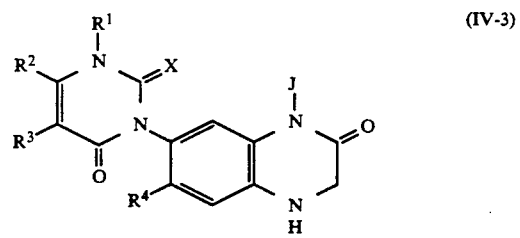

(IV-3)

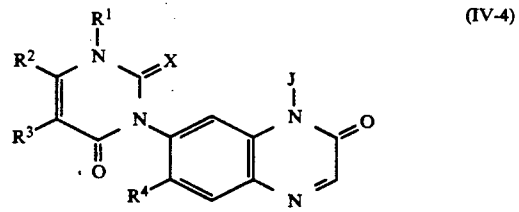

(IV-4)

wherein $R^1$, $R^2$, $R^3$, $R^4$ and X are the same meanings as defined above, and J represents hydrogen, $C_{1-4}$ alkyl, $C_{2-4}$ alkenyl, $C_{3-4}$ alkynyl, hydroxymethyl, chloromethyl, carbamoylmethyl, cyanomethyl, $C_{1-4}$ alkoxy-carbonylmethyl,

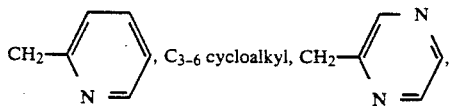, $C_{3-6}$ cycloalkyl, $C_{3-6}$ cycloalkyl-$C_{1-2}$ alkyl, $C_{1-2}$ alkoxy-$C_{1-2}$ alkyl, phenyl which may be substituted (the substituent is $C_{1-4}$ alkyl, $C_{1-4}$ alkoxyl, $C_{1-4}$ alkoxy-carbonyl, $C_{1-4}$ alkoxy- $C_{1-2}$ alkyl or halogen), or benzyl which may be substituted (the substituent is $C_{1-4}$ alkyl, $C_{1-4}$ alkoxyl, $C_{1-4}$ alkoxy-carbonyl, $C_{1-4}$ alkoxy-$C_{1-2}$ alkyl or halogen).

Among the compounds represented by the formulae (II), (III) and (IV), the followings are more preferable.

Uracil derivatives are represented by the formula (II'):

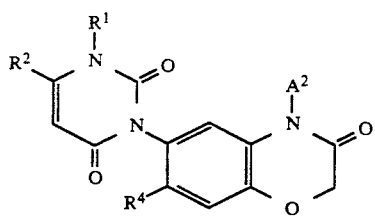

wherein
$R^1$ represents hydrogen or $C_{1-3}$ alkyl,
$R^2$ represents $C_{1-4}$ haloalkyl,
$R^4$ represents hydrogen or halogen, and
$A^2$ represents hydrogen, $C_{1-5}$ alkyl, $C_{2-5}$ alkenyl, $C_{3-5}$ alkynyl, $C_{3-6}$ cycloalkyl-$C_{1-2}$ alkyl, cyanomethyl, hydroxymethyl, chloromethyl, $C_{1-3}$ alkoxy-$C_{1-2}$ alkyl, —$CH_2CO_2A^{21}$ [wherein $A^{21}$ represents hydrogen or $C_{1-5}$ alkyl], —$CH_2CON(A^{22})A^{23}$ [wherein $A^{22}$ and $A^{23}$ represent independently hydrogen or $C_{1-3}$ alkyl], benzyl which may be substituted (the substituent is $C_{1-4}$ alkyl, $C_{1-4}$ haloalkyl, $C_{1-4}$ alkoxy or halogen, or —$CH_2A^{24}$ [wherein $A^{24}$ represents 2-pyridyl which may be substituted (the substituent being $C_{1-4}$ alkyl or halogen)].

Uracil derivatives are represented by the formula (III'):

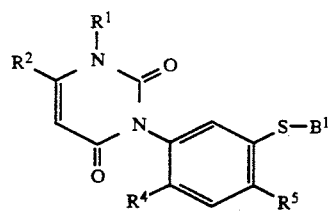

wherein
$R^1$ represents hydrogen or $C_{1-3}$ alkyl,
$R^2$ represents $C_{1-4}$ haloalkyl,
$R^4$ represents hydrogen or halogen,
$R^5$ represents chlorine or nitro, and $B^1$ represents hydrogen, $C_{1-5}$ alkyl, $C_{3-6}$ cycloalkyl, $C_{2-4}$ alkenyl, $C_{3-4}$ alkynyl, cyanomethyl, hydroxymethyl, benzyl,

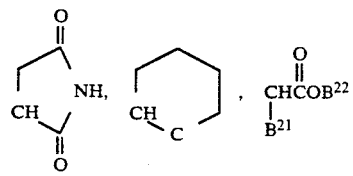

[wherein $B^{21}$ represents hydrogen, $C_{1-3}$ alkyl or methoxymethyl, and $B^{22}$ represents hydrogen, $C_{1-5}$ alkyl, $C_{2-5}$ alkenyl, $C_{3-5}$ alkynyl, $C_{3-6}$ cycloalkyl, $C_{3-6}$ cycloalkyl-$C_{1-2}$ alkyl, $C_{2-3}$ haloalkyl or benzyl which may be substituted with one or more substituent (the substituent is at least one of halogen, $C_{1-4}$ alkyl, $C_{1-3}$ alkoxyl, dimethylamino, $C_{2-3}$ acyl, $C_{1-2}$ alkoxy-carbonyl, $C_{1-2}$ haloalkyl or $C_{1-2}$ haloalkyloxy)], $CH_2$—$(CH_2)_n$—$CO_2B^{22}$ [wherein $B^{22}$ is the same meaning as defined above, and n is an integer of 1 to 3], $CH_2$—O—$B^{23}$

[wherein $B^{23}$ represents hydrogen, $C_{1-5}$ alkyl, cyanomethyl, $C_{2-5}$ acyl, chloroacetyl or dimethylcarbamoyl], or $CH_2$—O—$CH(B^{21})CO_2B^{22}$ [wherein $B^{21}$ and $B^{22}$ are the same meanings as defined above].

Uracil derivatives are represented by the formula (IV'):

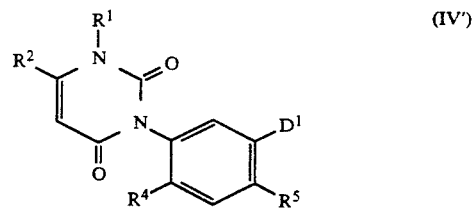

wherein
$R^1$ represents hydrogen or $C_{1-3}$ alkyl,
$R^2$ represents $C_{1-4}$ haloalkyl,
$R^4$ represents hydrogen or halogen,
 (i) when $R^5$ and $D^1$ are taken separately,
$R^5$ represents chlorine or nitro, and
$D^1$ represents

[wherein $D^{21}$ represents hydrogen, methyl, methoxy or methoxymethyl, and $D^{22}$ represents hydrogen, $C_{1-4}$ alkyl, $C_{3-6}$ cycloalkyl or benzyl],

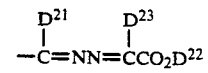

[wherein $D^{21}$ and $D^{22}$ are the same meaning as defined above, and $D^{23}$ is hydrogen or methyl],

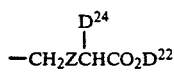

[wherein $D^{22}$ is the same meaning as defined above, $D^{24}$ represents hydrogen, methyl or methoxymethyl, and Z is oxygen, sulfur or NH],

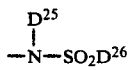

[wherein $D^{25}$ represents hydrogen, $C_{1-4}$ alkyl, $C_{2-5}$ alkenyl, $C_{3-5}$, or $C_{1-4}$ alkylsulfonyl, and $D^{26}$ represents $C_{1-4}$ alkyl],

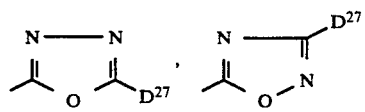

[wherein $D^{27}$ represents hydrogen, $C_{1-6}$ alkyl, $C_{1-4}$ alkoxyl, $C_{1-4}$ alkoxy-carbonyl, mercapto, hydroxyl, $C_{1-3}$ alkoxy-$C_{1-2}$ alkyl, $C_{1-4}$ alkylamino, $ND^{28}(D^{29})$ (wherein $D^{28}$ and $D^{29}$ represent each $C_{1-4}$ alkyl), dimethylcarbamoyl, $CONHSO_2CH_3$ or $N(D^{30})SO_2D^{31}$ (wherein $D^{30}$ represents hydrogen, $C_{1-4}$ alkyl or $C_{1-4}$ alkylsulfonyl, and $D^{31}$ represents $C_{1-4}$ alkyl)],

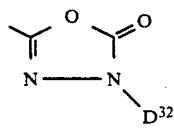

[wherein $D^{32}$ represents $C_{1-6}$ alkyl],

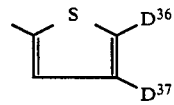

[wherein $D^{36}$ and $D^{37}$ represent each independently hydrogen or $C_{1-6}$ alkyl],

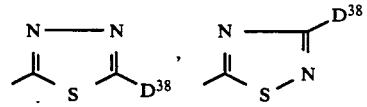

[wherein $D^{38}$ represents hydrogen, $C_{1-6}$ alkyl, $C_{1-4}$ alkoxyl, $C_{1-4}$ alkoxy-carbonyl, mercapto, hydroxyl, $C_{1-3}$ alkoxy-$C_{1-2}$ alkyl, $C_{1-4}$ alkylamino, $ND^{28}(D^{29})$ (wherein $D^{28}$ and $D^{29}$ are the same meanings as defined above), $CONHSO_2CH_3$ or $N(D^{39})$—$SO_2D^{31}$ (wherein $D^{31}$ is the same meaning as defined above, and $D^{39}$ represents hydrogen, $C_{1-4}$ alkyl or $C_{1-4}$ alkylsulfonyl)],

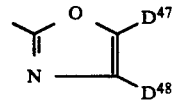

[wherein $D^{47}$ and $D^{48}$ represent each independently hydrogen or $C_{1-4}$ alkyl], (ii) when $R^5$ and $D^1$ form a ring,
said uracil derivative is represented by the following formula (IV'-1), (IV'-2) or (IV'-3):

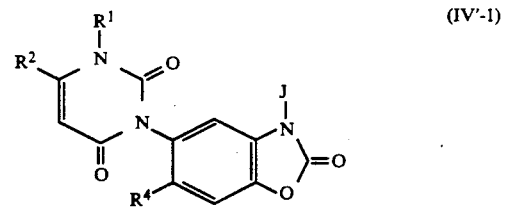

(IV'-1)

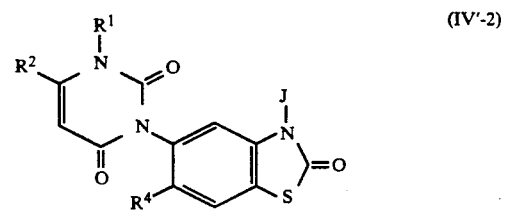

(IV'-2)

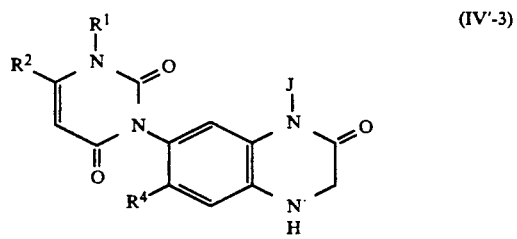

(IV'-3)

wherein $R^1$, $R^2$ and $R^4$ are the same meanings as defined above, and J represents hydrogen, $C_{1-4}$ alkyl, $C_{2-4}$ alkenyl, $C_{3-4}$ alkynyl, hydroxymethyl, chloromethyl, carbamoylmethyl, cyanomethyl, $C_{1-4}$ alkoxy-carbonylmethyl,

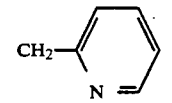

$C_{3-6}$ cycloalkyl, $C_{3-6}$ cycloalkyl-$C_{1-2}$ alkyl, $C_{1-2}$ alkoxy-$C_{1-2}$ alkyl, or benzyl which may be substituted (the substituent is $C_{1-4}$ alkyl, $C_{1-4}$ alkoxyl, $C_{1-4}$ alkoxy-carbonyl, methoxymethyl or halogen).

Among the compounds represented by the formulae (II'), (III') and (IV'), the followings are still more preferable.

Uracil derivatives are represented by the formula (II''):

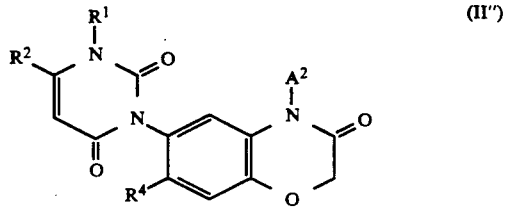

(II'')

wherein
$R^1$ represents hydrogen or methyl,
$R^2$ represents $C_{1-2}$ haloalkyl, $R^4$ represents hydrogen or fluorine, and $A^2$ represents hydrogen, $C_{1-5}$ alkyl, $C_{2-5}$ alkenyl, $C_{3-5}$ alkynyl, cyanomethyl, methoxymethyl, —CH$_2$CONH$_2$, benzyl which may be substituted (the substituent is $C_{1-4}$ alkyl, trifluoromethyl, methoxy or halogen), or —CH$_2$A$^{24}$ [wherein A$^{24}$ represents 2-pyridyl].

Uracil derivatives are represented by the formula (III''):

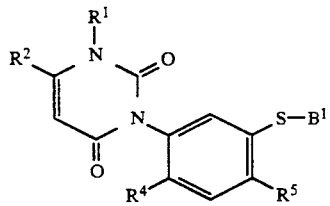

wherein
$R^1$ represents hydrogen or methyl,
$R^2$ represents $C_{1-2}$ haloalkyl,
$R^4$ represents hydrogen or fluorine,
$R^5$ represents chlorine, and
$B^1$ represents hydrogen, $C_{1-5}$ alkyl, $C_{3-6}$ cycloalkyl, $C_{2-4}$ alkenyl, $C_{3-4}$ alkynyl, benzyl, or

[wherein $B^{21}$ represents hydrogen or methyl, and $B^{22}$ represents hydrogen, $C_{1-5}$ alkyl, $C_{2-5}$ alkenyl, $C_{3-5}$ alkynyl, $C_{3-6}$ cycloalkyl or benzyl].

Uracil derivatives are represented by the formula (IV''):

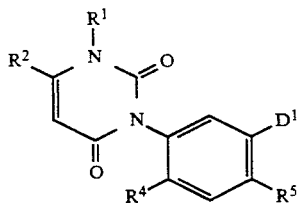

wherein
$R^1$ represents hydrogen or methyl,
$R^2$ represents $C_{1-2}$ haloalkyl,
$R^4$ represents hydrogen or fluorine,
(i) when $R^5$ and $D^1$ are taken separately,
$R^5$ represents chlorine, and
$D^1$ represents

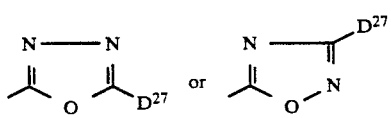

[wherein $D^{27}$ represents $C_{1-6}$ alkyl],
(ii) when $R^5$ and $D^1$ form a ring,
said uracil derivative is represented by the following formula (IV'''-1), (IV'''-2) or (IV'''-3):

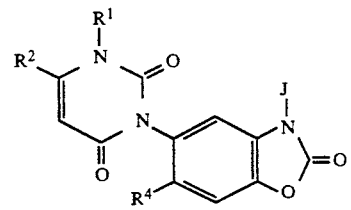

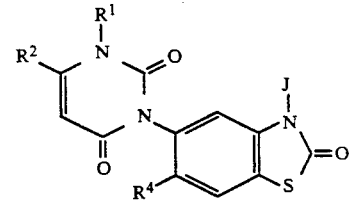

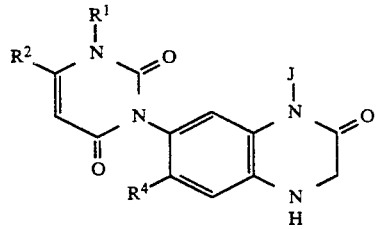

wherein $R^1$, $R^2$ and $R^4$ are the same meaning as defined above, and J represents hydrogen, $C_{1-4}$ alkyl, $C_{2-4}$ alkenyl, $C_{3-4}$ alkynyl, cyanomethyl,

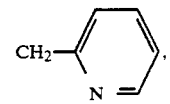

$C_{1-2}$ alkoxy-$C_{1-2}$ alkyl, or benzyl which may be substituted (the substituent is $C_{1-4}$ alkyl, methoxy or halogen).

Among the compounds of the present invention, compound Nos. A-1 to A-33, B-1, B-2, and C-1 to C-3 are especially preferred for use as active ingredient of the herbicides.

The uracil derivatives of the present invention can be synthesized according to the following reaction schemes:

Scheme 1

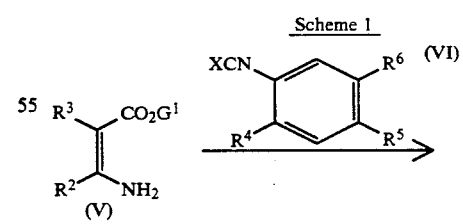

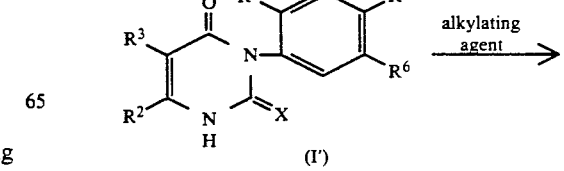

-continued

Scheme 1

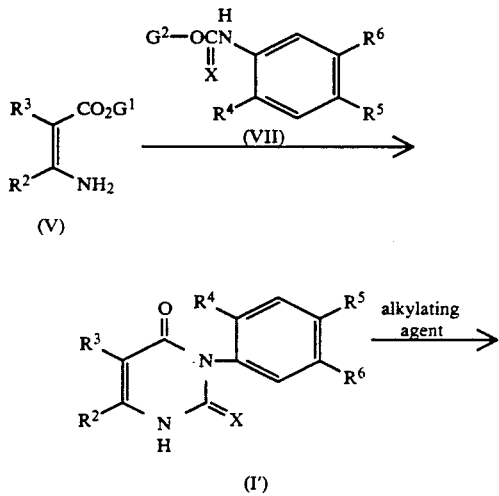

Scheme 2

Scheme 4

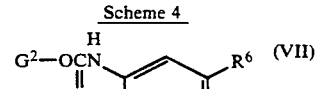

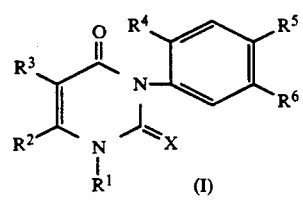

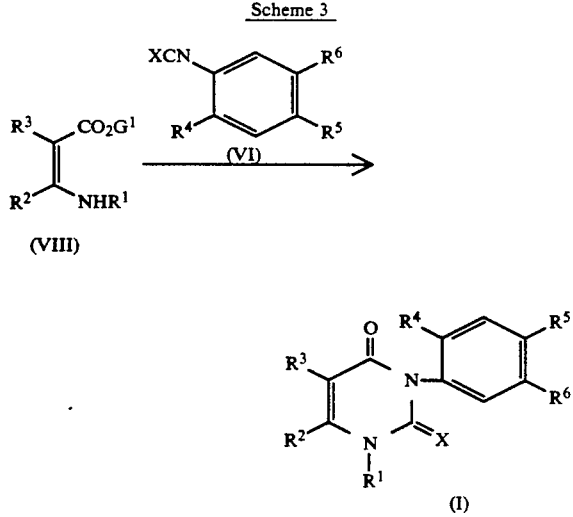

Scheme 3

(1) In Scheme 1, phenyl iso(thio)cyanate (VI) is reacted with β-aminoacrylic ester (V) to form an uracil derivative (I') at the first stage, and after isolating said derivative (I') or without isolation thereof, the 1-position of the uracil ring thereof is alkylated to produce an uracil derivative of the formula (I) at the second stage.

Reaction in the first stage

Usually phenyl iso(thio)cyanate (VI) is used in an amount of 0.5 to 1.5 equivalents, preferably 0.9 to 1.1 equivalents to β-aminoacrylic ester (V).

The reaction can proceed without solvent, but usually a solvent is used to accelerate the reaction. As the solvents usable for said purpose in the reaction, aliphatic hydrocarbons such as hexane, heptane, ligroine and petroleum ether; aromatic hydrocarbons such as benzene, toluene, xylene and chlorobenzene; halogenated hydrocarbons such as chloroform and methylene chloride; ethers such as diethyl ether, dioxane and tetrahydrofuran; ketones such as acetone and methyl ethyl ketone; nitriles such as acetonitrile and isobutyronitrile; tertiary amines such as pyridine and N,N-diethylaniline; acid amides such as formamide, N,N. dimethylformamide and N-methylpyrrolidone; sulfur containing compounds such as dimethyl sulfoxide and sulfolane; water; and mixtures thereof may be exemplified. Among them, the aliphatic hydrocarbons, the acid amides, the sulfur-containing compounds and mixtures thereof are preferred.

The reaction can proceed without base, but usually a base is used in an amount of 0.5 to 10 equivalents, preferably 1.0 to 2.0 equivalents to β-aminoacrylic ester (V). As base, there can be used, for instance, organic bases containing nitrogen such as pyridine, triethylamine and 1,4-diazabicyclo 2,2,2-octane; inorganic bases such as sodium hydride, potassium hydride, sodium hydroxide, potassium hydroxide, sodium carbonate and potassium carbonate; and metal alcoholates such as sodium methoxide, sodium ethoxide and potassium-tert-butoxide. Among them, sodium hydride, sodium hydroxide and potassium hydroxide are preferred.

Reaction temperature is usually from −40° to 200° C., preferably from room temperature to reflux temperature of the reaction mixture.

Reaction time is usually 10 minutes to 72 hours, preferably 30 minutes to 24 hours.

After the reaction is completed, the derivative (I') can be isolated by making the reaction product acidic with a mineral acid such as hydrochloric acid or an organic acid such as acetic acid, trifluoroacetic acid, p-toluenesulfonic acid or the like.

Reaction in the second stage

In the second stage of reaction, the derivative (I') is alkylated by using an alkylating agent in an amount of 1.0 to 10 equivalents, preferably 1.0 to 5.0 equivalents to the derivative (I'). As alkylating agent, there can be used, for instance, alkylsulfuric acids such as dimethylsulfuric acid and diethylsulfuric acid; and alkyl halides such as methyl chloride, ethyl chloride, methyl bromide, ethyl bromide, methyl iodide and ethyl iodide.

The reaction can proceed without solvent, but usually a solvent is used to accelerate the reaction. As the solvents usable for the said purpose in the above reaction, aliphatic hydrocarbons such as hexane, heptane, ligroine and petroleum ether; aromatic hydrocarbons such as benzene, toluene, xylene and chlorobenzene; halogenated hydrocarbons such as chloroform and methylene chloride; ethers such as diethyl ether, dioxane and tetrahydrofuran; ketones such as acetone and methyl ethyl ketone; nitriles such as acetonitrile and isobutyronitrile; tertiary amines such as pyridine and N,N- diethylaniline; acid amides such as formamide, N,N-dimethylformamide and N-methylpyrrolidone; sulfur-containing compounds such as dimethyl sulfoxide and sulfolane; water and mixtures thereof may be exemplified. Among them, the aliphatic hydrocarbons, the acid amides, the sulfur-containing compounds and mixtures thereof are preferred.

In the above reaction, usually a base is used in an amount of 1.0 to 10 equivalents, preferably 1.0 to 2.0 equivalents to the derivative (I'). As base, there can be used organic bases containing nitrogen such as pyridine, triethylamine and 1,4-diazabicyclo.2,2,2-octane; and inorganic bases such as sodium hydride, potassium hydride, sodium hydroxide, potassium hydroxide, sodium carbonate and potassium carbonate. Among them, such inorganic bases as sodium hydride and potassium carbonate are preferred.

Reaction temperature is usually from 0° to 150° C., preferably from room temperature to reflux temperature of the reaction mixture.

Reaction time is usually 10 minutes to 96 hours, preferably 30 minutes to 48 hours.

(2) According to Scheme 2, N-phenyl carbamate (VII) is reacted with β-aminoacrylic ester (V) to form an uracil derivative (I') at the first stage, and after isolating the derivative (I') or without isolation thereof, the 1-position of the uracil ring thereof is alkylated to produce an uracil derivative of the formula (I) at the second stage.

Reaction in the first stage

Usually N-phenyl carbamate (VII) is used in an amount of 0.5 to 1.5 equivalents, preferably 0.9 to 1.1 equivalents to β-aminoacrylic ester (V).

Usually a solvent is required to be present in the reaction. As solvent, there can be used, for instance, aliphatic hydrocarbons such as hexane, heptane, ligroine and petroleum ether; aromatic hydrocarbons such as benzene, toluene, xylene and chlorobenzene; halogenated hydrocarbons such as chloroform and methylene chloride; ethers such as diethyl ether, dioxane and tetrahydrofuran; ketones such as acetone and methyl ethyl ketone; nitriles such as acetonitrile and isobutyronitrile; tertiary amines such as pyridine and N,N-diethylaniline; acid amides such as formamide, N,N-dimethylformamide and N-methylpyrrolidone; sulfur-containing compounds such as dimethyl sulfoxide and sulfolane; alcohols such as methanol, ethanol, propanol and butanol; water; and mixtures thereof. Among them, the aliphatic hydrocarbons, the acid amides, the sulfur-containing compounds and mixtures thereof are preferred.

In the above reaction, usually a base is used in an amount of 0.5 to 10 equivalents, preferably 1.0 to 2.0 equivalents to β-aminoacrylic ester (V). The bases usable in the above reaction include inorganic bases such as sodium hydride, potassium hydride, sodium hydroxide, potassium hydroxide, sodium carbonate and potassium carbonate; metal alcoholates such as sodium methoxide, sodium ethoxide and potassium-tert-butoxide; and metal alkyl mercaptides such as sodium methyl mercaptide and sodium ethyl mercaptide. Among them, inorganic bases such as sodium hydride and metal alcoholates such as sodium methoxide are preferred.

The reaction is carried out at a temperature of usually from 0° to 200° C., preferably from room temperature to reflux temperature of the reaction mixture.

Reaction time is usually 10 minutes to 72 hours, preferably 30 minutes to 12 hours.

After the completion of the reaction, the derivative (I') can be isolated from the reaction mixture by acidifying it with a mineral acid such as hydrochloric acid or an organic acid such as acetic acid, trifluoroacetic acid and p-toluenesulfonic acid.

Reaction in the second stage

Alkylation of the derivative (I') can be effectuated under the same reaction conditions as in the second stage of Scheme 1.

(3) In Scheme 3, phenyl iso(thio)cyanate (VI) is reacted with N-substituted-β-aminoacrylic ester (VIII) to produce an uracil derivative of the formula (I) in a single stage. It is possible to employ the same reaction conditions as used in Scheme 1.

(4) In Scheme 4 N-phenyl carbamate (VII) is reacted with N-substituted-β-aminoacrylic ester (VIII) to produce an uracil derivative of the formula (I) in a single stage. The reaction can be performed under the same reaction conditions as used in Scheme 2.

The uracil derivatives of the present invention can be applied as a herbicide for upland field, paddy fields and non-arable land through either soil treatment or foliage treatment. Also, they show high herbicidal activities at a low dosage against, for instance, broad-leaved weeds of Solanaceae weeds such as *Solanum nigrum* and *Datura nigrum*, Malvaceae weeds such as *Abutilon theophrasti* and *Side spinosa*, Convolvulaceae weeds such as *Ipomoea* spps. of *Ipomoea purpurea*, and *Calystegia* spps., Amaranthaceae weeds such as *Amaranthus lividus* and Amaranthus retroflexus, Compositae weeds such as *Xanthium pensylvanicum, Ambrosia artemisiaefolia, Helianthus annuus, Galinsoga ciliata, Cirsium arvense, Senecio vulgaris* and *Erigeron annus*, Crucifereae weeds such as *Rorippa indica, Sinapis arvensis* and *Capsella Brusapastris*, Polyzonaceae weeds such as *Polygonum Blume* and Polygonum convolvulus, Portulacaceae weeds such as *Portulaca oleracea*, Chenopodiaceae weeds such as *Chenopodium album, Chenopodium ficifolium* and *Kochias coparia*, Caryophyllaceae weeds such as *Stellaria media*, Scrophulariaceae weeds such as *Veronica persica*, Commelinaceae weeds such as *Commelina communis*, Labiatae weeds such as *Lamium amplexicaule* and *Lamium purpureum*, Euphorbiaceae weeds such as *Euphorbia supina* and *Euphorbia maculata*, Rubiaceae weeds such as *Balium spurium, Galium aparine* and *Rubiaakane*, Violaceae weeds such as *Viola arvensis*, and Leguminosae weeds such *Sesbania exaltata* and *Cassia obtusifolia*; Graminaceous weeds such as *Sorgham bicolor, Panicum dichotomiflorum, Sorphum halepense, Echinochloa curs-galli, Digitariaadscendens, Avena fatua, Eleusine indica, Setaria viridis* and *Alopecurus aegualis*; Cyperaceous weeds such as *Cyperus rotundus*; and paddy weeds of Alismataceae weeds such as *Alisma canaliculatum, Sagittaria trifolia* and *Sagittaria pygmaea*, Cyperaceae weeds such as *Cyperus difformis, Cyperus serotinus, Scirpus juncoides* and *Eleocharis kuroguwai*, Scrothulariaceae weeds such as *Lindemia pyxidaria*, Potenderiaceae weeds such as *Monochoria Vaginalis*, Potamogetonaceae weeds such as *Potamogeton distinctus*, Lythraceae weeds such as *Rotala indica* and Graminaea weeds such as *Echinochloa crus-galli*. It is also quite remarkable that the uracil derivatives of the present invention do no harm to the important crops such as wheat, corn, barley, soybean, rice, cotton, sugar beet and sorghum.

Further, the uracil derivatives of the present invention are also useful as a defoliant.

In use of the compounds of present invention as a herbicide, they are usually mixed with a carrier, for example, a solid carrier such as clay, talc, bentonite, diatomaceous earth and white carbon (fine silica powder), or a liquid carrier such as water, alcohols (isopropanol), butanol, benzyl alcohol, furfuryl alcohol, etc.), aromatic hydrocarbons (toluene, xylene, etc.), ethers (anisole, etc.) ketones (cyclohexanone, isophorone, etc.), esters (butyl acetate, etc.), acid amides (N. methylpyrrolidone, etc.) and halogenated carbons (chlorobenzene, etc.). Also, if necessary, they may be added with a suitable adjuvant such as surfactant, emulsifier, dispersant, penetrating agent, spreader, thickener, anti-freezing agent, coagulation preventing agent, stabilizer and the like, and can be offered to practical use in various forms of formulation such as liquid formulation, emulsifiable concentrate, wettable powder, dry flowable, flowable, dust and granule.

The compounds of present invention may be mixed, if necessary, with other kinds of herbicide, various kinds of insecticide, fungicide, plant growth regulating agent, synergism agent and the like in the course of preparation or at the time of application of the formulation.

As the kinds of herbicide that can be mixed with the compounds of present invention in use thereof, there can be mentioned, for instance, the compounds described in Farm Chemicals Handbook, 1989.

The application rate of the compound of the present invention is variable depending on the place of application, time of application, method of application, kind of crop to be treated, etc., but it is usually appropriate to apply the compound of the present invention in an amount of about 0.0001 to 10 kg/ha, preferably 0.001 to 5 kg/ha measured as the amount of active ingredient.

The compounds of the present invention, as compared with the conventional herbicides, have a rapid and high herbicidal effect at a very low dosage and can be applied through either soil treatment or foliage treatment against a wise variety of weeds.

The present invention is explained in more detail in the following Examples; however, it should be recognized that the scope of the present invention is not restricted to these Examples.

EXAMPLE A-1

Synthesis of 3-(7-fluoro-3-oxo-4-propargyl-2H-1,4-benzoxazin-6-yl)-1-methyl-6-trifluoromethyl-2,4(1H,3H)-pyrimidinedione (compound A-1)

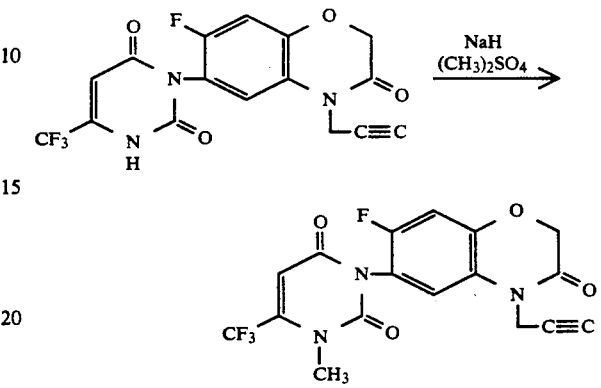

0.18 g of 3-(7-fluoro-3-oxo-4-propargyl-2H-1,4-benzoxazin-6-yl)-6-trifluoromethyl-2,4(1H,3H)-pyrimidinedione was added at room temperature in a dimethylformamide solution (2 ml) having suspended therein 0.02 g of sodium hydride (purity: 55%). After standing for 20 minutes, the solution was further added with 0.09 g of dimethylsulfuric acid and stirred overnight. Then dimethylformamide was distilled off and the residue was extracted with ethyl acetate by adding water. The extract was washed with a saturated sodium chloride aqueous solution and dried over anhydrous sodium sulfate, and then ethyl acetate was distilled off to obtain a crude product. This crude product was purified by preparative thin-layer chromatography using hexane/ethyl acetate (3:1) as developing solvent to obtain 0.15 g of the objective compound as a colorless viscous oil. It was solidified when left as it was.

EXAMPLE-2

Synthesis of 3-(7-fluoro-3-oxo-4-propargyl-2H-1,4-benzoxazin-6-yl)-6-trifluoromethyl-2,4 (1H,3H)-pyrimidinedione (compound A-2)

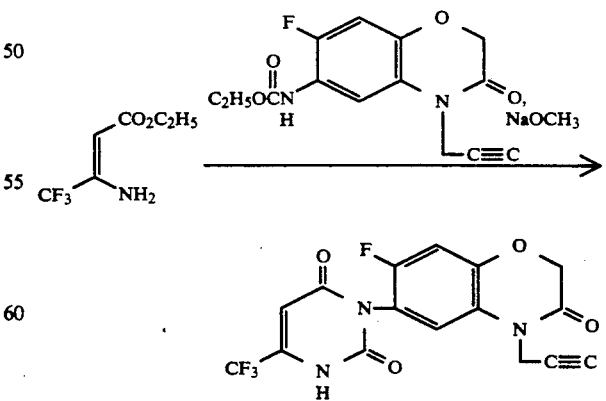

1.10 g of ethyl 3-amino-4,4,4-trifluorocrotonate was added to a mixture of 0.33 g of sodium methoxide and 5 ml of dimethylformamide at room temperature. After standing for 20 minutes, the mixed solution was added with 1.76 g of 6-ethoxycarbonylamino-7-fluoro-3-oxo-4-propargyl-2H-1,4-benzoxazine and heated at 130° C. for 4 hours. After cooling the solution to room temperature, the solution was poured into ice water and the resultant solution was extracted twice with diethyl ether. The aqueous layer was made acidic with dilute hydrochloric acid and extracted three times with ethyl acetate. The ethyl acetate extract was washed with a saturated sodium chloride aqueous solution and dried over anhydrous sodium sulfate. After distilling off ethyl acetate, the residue was purified by column chromatography using chloroform as developing solvent to obtain 0.20 g of the objective compound as pale yellow crystals.

EXAMPLE A-3

Synthesis of 3-(7-fluoro-3-oxo-4-(2-pyridylmethyl)-2H-1,4-benzoxazin-6-yl)-1-methyl-6-trifluoromethyl-2,4(H,3H)-pyrimidinedione (compound A-3)

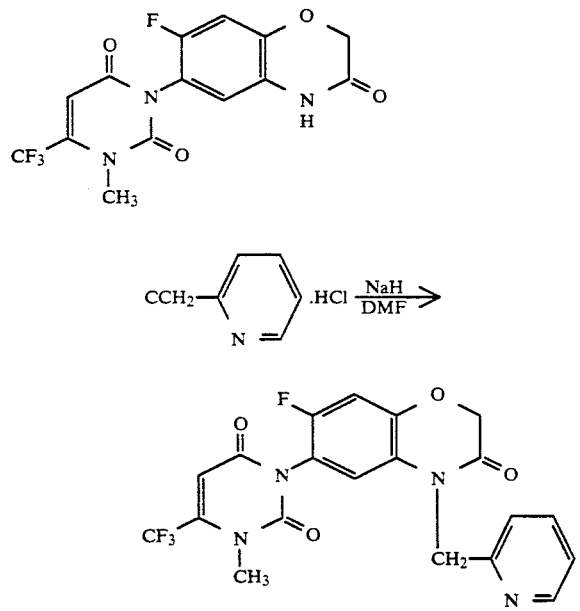

0.20 g of 3-(7-fluoro-3-oxo-2H-1,4-benzoxazin-6-yl)-1-methyl-6-trifluoromethyl-2,4(1H,3H)-pyrimidinedione was added at room temperature to an N,N-dimethylformamide solution (5 ml) having suspended therein 0.05 g of sodium hydride (purity: 55%). After standing for 20 minutes, the solution was added with 0.09 g of 2-chloromethylpyridine hydrochloride and stirred for 4 hours. Then N,N-dimethylformamide was distilled off and the residue was extracted with ethyl acetate by adding water. The extract was washed with a saturated sodium chloride aqueous solution and dried over anhydrous sodium sulfate, and then ethyl acetate was distilled off to obtain a crude product. This product was purified by preparative thin-layer chromatography using hexane/ethyl acetate (2:3) as developing solvent to obtain 0.09 g of the objective compound as pale yellow crystals.

EXAMPLE A-4

Synthesis of 3-(7-fluoro-3-oxo-2H-1,4-benzoxazin-6-yl)-1-methyl-6-trifluoromethyl-2,4(1H,3H)-pyrimidinedione (compound A-4)

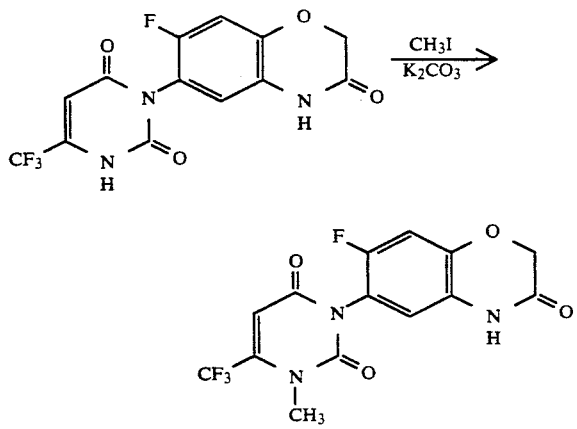

0.85 g of 3-(7-fluoro-3-oxo-2H-1,4-benzoxazin-6-yl)-6-trifluoromethyl-2,4(1H,3H)-pyrimidinedione was dissolved in 8.5 ml of N,N-dimethylformamide. Then 0.17 g of anhydrous potassium carbonate and 0.15 ml of methyl iodide were added and the mixed solution was stirred for 4 hours. After the reaction was completed, N,N-dimethylformamide was distilled off and the residue was extracted with ethyl acetate by adding water. The extract was washed with a saturated sodium chloride aqueous solution and dried over anhydrous sodium sulfate, and then ethyl acetate was distilled off to obtain a crude product. This product was purified by column chromatography using chloroform as developing solvent to yield 0.53 g of the objective compound as pale yellow crystals.

EXAMPLE B-1

Synthesis of 3-(4-chloro-2-fluoro-5-methoxycarbonylmethylthiophenyl)-1-methyl-6-trifluoromethyl-2,4(1H,3H)-pyrimidinedione (compound B-1)

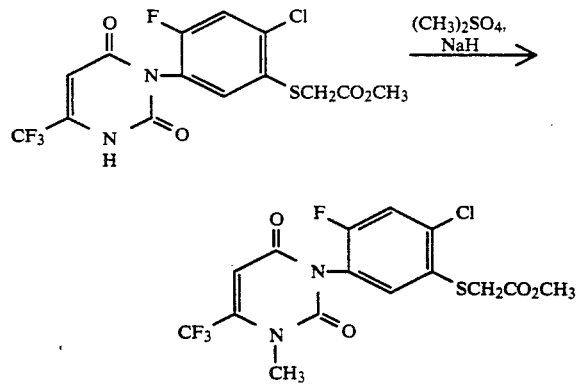

To a suspension of 0.16 g of sodium hydride (purity: 55%) in 5 ml of dimethylformamide, a solution of 1.5 g of 3-(4-chloro-2-fluoro-5-methoxycarbonylmethylthiophenyl)-6-trifluoromethyl-2,4(1H,3H)-pyrimidinedione in 10 ml of dimethylformamide was added dropwise at room temperature. After evolution of hydrogen ceased, 0.59 g of dimethylsulfuric acid was added and the resultant solution was stirred at room temperature for 3 hours. The reaction mixture was poured into 300 ml of water and extracted twice with ethyl acetate. The extract was washed with a saturated sodium chloride aqueous solution and dried over anhydrous sodium sulfate, and then ethyl acetate was distilled off to obtain a crude product. The obtained product was purified by preparative thin-layer chromatography (developing solvent: CHCl₃) and then by preparative high performance liquid chromatography [eluent: CHCN/H₂O (5:1)] to obtain 0.1 g of the objective compound as viscous oil.

EXAMPLE B-2

Synthesis of 3-(4-chloro-2-fluoro-5-methoxycarbonylmethylthiophenyl)-6-trifluoromethyl-2,4(1H,3H)-pyrimidinedione (compound B-2)

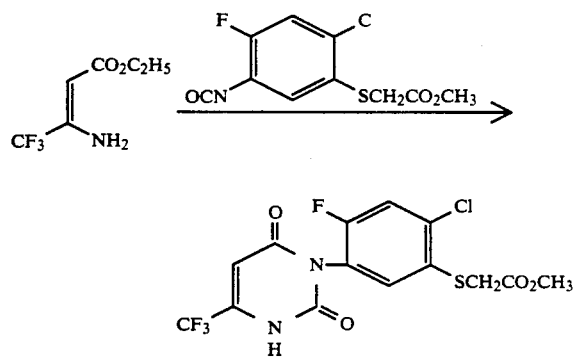

A solution of 4.75 g of ethyl 3-amino-4,4,4-trifluorocrotonate in 50 ml of anhydrous toluene was added dropwise to a solution prepared by suspending 1.14 g of sodium hydride (purity: 55%) in 110 ml of dimethylformamide. Said dropwise addition was conducted at 0° C. under stirring over a period of 15 minutes. The resulting mixture was further stirred at 0° C. for 15 minutes. Then the reaction mixture was cooled to −30° C., and a solution of 6.9 g of 4-chloro-2-fluoro-5-methoxycarbonylmethylthiophenyl isocyanate in 50 ml of anhydrous toluene was added dropwise thereto. The resulting reaction mixture was returned to room temperature and stirred for 2 hours. After distilling off the solvent, the residual solution was added with ethyl acetate, washed twice with a solution of 20 ml of 2N hydrochloric acid and 500 ml of water, washed with a saturated sodium chloride aqueous solution, and dried over anhydrous sodium sulfate, and then ethyl acetate was distilled off to obtain a crude product. This crude product was preliminarily purified by silica gel column chromatography using CHCl₃ as developing solvent and then purified by silica gel column chromatography using ethyl acetate/hexane (3:1) as developing solvent to obtain 1.5 g of the objective compound as viscous oil.

EXAMPLE C-1

Synthesis of 3-(4-chloro-2-fluoro-5-(5-methyl-1,3,4-oxadiazol-2-yl)phenyl)-1-methyl-6-trifluoromethyl-2,4(1H,3H)-pyrimidinedione (compound C-1)

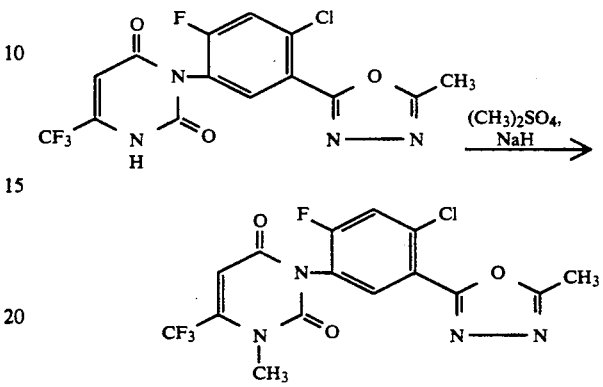

To a suspension of 0.31 g of sodium hydride (oil, purity: 55%) in 13 ml of dimethylformamide, a solution of 2.5 g of 3-(4-chloro-2-fluoro-5-(5-methyl-1,3,4-oxadiazol-2-yl)phenyl)-6-trifluoromethyl-2,4(1H,3H)-pyrimidinedione in 20 ml of N,N-dimethylformamide was added dropwise at 25° C. After evolution of hydrogen ceased, 1.02 g of dimethylsulfuric acid was added over a period of 15 minutes. The mixed solution was stirred at room temperature for 2 hours and extracted with ethyl acetate by adding water. The extract was dried over anhydrous sodium sulfate. Then the solvent was distilled off and the residue was purified by preparative high performance liquid chromatography using acetonitrile/water (5:1) as eluent to obtain 0.78 g of the objective compound.

EXAMPLE C-2

Synthesis of 3-(4-chloro-2-fluoro-5-(5-methyl-1,3,4-oxadiazol-2-yl)phenyl)-6-trifluoromethyl-2,4(1H,3H)-pyrimidinedione (compound C-2)

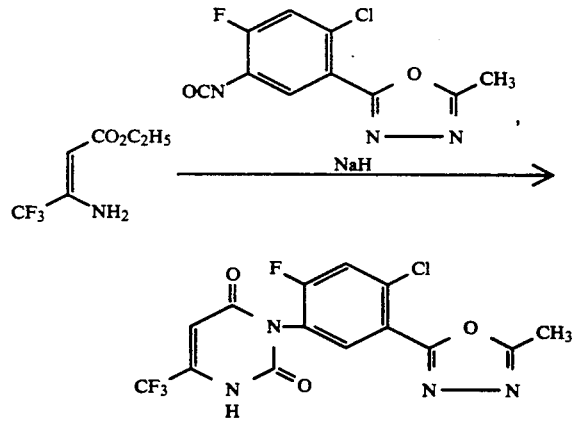

To a suspension of 1.04 g of sodium hydride (oil, purity: 55%) in 75 ml of dimethylformamide, a solution of 4.3 g of ethyl 3-amino-4,4,4-trifluorocrotonate in 58 ml of toluene was added dropwise at 0° C. over a period of 15 minutes. Thereafter, the solution was stirred at 0°

C. for 15 minutes and then cooled to −30° C., followed by dropwise addition of a solution of 5.7 g of 4-chloro-2-fluoro-5-(5-methyl-1,3,4-oxadiazol-2-yl)phenyl isocyanate in 60 ml of toluene. The resulting mixed solution was stirred at room temperature for 3 hours.

Then the solvent was distilled off under reduced pressure and the resultantly obtained oily substance was added with a solution of 13.3 ml of 2N hydrochloric acid and 300 ml of water and extracted twice with ethyl acetate. The ethyl acetate layer was washed with a saturated sodium chloride aqueous solution and dried over anhydrous sodium sulfate. Then the solvent was distilled off and the resulting crude product was purified by preparative high performance liquid chromatography using acetonitrile/water (5:1) as eluent to obtain 1.78 g of the objective compound.

The uracil derivatives of the present invention synthesized according to the above Examples and synthesized by following the similar procedures to the above Examples or Schemes are shown in Tables 1-A, 1-B and 1-C, and the physical properties of these compounds are shown in Tables 2-A, 2-B and 2-C. It is to be understood, however, the uracil derivatives obtainable in accordance with the present invention are not limited to those shown in the following tables.

TABLE 1-A

| Compound No. | Structural formula |
|---|---|
| A-1 | |
| A-2 | |
| A-3 | |
| A-4 | |
| A-5 | |
| A-6 | |
| A-7 | |
| A-8 | |
| A-9 | |
| A-10 | |
| A-11 | |

TABLE 1-A-continued

| Compound No. | Structural formula |
|---|---|
| A-12 | (structure: uracil with CF₃, N-CH₃; linked to fluorophenyl-O-CH₂-C(=O)-N-CH₂-phenyl) |
| A-13 | (structure: uracil with CF₃, NH; linked to fluorophenyl-O-CH₂-C(=O)-N-CH₂CH₃) |
| A-14 | (structure: uracil with CF₃, N-CH₃; linked to fluorophenyl-O-CH₂-C(=O)-N-CH₂CH₃) |
| A-15 | (structure: uracil with CF₃, NH; linked to fluorophenyl-O-CH₂-C(=O)-N-CH₂CH₂CH₃) |
| A-16 | (structure: uracil with CF₃, N-CH₃; linked to fluorophenyl-O-CH₂-C(=O)-N-CH₂CH₂CH₃) |
| A-17 | (structure: uracil with CF₃, NH; linked to fluorophenyl-O-CH₂-C(=O)-N-CH(CH₃)₂) |
| A-18 | (structure: uracil with CF₃, N-CH₃; linked to fluorophenyl-O-CH₂-C(=O)-N-CH(CH₃)₂) |
| A-19 | (structure: uracil with CF₃, NH; linked to fluorophenyl-O-CH₂-C(=O)-N-CH₂CH=CH₂) |
| A-20 | (structure: uracil with CF₃, N-CH₃; linked to fluorophenyl-O-CH₂-C(=O)-N-CH₂CH=CH₂) |
| A-21 | (structure: uracil with CF₃, NH; linked to fluorophenyl-O-CH₂-C(=O)-N-CH(CH₃)C≡CH) |
| A-22 | (structure: uracil with CF₃, N-CH₃; linked to fluorophenyl-O-CH₂-C(=O)-N-CH(CH₃)C≡CH) |
| A-23 | (structure: uracil with CF₃, NH; linked to fluorophenyl-O-CH₂-C(=O)-N-CH₂C≡N) |
| A-24 | (structure: uracil with CF₃, N-CH₃; linked to fluorophenyl-O-CH₂-C(=O)-N-CH₂C≡N) |
| A-25 | (structure: uracil with CF₃, NH; linked to fluorophenyl-O-CH₂-C(=O)-N-CH₂OCH₃) |

TABLE 1-A-continued

| Compound No. | Structural formula |
|---|---|
| A-26 | (structure) |
| A-27 | (structure) |
| A-28 | (structure) |
| A-29 | (structure) |
| A-30 | (structure) |
| A-31 | (structure) |
| A-32 | (structure) |
| A-33 | (structure) |

TABLE 1-B

| Compound No. | Structural formula |
|---|---|
| B-1 | (structure) |
| B-2 | (structure) |

TABLE 1-C

| Compound No. | Structural formula |
|---|---|
| C-1 | (structure) |
| C-2 | (structure) |
| C-3 | (structure) |

TABLE 2-A

| Compound No. | $^1$H-NMR δ (ppm) [solvent] | Physical properties |
|---|---|---|
| A-1 | 2.31(1H, t, J=2Hz), 3.60(3H, s), 4.69(2H, d, J=2Hz), 4.73(2H, s), | m.p.: 158–160° C. |

TABLE 2-A-continued

| Compound No. | $^1$H-NMR δ (ppm) [solvent] | Physical properties |
| --- | --- | --- |
| | 6.43(1H, s), 7.01(1H, d, J=10Hz), 7.15(1H, d, J=7Hz) [CDCl$_3$] | |
| A-2 | 2.81(1H, t, J=2Hz), 4.80(2H, d, J=2Hz), 4.82(2H, s), 6.01(1H, s), 6.99(1H, d, J=10Hz), 7.12(1H, d, J=7Hz), 13.00(1H, br s) [d$_6$-DMSO] | m.p.: 189–193° C. |
| A-3 | 3.50(3H, s), 4.72(2H, s), 5.18(2H, d, J=4Hz), 6.28(1H, s), 6.85(1H, d, J=10Hz), 7.10(1H, d, J=8Hz), 7.02–7.41(2H, m), 7.47–7.80(1H, m), 8.36–8.60(1H, m) [CDCl$_3$] | m.p.: 161–163° C. |
| A-4 | 3.51(3H, s), 4.54(2H, s), 6.32(1H, s), 6.66(1H, d, J=8Hz), 6.80(1H, d, J=10Hz), 9.58(1H, br, s) [CDCl$_3$] | m.p.: 99–105° C. |
| A-5 | 4.65(2H, s), 6.28(1H, s), 6.72–7.37(2H, m), 10.87(2H, br s) [d$_6$-DMSO] | m.p.: ≧300° C. |
| A-6 | 3.28(3H, s), 3.54(3H, s), 4.63(2H, s), 6.35(1H, s), 6.83(1H, d, J=8Hz), 6.86(1H, d, J=10Hz) [CDCl$_3$] | m.p.: 147–152° C. |
| A-7 | 2.24(3H, s), 4.77(2H, s), 5.02(2H, br s), 6.20(1H, s), 6.66~7.29(3H, m), 7.13(4H, s) [d$_6$-DMSO] | m.p.: ≧270° C. |
| A-8 | 2.25(3H, s), 3.96(3H, br s), 4.67(2H, s), 5.01(2H, s), 6.22(1H, s), 6.65~7.23(3H, m), 7.02(4H, s) [CDCl$_3$] | m.p.: 245.4–247.0° C. |
| A-9 | 2.27(3H, s), 4.74(2H, s), 4.88(2H, s), 6.05(1H, s), 6.60~7.23(7H, m), 12.30(1H, br s) [d$_6$-DMSO] | m.p.: ≧300° C. |
| A-10 | 2.33(3H, s), 3.42(3H, s), 4.71(2H, s), 4.98(2H, s), 6.21(1H, s), 6.51(1H, br d, J=2Hz), 6.61~7.24(6H, m) [CDCl$_3$] | m.p.: 199–201° C. |
| A-11 | 4.71(2H, s), 5.04(2H, br s), 6.03(1H, s), 6.72(1H, d, J=7Hz), 6.82(1H, d, J=10Hz), 7.18(5H, br S) [d$_6$-DMSO] | m.p.: 282–287° C. |
| A-12 | 3.41(3H, br s), 4.66(2H, s), 5.01(2H, br s), 6.29(1H, s), 6.79(1H, d, J=7Hz), 6.91(1H, d, J=10Hz), 7.13(5H, br s) [CDCl$_3$] | m.p.: 85–89° C. |
| A-13 | 1.20(3H, t, J=7Hz), 3.84(2H, q, J=7Hz), 4.54(2H, s), 6.09(1H, s), 6.66(1H, d, J=7Hz), 6.71(1H, d, J=10Hz) [CDCl$_3$] | m.p.: 223–224° C. |
| A-14 | 1.04(3H, t, J=7Hz), 3.32(3H, br s), 3.70(2H, q, J=7Hz), 4.38(2H, s), 6.08(1H, s), 6.52(1H, d, J=7Hz), 6.58(1H, d, J=10Hz) [CDCl$_3$] | m.p.: 168–170° C. |
| A-15 | 1.03(3H, t, J=7Hz), 1.66(2H, tq, J=7, 7Hz), 3.78(2H, br t, J=7Hz), 4.56(2H, s), 6.11(1H, s), 6.65(1H, d, J=7Hz), 6.73(1H, d, J=10Hz) [CDCl$_3$] | m.p.: 204–206° C. |
| A-16 | 0.92(3H, t, J=7Hz), 1.65(2H, tq, J=7, 7Hz), 3.50(3H, s), 3.78(2H, br t, J=7Hz), 4.57(2H, s), 6.25(1H, s), 6.72(1H, d, J=7Hz), 6.79(1H, d, J=10Hz) [CDCl$_3$] | m.p.: 60–62° C. |
| A-17 | | |
| A-18 | | |
| A-19 | 4.36–4.61(2H, m), 4.65(2H, s), 4.90–5.40(2H, m), 5.48–5.76(1H, m), 6.17(1H, s), 6.75(1H, d, J=7Hz), 6.81(1H, d, J=10Hz), 8.50(1H, br s) | vitrified |

TABLE 2-A-continued

| Compound No. | $^1$H-NMR δ (ppm) [solvent] | Physical properties |
|---|---|---|
| A-20 | [CDCl$_3$] 3.49(3H, br s), 4.28–4.57(2H, m), 4.60(2H, s), 4.88–5.37(2H, m), 5.45–5.73(1H, m), 6.24(1H, s), 6.69(1H, d, J=7Hz), 6.78(1H, d, J=10Hz) | m.p.: 113–114° C. |
| A-21 | [CDCl$_3$] 1.53(3H, d, J=7Hz), 2.40(1H, d, J=2Hz), 4.52(2H, s), 5.90(1H, dq, J=7, 2Hz), 6.18(1H, s), 6.75(1H, d, J=10Hz), 7.35(1H, d, J=7Hz) | m.p.: 130–135° C. |
| A-22 | [CDCl$_3$] 1.63(3H, d, J=7Hz), 2.49(1H, d, J=2Hz), 3.58(3H, s), 4.62(2H, s), 5.99(1H, dq, J=7, 2Hz), 6.34(1H, s), 6.88(1H, d, J=10Hz), 7.47(1H, d, J=7Hz) | m.p.: 155–158° C. |
| A-23 | | |
| A-24 | | |
| A-25 | | |
| A-26 | | |
| A-27 | | |
| A-28 | | |
| A-29 | | |
| A-30 | | m.p.: 198–202° C. |
| A-31 | | |
| A-32 | 2.24(1H, t, J=2Hz), 3.50(3H, br s), 4.57(2H, d, J=2Hz), 4.59(2H, s), 6.18(1H, s), 6.75(1H, d, J=10Hz), 6.90(1H, d, J=7Hz) [CDCl$_3$] | m.p.: 190–192° C. |
| A-33 | | vitrified |

TABLE 2-B

| Compound No. | $^1$H-NMR δ (ppm) [solvent] | Physical properties |
|---|---|---|
| B-1 | 3.48(3H, s), 3.59(2H, s), 3.61(3H, s), 6.22(1H, s), 7.21(1H,d, J=9Hz), 7.29(1H, d, J=7Hz) [CDCl$_3$] | Oil |
| B-2 | 3.51(2H, s), 3.53(3H, s), 6.04(1H, s), 7.13(1H, d, J=9Hz), 7.23(1H, d, J=8Hz), 7.31(1H, br, s) [CDCl$_3$] | Oil |

TABLE 2-C

| Compound No. | $^1$H-NMR δ (ppm) [solvent] | Physical properties |
|---|---|---|
| C-1 | 2.57(3H, s), 3.49(3H, s), 6.25(1H, s), 7.36(1H, d, J=9Hz), 7.84(1H, d, J=7Hz) [d$_6$-DMSO] | m.p.: 65–69° C. |
| C-2 | 2.62(3H, s), 6.21(1H, s), 7.47(1H, d, J=9Hz), 7.84(1H, br s), 8.01(1H, d, J=8Hz) [d$_6$-DMSO] | m.p.: 116–121° C. |
| C-3 | 1.39(9H, s), 3.50(3H, br s), 6.25(1H, s), 7.32(1H, d, J=9Hz), 7.94(1H, d, J=7Hz) [CDCl$_3$] | m.p.: 135–139° C. |

The uracil derivative of the present invention synthesized according to the above Examples and synthesized by following the similar procedures to the above Examples or Schemes are shown in Tables 3-A-1 to 3-C-10. The compounds obtainable in accordance with the present invention, however, are not limited to those shown in the following tables.

TABLE 3-A-1

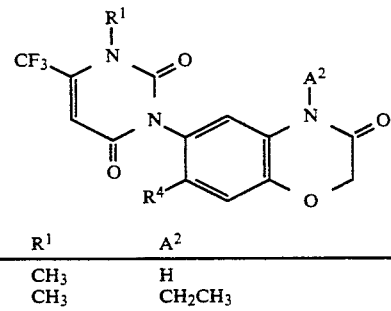

| R$^4$ | R$^1$ | A$^2$ |
|---|---|---|
| F | CH$_3$ | H |
| F | CH$_3$ | CH$_2$CH$_3$ |
| F | CH$_3$ | CH$_2$CH=CH$_2$ |
| F | CH$_3$ | CH$_2$C≡CH |
| F | H | H |
| F | H | CH$_2$CH$_3$ |
| F | H | CH$_2$CH=CH$_2$ |
| F | H | CH$_2$C≡CH |
| H | CH$_3$ | CH$_2$C≡CH |
| H | H | CH$_2$C≡CH |
| F | CH$_3$ | CH$_2$CONH$_2$ |
| F | CH$_3$ | CH$_2$CON(CH$_3$)$_2$ |
| F | CH$_3$ | CH$_2$CO$_2$H |

TABLE 3-A-1-continued

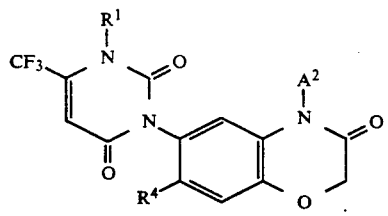

| $R^4$ | $R^1$ | $A^2$ |
|---|---|---|
| F | CH$_3$ | CH$_2$CO$_2$CH$_3$ |
| F | CH$_3$ | CH$_2$CO$_2$C$_6$H$_5$ |
| F | CH$_3$ | CH$_2$CO$_2$CH$_2$C$_6$H$_5$ |
| F | CH$_3$ | CH$_2$CO$_2$(C$_6$H$_4$-2Cl) |
| F | CH$_3$ | CH$_2$CO$_2$CH$_2$(C$_6$H$_4$-4Cl) |
| F | CH$_3$ | CH$_2$CN |
| F | CH$_3$ | CH$_2$C$_6$H$_5$ |
| F | CH$_2$OH | C$_2$H$_5$ |
| F | CH$_2$Cl | C$_2$H$_5$ |
| F | CH$_3$ | —CH$_2$(C$_6$H$_4$-4Cl) |
| F | CH$_3$ | —CH$_2$(C$_6$H$_4$-2Cl) |
| F | CH$_3$ | —CH$_2$(C$_6$H$_4$-3Cl) |
| F | CH$_3$ | CH$_2$CO$_2$Na |
| H | CH$_3$ | H |
| F | CH$_3$ | CH$_2$OH |
| F | CH$_3$ | CH$_2$Cl |
| F | CH$_3$ | CH$_2$CH$_2$CH$_3$ |
| F | CH$_3$ | CH(CH$_3$)$_2$ |
| F | CH$_3$ | CH$_2$CH$_2$CH$_2$CH$_3$ |
| F | CH$_3$ | CH(CH$_3$)CH$_2$CH$_3$ |
| F | CH$_3$ | CH$_2$CH(CH$_3$)$_2$ |
| F | CH$_3$ | CH$_2$C(CH$_3$)$_3$ |
| F | CH$_3$ | CH$_2$(CH$_2$)$_3$CH$_3$ |
| F | CH$_3$ | CH$_2$CH$_2$CH(CH$_3$)$_2$ |
| F | CH$_3$ | CH(CH$_3$)CH$_2$CH$_2$CH$_3$ |
| F | CH$_3$ | CH$_2$CH(CH$_3$)CH$_2$CH$_3$ |
| F | CH$_3$ | CH(C$_2$H$_5$)$_2$ |
| F | CH$_3$ | CH$_3$ |
| F | CH$_3$ | CH(CH$_3$)C≡CH |
| F | CH$_3$ | C(CH$_3$)$_2$C≡CH |
| F | CH$_3$ | CH(CH$_3$)CH=CH$_2$ |
| F | CH$_3$ | C(CH$_3$)$_2$CH=CH$_2$ |
| F | CH$_3$ | CH$_2$CONHCH$_3$ |
| F | CH$_3$ | CH$_2$CONHC$_2$H$_5$ |
| F | CH$_3$ | CH$_2$CON(C$_2$H$_5$)$_2$ |
| F | CH$_3$ | CH$_2$CON(CH$_2$CH$_2$CH$_3$)$_2$ |
| F | CH$_3$ | CH$_2$CON(CH(CH$_3$)$_2$)$_2$ |
| F | CH$_3$ | CH$_2$CONHCH$_2$CH$_2$CH$_3$ |
| F | CH$_3$ | CH$_2$CONHCH(CH$_3$)$_2$ |
| F | CH$_3$ | CH$_2$CO$_2$C$_2$H$_5$ |
| F | CH$_3$ | CH$_2$CO$_2$CH$_2$CH$_2$CH$_3$ |
| F | CH$_3$ | CH$_2$CO$_2$CH(CH$_3$)$_2$ |
| F | CH$_3$ | CH$_2$CO$_2$CH$_2$(CH$_2$)$_2$CH$_3$ |
| F | CH$_3$ | CH$_2$CO$_2$CH$_2$CH(CH$_3$)$_2$ |
| F | CH$_3$ | CH$_2$CO$_2$CH(CH$_3$)CH$_2$CH$_3$ |
| F | CH$_3$ | CH$_2$CO$_2$C(CH$_3$)$_3$ |
| F | CH$_3$ | CH$_2$C≡CCH$_3$ |
| F | CH$_3$ | CH$_2$CH$_2$C≡CH |
| F | CH$_3$ | CH$_2$C≡CCH$_2$CH$_3$ |
| F | CH$_3$ | CH(CH$_3$)CH$_2$C≡CH |
| F | CH$_3$ | CH$_2$CH(CH$_3$)C≡CH |
| F | CH$_3$ | CH$_2$CH=CHCH$_3$ (cis) |
| F | CH$_3$ | CH$_2$CH=CHCH$_3$ (trans) |
| F | CH$_3$ | CH$_2$CH$_2$CH=CH$_2$ |
| F | CH$_3$ | CH$_2$CH$_2$CH=CHCH$_3$ (cis) |
| F | CH$_3$ | CH$_2$CH$_2$CH=CHCH$_3$ (trans) |
| F | CH$_3$ | CH(CH$_3$)CH=CHCH$_3$ (cis) |
| F | CH$_3$ | CH(CH$_3$)CH=CHCH$_3$ (trans) |
| F | CH$_3$ | CH$_2$CH=CHCH$_2$CH$_3$ (cis) |

TABLE 3-A-1-continued

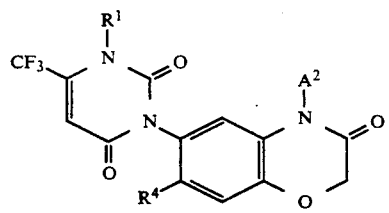

| $R^4$ | $R^1$ | $A^2$ |
|---|---|---|
| F | CH$_3$ | CH$_2$CH=CHCH$_2$CH$_3$ (trans) |
| F | H | CH$_2$CH$_2$CH$_3$ |
| F | H | CH(CH$_3$)$_2$ |
| F | H | CH$_2$CH$_2$CH$_2$CH$_3$ |
| F | H | CH(CH$_3$)CH$_2$CH$_3$ |
| F | H | CH$_2$CH(CH$_3$)$_2$ |
| F | H | CH$_2$C(CH$_3$)$_3$ |
| F | H | CH$_2$(CH$_2$)$_3$CH$_3$ |
| F | H | CH$_2$CH$_2$CH(CH$_3$)$_2$ |
| F | H | CH(CH$_3$)CH$_2$CH$_2$CH$_3$ |
| F | H | CH$_2$CH(CH$_3$)CH$_2$CH$_3$ |
| F | H | CH(C$_2$H$_5$)$_2$ |
| F | H | CH$_3$ |
| F | H | CH(CH$_3$)C≡CH |
| F | H | C(CH$_3$)$_2$C≡CH |
| F | H | CH(CH$_3$)CH=CH$_2$ |
| F | H | C(CH$_3$)$_2$CH=CH$_2$ |
| F | H | CH$_2$CONHCH$_3$ |
| F | H | CH$_2$CONHC$_2$H$_5$ |
| F | H | CH$_2$CON(C$_2$H$_5$)$_2$ |
| F | H | CH$_2$CON(CH$_2$CH$_2$CH$_3$)$_2$ |
| F | H | CH$_2$CON(CH(CH$_3$)$_2$)$_2$ |
| F | H | CH$_2$CONHCH$_2$CH$_2$CH$_3$ |
| F | H | CH$_2$CONHCH(CH$_3$)$_2$ |
| F | H | CH$_2$CO$_2$C$_2$H$_5$ |
| F | H | CH$_2$CO$_2$CH$_2$CH$_2$CH$_3$ |
| F | H | CH$_2$CO$_2$CH(CH$_3$)$_2$ |
| F | H | CH$_2$CO$_2$CH$_2$(CH$_2$)$_2$CH$_3$ |
| F | H | CH$_2$CO$_2$CH$_2$CH(CH$_3$)$_2$ |
| F | H | CH$_2$CO$_2$CH(CH$_3$)CH$_2$CH$_3$ |
| F | H | CH$_2$CO$_2$C(CH$_3$)$_3$ |
| F | H | CH$_2$C≡CCH$_3$ |
| F | H | CH$_2$CH$_2$C≡CH |
| F | H | CH$_2$C≡CCH$_2$CH$_3$ |
| F | H | CH(CH$_3$)CH$_2$C≡CH |
| F | H | CH$_2$CH(CH$_3$)C≡CH |
| F | H | CH$_2$CH=CHCH$_3$ (cis) |
| F | H | CH$_2$CH=CHCH$_3$ (trans) |
| F | H | CH$_2$CH$_2$CH=CH$_2$ |
| F | H | CH$_2$CH$_2$CH=CHCH$_3$ (cis) |
| F | H | CH$_2$CH$_2$CH=CHCH$_3$ (trans) |
| F | H | CH(CH$_3$)CH=CHCH$_3$ (cis) |
| F | H | CH(CH$_3$)CH=CHCH$_3$ (trans) |
| F | H | CH$_2$CH=CHCH$_2$CH$_3$ (cis) |
| F | H | CH$_2$CH=CHCH$_2$CH$_3$ (trans) |
| H | CH$_3$ | CH$_2$CH$_3$ |
| H | CH$_3$ | CH$_2$C≡N |
| H | CH$_3$ | CH$_2$CH=CH$_2$ |
| H | CH$_3$ | CH(CH$_3$)C≡CH |
| H | CH$_3$ | CH$_2$CONH$_2$ |
| H | CH$_3$ | CH$_2$CO$_2$CH$_3$ |
| H | CH$_3$ | CH$_2$CO$_2$C$_2$H$_5$ |
| H | CH$_3$ | CH$_2$C$_6$H$_5$ |
| H | CH$_3$ | CH$_2$CH$_2$CH$_3$ |
| H | CH$_3$ | CH(CH$_3$)CH=CH$_2$ |
| F | H | CH$_2$C$_6$H$_5$ |
| F | H | CH$_2$C≡N |

TABLE 3-A-2

| X | R¹ | R² | R³ | R⁴ | A¹ | A² |
|---|---|---|---|---|---|---|
| O | CH₃ | CF₃ | F | F | H | CH₂C≡CH |
| O | CH₃ | CF₃ | Cl | F | H | CH₂C≡CH |
| O | CH₃ | CF₃ | Br | F | H | CH₂C≡CH |
| O | CH₃ | CF₃ | NO₂ | F | H | CH₂C≡CH |
| O | CH₃ | CF₃ | CH₃ | F | H | CH₂C≡CH |
| O | CH₃ | CF₃ | CH₂CH₃ | F | H | CH₂C≡CH |
| O | CH₃ | CF₃ | CH₂CH₂CH₃ | F | H | CH₂C≡CH |
| O | CH₃ | CF₃ | CH(CH₃)₂ | F | H | CH₂C≡CH |
| O | CH₃ | CF₃ | CF₃ | F | H | CH₂C≡CH |
| O | CH₃ | CF₃ | HOCH₂ | F | H | CH₂C≡CH |
| O | CH₃ | CF₃ | Cl | F | H | CH(CH₃)C≡CH |
| O | CH₃ | CF₃ | Cl | F | H | CH₂CH=CH₂ |
| O | CH₃ | CF₃ | Cl | F | H | CH₂C≡N |
| O | CH₃ | CF₃ | Cl | F | H | CH₂CH₃ |
| O | CH₃ | CF₃ | Cl | F | H | CH₂CH₂CH₃ |
| O | CH₃ | CF₃ | CH₃ | F | H | CH(CH₃)C≡CH |
| O | CH₃ | CF₃ | CH₃ | F | H | CH₂CH=CH₂ |
| O | CH₃ | CF₃ | CH₃ | F | H | CH₂C≡N |
| O | CH₃ | CF₃ | CH₃ | F | H | CH₂CH₃ |
| O | CH₃ | CF₃ | CH₃ | F | H | CH₂CH₂CH₃ |
| S | CH₃ | CF₃ | H | F | H | CH₂C≡CH |
| S | CH₃ | CF₃ | H | F | H | CH(CH₃)C≡CH |
| S | CH₃ | CF₃ | H | F | H | CH₂CH=CH₂ |
| S | CH₃ | CF₃ | H | F | H | CH₂C≡N |
| S | CH₃ | CF₃ | H | F | H | CH₂CH₃ |
| S | CH₃ | CF₃ | H | F | H | CH₂CH₂CH₃ |
| S | CH₃ | CF₃ | H | H | H | CH₂C≡CH |
| O | CH₃ | CF₃ | H | F | CH₃ | CH₂C≡CH |
| S | CH₃ | CF₃ | H | F | CH₃ | CH₂C≡CH |
| S | CH₃ | CF₃ | CH₃ | F | H | CH₂C≡CH |
| O | CH₃ | CF₃ | H | F | H | CH₂OCH₃ |
| O | CH₃ | CF₃ | H | F | H | CH₂OCH₂CH₃ |
| O | CH₃ | CF₃ | H | F | H | CH₂CH₂OCH₃ |
| O | CH₃ | CF₃ | H | F | H | o-CH₃-benzyl |
| O | CH₃ | CF₃ | H | F | H | m-CH₃-benzyl |
| O | CH₃ | CF₃ | H | F | H | p-CH₃-benzyl |
| O | CH₃ | CF₃ | H | H | H | o-CH₃-benzyl |
| O | CH₃ | CF₃ | H | H | H | m-CH₃-benzyl |
| O | CH₃ | CF₃ | H | H | H | p-CH₃-benzyl |
| O | CH₃ | CF₃ | H | F | H | o-CH₃O-benzyl |
| O | CH₃ | CF₃ | H | F | H | m-CH₃O-benzyl |
| O | CH₃ | CF₃ | H | F | H | p-CH₃O-benzyl |
| O | CH₃ | CF₃ | H | F | H | CH₂-(2-pyridyl) |
| O | CH₃ | CF₃ | H | F | H | CH₂-(3-chloro-2-pyridyl) |
| O | CH₃ | CF₃ | H | F | H | CH₂-(3-methyl-2-pyridyl) |
| O | CH₃ | CF₃ | H | F | H | CH₂-(pyrazinyl) |

TABLE 3-A-2-continued

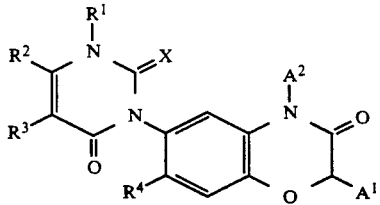

| X | R¹ | R² | R³ | R⁴ | A¹ | A² |
|---|----|----|----|----|----|----|
| O | CH₃ | CF₃ | H | F | H | CH₂-isothiazole |
| O | CH₃ | CF₃ | H | F | H | CH₂-isoxazole |
| O | CH₃ | CF₃ | H | F | H | o-CF₃-benzyl |
| O | CH₃ | CF₃ | H | F | H | m-CF₃-benzyl |
| O | CH₃ | CF₃ | H | F | H | p-CF₃-benzyl |
| O | CH₃ | CF₃ | H | F | H | CH₂-cyclopropyl |
| O | CH₃ | CF₃ | H | F | H | CH₂-cyclobutyl |
| O | CH₃ | CF₃ | H | F | H | CH₂-cyclopentyl |
| O | CH₃ | CF₃ | H | F | H | CH₂-cyclohexyl |
| O | CH₃ | CF₃ | H | F | H | CH₂CH₂-cyclopropyl |
| O | CH₃ | CF₃ | H | F | H | CH(CH₃)-cyclopropyl |
| O | CH₃ | CF₃ | H | F | H | CH(CH₃)-cyclobutyl |
| O | CH₃ | CF₃ | H | F | H | CH(CH₃)-cyclopentyl |
| O | CH₃ | CF₃ | Cl | F | H | CH(CH₃)-cyclopentyl |
| O | CH₃ | CF₃ | H | F | H | CH(CH₃)-cyclopentyl |
| O | CH₃ | CF₃ | H | F | H | CH(CH₃)-cyclohexyl |

TABLE 3-A-2-continued

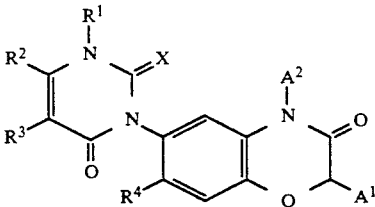

| X | R¹ | R² | R³ | R⁴ | A¹ | A² |
|---|----|----|----|----|----|----|
| O | CH₃ | CF₃ | H | F | H | CH₂CH₂-cyclobutyl |
| O | CH₃ | CF₃ | H | F | H | CH₂CH₂-cyclopentyl |
| O | CH₃ | CF₃ | H | F | H | CH₂CH₂-cyclohexyl |
| O | CH₃ | CF₃ | H | F | H | C₆H₅ |
| O | CH₃ | CF₃ | H | F | H | o-CH₃-phenyl |
| O | CH₃ | CF₃ | H | F | H | m-CH₃-phenyl |
| O | CH₃ | CF₃ | H | F | H | p-CH₃-phenyl |
| O | CH₃ | CF₃ | H | F | H | o-CH₃O-phenyl |
| O | CH₃ | CF₃ | H | F | H | m-CH₃O-phenyl |
| O | CH₃ | CF₃ | H | F | H | p-CH₃O-phenyl |
| O | CH₃ | CF₃ | H | F | H | o-Cl-phenyl |
| O | CH₃ | CF₃ | H | F | H | m-Cl-phenyl |
| O | CH₃ | CF₃ | H | F | H | p-Cl-phenyl |
| O | CH₃ | CF₃ | H | F | H | o-CF₃-phenyl |
| O | CH₃ | CF₃ | H | F | H | m-CF₃-phenyl |
| O | CH₃ | CF₃ | H | F | H | p-CF₃-phenyl |
| O | CH₃ | CF₃CF₂ | H | F | H | H |
| O | CH₃ | CF₃CF₂ | H | F | H | CH₃ |
| O | CH₃ | CF₃CF₂ | H | F | H | CH₂CH₃ |
| O | CH₃ | CF₃CF₂ | H | F | H | CH₂CH₂CH₃ |
| O | CH₃ | CF₃CF₂ | H | F | H | CH₂CH=CH₂ |
| O | CH₃ | CF₃CF₂ | H | F | H | CH₂C≡CH |
| O | CH₃ | CF₃CF₂ | H | F | H | CH(CH₃)C≡CH |
| O | CH₃ | CF₃CF₂ | H | F | H | C₆H₅ |
| O | CH₃ | CF₃CF₂ | H | F | H | C₁₀H₇ |
| S | CH₃ | CF₃CF₂ | H | F | H | CH₂C≡CH |
| O | CH₃ | CF₃CF₂ | Cl | F | H | CH₂C≡CH |
| O | CH₃ | CF₃CF₂ | CH₃ | F | H | CH₂C≡CH |
| O | CH₃ | CF₃CF₂ | H | H | H | CH₂C≡CH |
| O | CH₃ | CF₃CF₂ | H | F | CH₃ | CH₂C≡CH |
| O | CH₃ | CF₃CH₂ | H | F | H | H |
| O | CH₃ | CF₃CH₂ | H | F | H | CH₂CH₃ |
| O | CH₃ | CF₃CH₂ | H | F | H | CH₂CH₂CH₃ |
| O | CH₃ | CF₃CH₂ | H | F | H | CH₂CH=CH₂ |
| O | CH₃ | CF₃CH₂ | H | F | H | CH₂C≡CH |
| O | CH₃ | CF₃CF₂CF₂ | H | F | H | H |
| O | CH₃ | CF₃CF₂CF₂ | H | F | H | CH₂CH₃ |
| O | CH₃ | CF₃CF₂CF₂ | H | F | H | CH₂CH₂CH₃ |
| O | CH₃ | CF₃CF₂CF₂ | H | F | H | CH₂CH=CH₂ |
| O | CH₃ | CF₃CF₂CF₂ | H | F | H | CH₂C≡CH |
| O | CH₃ | (CF₃)₂CF | H | F | H | CH₂CH₃ |
| O | CH₃ | (CF₃)₂CF | H | F | H | CH₂C≡CH |
| O | CH₃ | CCl₃ | H | F | H | H |
| O | CH₃ | CCl₃ | H | F | H | CH₂C≡CH |
| S | CH₃ | CF₃ | H | F | H | H |
| S | CH₃ | CF₃ | H | F | CH₃ | H |
| S | CH₃ | CF₃ | CH₃ | F | H | H |
| S | CH₃ | CF₃ | H | H | H | H |
| S | CH₃ | CF₃ | H | H | CH₃ | H |
| S | CH₃ | CF₃ | CH₃ | H | H | H |
| O | CH₃ | CF₃ | H | Cl | H | CH₂C≡CH |
| O | CH₃ | CF₃ | H | Br | H | CH₂C≡CH |
| O | CH₂CH₃ | CF₃ | H | F | H | CH₂C≡CH |
| O | CH₃ | HCF₂ | H | F | H | H |
| O | CH₃ | HCF₂ | H | H | H | CH₂C≡CH |
| O | CH₃ | HCF₂ | H | F | H | CH₂C≡CH |

TABLE 3-A-2-continued

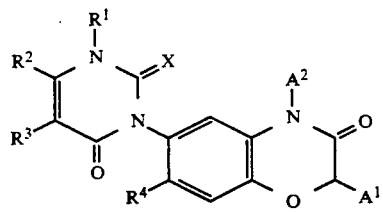

| X | R¹ | R² | R³ | R⁴ | A¹ | A² |
|---|---|---|---|---|---|---|
| O | CH₃ | HCF₂ | H | F | H | CH₂CH₃ |
| O | CH₃ | HCF₂ | H | F | H | CH₂CH₂CH₃ |
| O | H | CF₃ | H | H | H | o-CH₃-benzyl |
| O | H | CF₃ | H | H | H | m-CH₃-benzyl |
| O | H | CF₃ | H | H | H | p-CH₃-benzyl |
| O | H | CF₃ | H | F | H | CH₂OCH₃ |
| O | H | CH₃ | CH₃ | F | H | CH₂C≡CH |
| O | H | CF₃CF₂ | H | F | H | CH₂C≡CH |
| O | H | CF₃ | H | F | CH₃ | CH₂C≡CH |
| O | H | CF₃CH₂ | H | F | H | CH₂C≡CH |
| O | CH₃ | (CF₃)₂CH | H | F | H | CH₂C≡CH |

TABLE 3-B-1

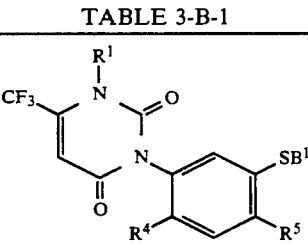

| R¹ | R⁴ | R⁵ | B¹ |
|---|---|---|---|
| CH₃ | F | Cl | CH₂CO₂H |
| CH₃ | F | Cl | CH₂CO₂Na |
| CH₃ | F | Cl | CH₂CO₂CH₃ |
| CH₃ | F | Cl | CH₂CO₂C₂H₅ |
| CH₃ | F | Cl | CH₂CO₂CH(CH₃)₂ |
| CH₃ | F | Cl | CH₂CO₂CH₂CH₂CH₃ |
| CH₃ | F | Cl | CH₂CO₂CH₂(CH₂)₂CH₃ |
| CH₃ | F | Cl | CH₂CO₂CH₂(CH₂)₃CH₃ |
| CH₃ | F | Cl | 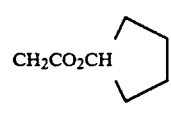 |
| CH₃ | F | Cl | 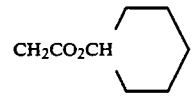 |
| CH₃ | F | Cl | CH(CH₃)CO₂CH₃ |
| CH₃ | F | Cl | CH(CH₃)CO₂C₂H₅ |
| CH₃ | H | Cl | CH₂CO₂CH₃ |
| CH₃ | H | Cl | CH(CH₃)CO₂CH₃ |
| CH₃ | F | NO₂ | CH₂CO₂CH₃ |
| CH₃ | F | Br | CH₂CO₂CH₃ |
| H | F | Cl | CH₂CO₂CH₃ |
| H | F | Cl | CH(CH₃)CO₂CH₃ |
| H | H | Cl | CH₂CO₂CH₃ |
| H | H | Cl | CH(CH₃)CO₂CH₃ |
| C₂H₅ | F | Cl | CH₂C≡CH |
| CH₂OH | F | Cl | CH₃ |
| CH₂Cl | F | Cl | C₂H₅ |
| CH₂Br | F | Cl | CH(CH₃)₂ |
| CH₂I | F | Cl | CH(CH₃)₂ |
| CH₃ | F | Cl | CH(CH₃)₂ |
| CH₃ | F | Cl | CH₂C≡CH |
| CH₃ | F | Cl | CH₂C₆H₅ |
| CH₃ | F | Cl | CH₂OH |
| CH₃ | F | Cl | CH₂Cl |
| CH₃ | F | Cl | CH₂CN |

TABLE 3-B-1-continued

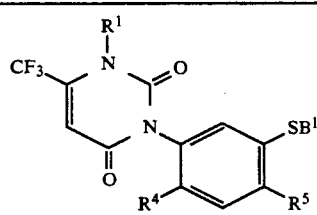

| R¹ | R⁴ | R⁵ | B¹ |
|---|---|---|---|
| CH₃ | F | Cl |  |
| CH₃ | F | Cl | 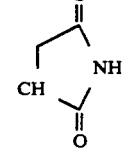 |
| CH₃ | F | Cl | 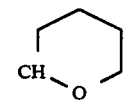 |
| CH₃ | F | Cl | CH(SCH₃)CO₂CH₃ |
| CH₃ | F | Cl | CH(SC₆H₅)CO₂CH₃ |
| CH₃ | F | Cl | CH(CH₂OCH₃)CO₂CH₃ |
| CH₃ | F | Cl | CH(CH₂OCH₃)CO₂C₂H₅ |
| CH₃ | F | Cl | CH₂CO₂C₆H₅ |
| CH₃ | F | Cl | CH₂CO₂CH₂C₆H₅ |
| CH₃ | F | Cl | CH₂CO₂CH₂CH₂CH₂N(CH₃)₂ |
| CH₃ | F | Cl | CH₂CO₂-(2-Cl-benzyl) |
| CH₃ | F | Cl | CH₂CO₂-(2-F-benzyl) |
| CH₃ | F | Cl | CH₂CH₂CO₂CH₃ |
| CH₃ | F | Cl | (CH₂)₃CO₂CH₃ |
| CH₃ | F | Cl | (CH₂)₄CO₂CH₃ |
| CH₃ | F | Cl | (CH₂)₅CO₂CH₃ |
| CH₃ | F | Cl | CH₂OCH₃ |
| CH₃ | F | Cl | CH₂OCH₂CN |
| CH₃ | F | Cl | CH₂OCOCH₃ |
| CH₃ | F | Cl | CH₂OCH₂CO₂CH₃ |
| CH₃ | F | Cl | CH₂OCH(CH₃)CO₂CH₃ |
| CH₃ | F | Cl | CH₂SCH₂CO₂CH₃ |
| CH₃ | F | Cl | CH₂SCH₂CH₂CO₂CH₃ |
| CH₃ | F | Cl | CH₂OCH₂CH₂CO₂CH₃ |

TABLE 3-B-1-continued

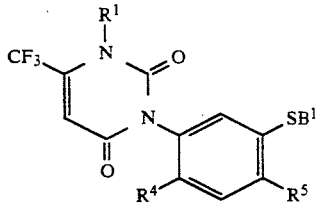

| R¹ | R⁴ | R⁵ | B¹ |
|---|---|---|---|
| CH₃ | H | Cl | CH₂CO₂CH₂CH₃ |
| CH₃ | H | Cl | CH(CH₃)CO₂CH₂CH₃ |
| H | F | Cl | H |
| H | F | Cl | CH₃ |
| CH₃ | F | Cl | CH(CH₃)CO₂H |
| H | F | Cl | CH(CH₂OCH₃)CO₂CH₃ |
| H | F | Cl | CH(CH₂OCH₃)CO₂CH₂CH₃ |

TABLE 3-B-2

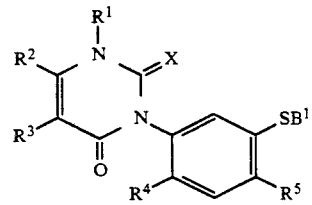

| X | R¹ | R² | R³ | R⁴ | R⁵ | B¹ |
|---|---|---|---|---|---|---|
| S | CH₃ | CF₃ | H | F | Cl | CH₂CO₂CH₃ |
| S | CH₃ | CF₃ | H | F | Cl | CH₂CO₂CH₂CH₃ |
| S | CH₃ | CF₃ | H | F | Cl | CH(CH₃)CO₂CH₃ |
| S | CH₃ | CF₃ | H | F | Cl | CH(CH₃)CO₂CH₂CH₃ |
| S | CH₃ | CF₃ | H | F | Cl | CH₃ |
| O | CH₃ | CF₃ | CH₃ | F | Cl | CH₂CO₂CH₃ |
| O | CH₃ | CF₃ | CH₃ | F | Cl | CH₂CO₂CH₂CH₃ |
| O | CH₃ | CF₃ | CH₃ | F | Cl | CH(CH₃)CO₂CH₃ |
| O | CH₃ | CF₃ | CH₃ | F | Cl | CH(CH₃)CO₂CH₂CH₃ |
| O | CH₃ | CF₃ | CH₃ | F | Cl | CH₃ |
| O | CH₃ | CF₃ | Cl | F | Cl | CH₂CO₂CH₃ |
| O | CH₃ | CF₃ | Cl | F | Cl | CH(CH₃)CO₂CH₂CH₃ |
| O | CH₃ | CF₃ | Br | F | Cl | CH₂CO₂CH₃ |
| O | CH₃ | CF₃ | Br | F | Cl | CH(CH₃)CO₂CH₂CH₃ |
| O | CH₃ | CF₃ | F | F | Cl | CH₂CO₂CH₃ |
| O | CH₃ | CF₃ | F | F | Cl | CH(CH₃)CO₂CH₂CH₃ |
| O | CH₃ | CF₃ | NO₂ | F | Cl | CH₂CO₂CH₃ |
| O | CH₃ | CF₃ | NO₂ | F | Cl | CH(CH₃)CO₂CH₂CH₃ |
| O | CH₃ | CF₃ | HOCH₂ | F | Cl | CH₂CO₂CH₃ |
| O | CH₃ | CF₃ | HOCH₂ | F | Cl | CH(CH₃)CO₂CH₂CH₃ |
| O | CH₃ | CF₃ | CH₂CH₃ | F | Cl | CH₂CO₂CH₃ |
| O | CH₃ | CF₃ | CH₂CH₃ | F | Cl | CH(CH₃)CO₂CH₂CH₃ |
| O | CH₃ | CF₃ | CF₃ | F | Cl | CH₂CO₂CH₃ |
| O | CH₃ | CF₃ | CF₃ | F | Cl | CH(CH₃)CO₂CH₂CH₃ |
| O | CH₃ | CF₃ | H | F | CN | CH₃ |
| O | CH₃ | CF₃ | H | F | CN | CH₂CO₂CH₃ |
| O | CH₃ | CF₃ | H | F | CN | CH(CH₃)CO₂CH₂CH₃ |
| O | CH₃ | CF₃CF₂ | H | F | Cl | CH₃ |
| O | CH₃ | CF₃CF₂ | H | F | Cl | CH(CH₃)₂ |
| O | CH₃ | CF₃CF₂ | H | F | Cl | CH₂CO₂CH₃ |
| O | CH₃ | CF₃CF₂ | H | F | Cl | CH₂CO₂CH₂CH₃ |
| O | CH₃ | CF₃CF₂ | H | F | Cl | CH(CH₃)CO₂CH₃ |
| O | CH₃ | CF₃CF₂ | H | F | Cl | CH(CH₃)CO₂CH₂CH₃ |
| O | CH₃ | CF₃CF₂ | H | F | Cl | CH(CH₂CH₃)CO₂CH₃ |
| O | CH₃ | CF₃CF₂ | H | F | Cl | CH(CH₂CH₃)CO₂CH₂CH₃ |
| O | CH₃ | CF₃CF₂ | H | F | Cl | CH₂CO₂CH⟨ |
| O | CH₃ | CF₃CF₂ | H | F | Cl | CH₂CN |
| O | CH₃ | CF₃CF₂ | H | F | Cl | CH₂OCH₃ |
| O | CH₃ | CF₃CF₃CF₂ | H | F | Cl | CH₃ |
| O | CH₃ | CF₃CF₃CF₂ | H | F | Cl | CH₂CO₂CH₃ |
| O | CH₃ | CF₃CF₃CF₂ | H | F | Cl | CH(CH₃)CO₂CH₂CH₃ |
| O | CH₃ | (CF₃)₂CF | H | F | Cl | CH₃ |
| O | CH₃ | (CF₃)₂CF | H | F | Cl | CH₂CO₂CH₃ |
| O | CH₃ | (CF₃)₂CF | H | F | Cl | CH(CH₃)CO₂CH₂CH₃ |
| O | CH₃ | CF₃CH₂ | H | F | Cl | CH₃ |
| O | CH₃ | CF₃CH₂ | H | F | Cl | CH₂CO₂CH₃ |
| O | CH₃ | CF₃CH₂ | H | F | Cl | CH(CH₃)CO₂CH₂CH₃ |
| O | CH₃ | CCl₃ | H | F | Cl | CH₃ |
| O | CH₃ | CCl₃ | H | F | Cl | CH₂CO₂CH₃ |
| O | CH₃ | CCl₃ | H | F | Cl | CH(CH₃)CO₂CH₂CH₃ |
| O | CH₃ | HCF₂ | H | F | Cl | CH₂CO₂CH₃ |

TABLE 3-C-1

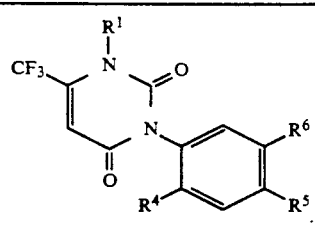

| R¹ | R⁴ | R⁵ | R⁶ |
|---|---|---|---|
| $CH_3$ | F | Cl | $CHNOCH_2CO_2CH_3$ |
| $CH_3$ | F | Cl | $C(CH_3)NOCH_2CO_2C_2H_5$ |
| $CH_3$ | F | Cl | $C(CH_2OCH_3)NOCH_2CO_2CH_3$ |
| $CH_3$ | F | Cl | $C(OCH_3)NOCH_2CO_2C_2H_5$ |
| $CH_3$ | H | Cl | $C(CH_3)NOCH_2CO_2C_2H_5$ |
| $CH_3$ | H | Cl | $C(CH_2OCH_3)NOCH_2CO_2CH_3$ |
| H | F | Cl | $C(CH_3)NOCH_2CO_2C_2H_5$ |
| H | H | Cl | $C(CH_3)NOCH_2CO_2C_2H_5$ |
| $CH_3$ | F | Cl | $C(CH_3)NNC(CH_3)CO_2CH_3$ |
| $CH_3$ | F | Cl | $C(OCH_3)NNC(CH_3)CO_2CH_3$ |
| $CH_3$ | F | Cl | $C(OCH_3)NNCHCO_2C_2H_5$ |
| $CH_3$ | H | Cl | $C(CH_3)NNC(CH_3)CO_2CH_3$ |
| H | F | Cl | $C(CH_3)NNC(CH_3)CO_2CH_3$ |
| H | H | Cl | $C(CH_3)NNC(CH_3)CO_2CH_3$ |
| $CH_3$ | F | Cl | $CH_2OCH_2CO_2C_2H_5$ |
| $CH_3$ | F | Cl | $CH_2OCH(CH_3)CO_2C_2H_5$ |
| $CH_3$ | F | Cl | $CH_2OCH(CH_2OCH_3)CO_2CH_3$ |
| $CH_3$ | F | Cl | $CH_2SCH_2CO_2CH_3$ |
| $CH_3$ | F | Cl | $CH_2SCH(CH_3)CO_2C_2H_5$ |
| $CH_3$ | F | Cl | $CH_2NHCH_2CO_2CH_3$ |
| $CH_3$ | F | Cl | $CH_2NHCH(CH_3)CO_2C_2H_5$ |
| $CH_3$ | F | Cl | $CH_2NHCH(CH_2OCH_3)CO_2C_2H_5$ |
| $CH_3$ | H | Cl | $CH_2OCH_2CO_2C_2H_5$ |
| $CH_3$ | H | Cl | $CH_2SCH(CH_3)CO_2C_2H_5$ |
| $CH_3$ | H | Cl | $CH_2NHCH_2CO_2CH_3$ |
| H | F | Cl | $CH_2OCH_2CO_2C_2H_5$ |
| H | H | Cl | $CH_2NHCH_2CO_2CH_3$ |
| $CH_3$ | F | Cl | $NHSO_2CH_3$ |
| $CH_3$ | F | Cl | $NHSO_2C_2H_5$ |
| $CH_3$ | F | Cl | $NHSO_2CH_2CH_2CH_3$ |
| $CH_3$ | F | Cl | $N(SO_2CH_3)_2$ |
| $CH_3$ | F | Cl | $N(SO_2C_2H_5)_2$ |
| $CH_3$ | F | Cl | $N(SO_2CH_2CH_2CH_3)_2$ |
| $CH_3$ | F | Cl | $N(SO_2CH_3)CH_3$ |
| $CH_3$ | F | Cl | $N(SO_2CH_3)C_4H_9^n$ |
| $CH_3$ | F | Cl | $N(SO_2CH_3)CH_2OCH_3$ |
| $CH_3$ | F | Cl | $N(SO_2C_2H_5)CH_2OCH_3$ |
| $CH_3$ | H | Cl | $N(SO_2C_2H_5)CH_2OCH_3$ |
| $CH_3$ | H | Cl | $N(SO_2CH_3)_2$ |
| H | F | Cl | $N(SO_2CH_3)_3$ |
| H | F | Cl | $N(SO_2C_2H_5)_3$ |
| H | H | Cl | $N(SO_2CH_3)_2$ |
| $CH_3$ | F | Cl | $C(CH_3)NOCH_2CO_2CH_3$ |
| $CH_3$ | F | Cl | $C(CH_2OCH_3)NOCH_2CO_2C_2H_5$ |
| $CH_3$ | F | Cl | $C(OCH_3)NOCH_2CO_2CH_3$ |
| $CH_3$ | H | Cl | $C(CH_3)NOCH_2CO_2CH_3$ |
| $CH_3$ | H | Cl | $C(CH_2OCH_3)NOCH_2CO_2C_2H_5$ |
| $CH_3$ | H | Cl | $C(OCH_3)NOCH_2CO_2CH_3$ |
| $CH_3$ | F | Cl | $CH_2OCH_2CO_2CH_3$ |
| $CH_3$ | F | Cl | $CH_2OCH(CH_3)CO_2CH_3$ |
| $CH_3$ | F | Cl | $CH_2SCH_2CO_2C_2H_5$ |
| $CH_3$ | F | Cl | $CH_2SCH(CH_3)CO_2CH_3$ |
| $CH_3$ | F | Cl | $CH_2NHCH_2CO_2C_2H_5$ |
| $CH_3$ | F | Cl | $CH_2NHCH(CH_3)CO_2CH_3$ |
| $CH_3$ | F | Cl | $N(CH_2CH{=}CH_2)SO_2CH_3$ |
| $CH_3$ | F | Cl | $N(CH_2CH{=}CH_2)SO_2C_2H_5$ |
| $CH_3$ | F | Cl | $N(CH_2C{\equiv}CH)SO_2CH_3$ |
| $CH_3$ | F | Cl | $N(CH_2C{\equiv}CH)SO_2C_2H_5$ |
| $CH_3$ | F | Cl | $N(COCH_3)SO_2CH_3$ |
| $CH_3$ | F | Cl | $N(COC_2H_5)SO_2CH_3$ |
| $CH_3$ | F | Cl | $NHSO_2CH_2CH_2CH_2CH_3$ |
| $CH_3$ | F | Cl | $NHSO_2CH_2CH(CH_3)_2$ |
| $CH_3$ | F | Cl | $NHSO_2CH(CH_3)CH_2CH_3$ |
| $CH_3$ | F | Cl | $NHSO_2C(CH_3)_3$ |
| $CH_3$ | F | Cl | $NHSO_2CF_3$ |
| $CH_3$ | F | Cl | $N(SO_2CF_3)_2$ |

TABLE 3-C-1-continued

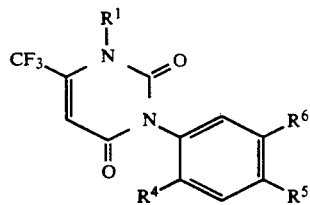

| R¹ | R⁴ | R⁵ | R⁶ |
|---|---|---|---|
| $CH_3$ | F | Cl | (N—N heterocycle with $CH_3$) |
| $CH_3$ | F | Cl | (N—N heterocycle with $C_2H_5$) |
| $CH_3$ | F | Cl | (N—N heterocycle with $CH_2CH_2CH_3$) |
| $CH_3$ | F | Cl | (N—N heterocycle with $CH(CH_3)_2$) |
| $CH_3$ | F | Cl | (N—N heterocycle with $(CH_2)_3CH_3$) |
| $CH_3$ | F | Cl | (N—N heterocycle with $C(CH_3)_3$) |
| $CH_3$ | F | Cl | (N—N heterocycle with $C(C_2H_5)_2CH_3$) |
| $CH_3$ | F | Cl | (N—N heterocycle with $OC_2H_5$) |
| $CH_3$ | F | Cl | (N—N heterocycle with cyclopentyl, H) |
| $CH_3$ | F | Cl | (N—N heterocycle with $CH_2OCH_3$) |
| $CH_3$ | F | Cl | (N—N heterocycle with H) |
| H | F | Cl | (N—N heterocycle with $CH_3$) |
| H | F | Cl | (N—N heterocycle with $C(CH_3)_3$) |

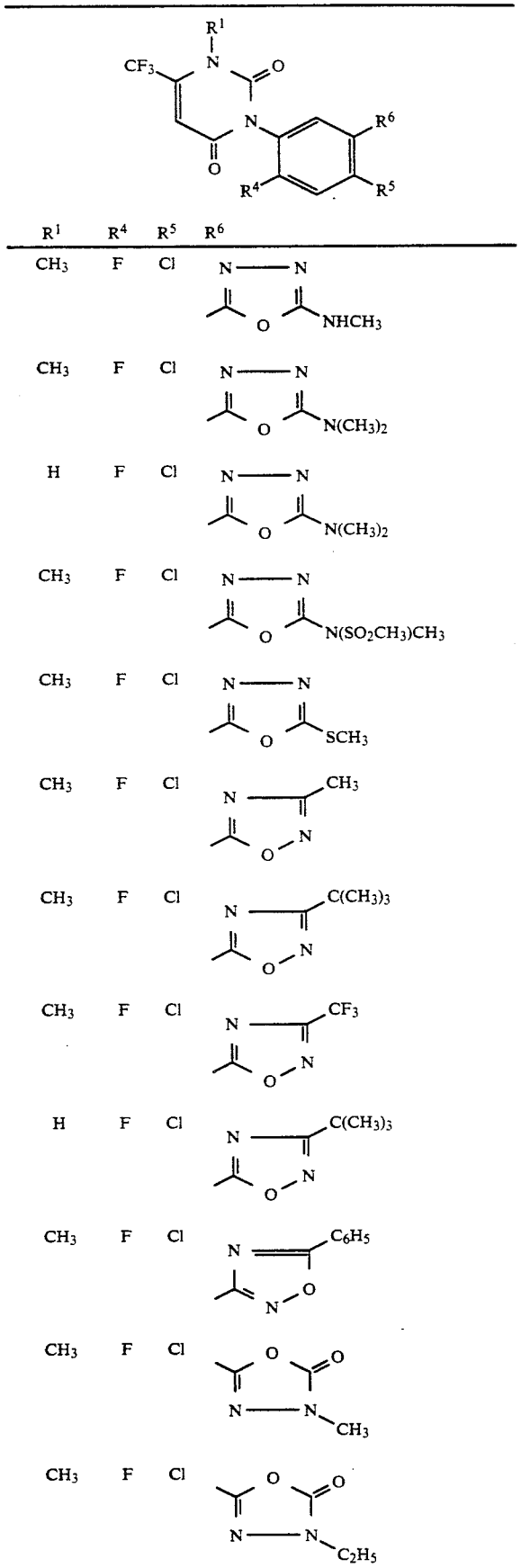
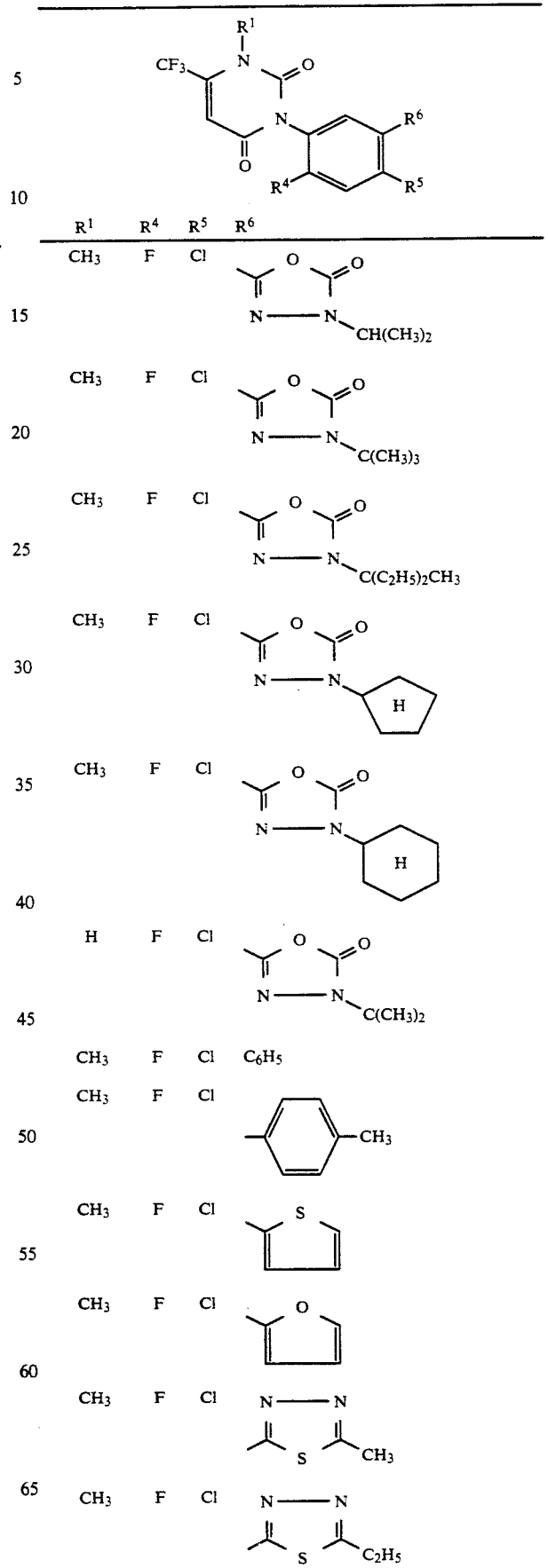

TABLE 3-C-1-continued
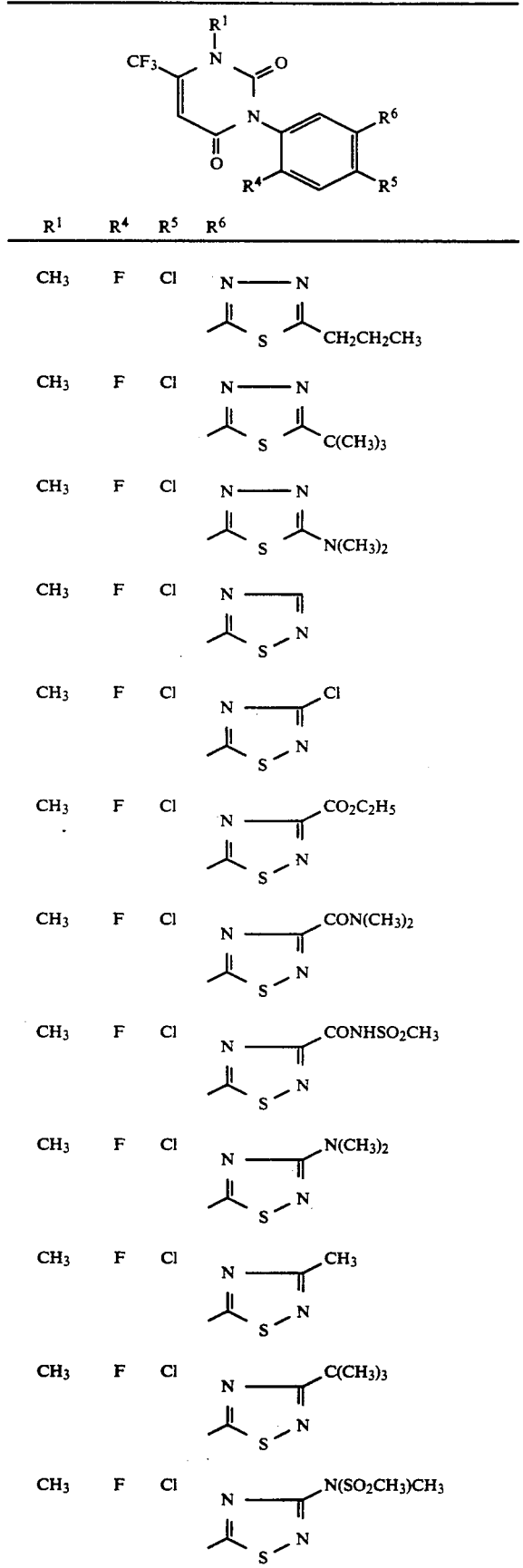
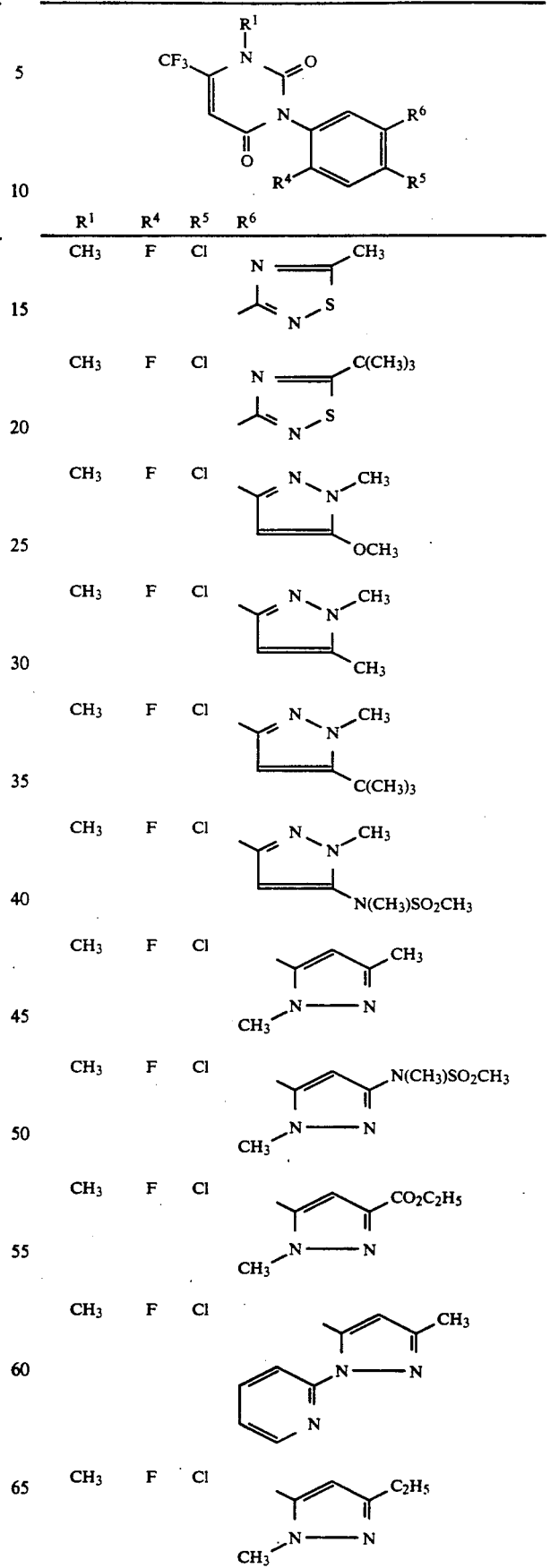

TABLE 3-C-1-continued
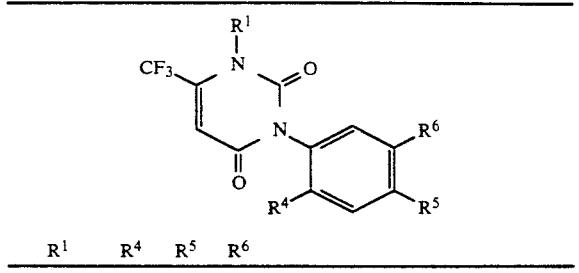
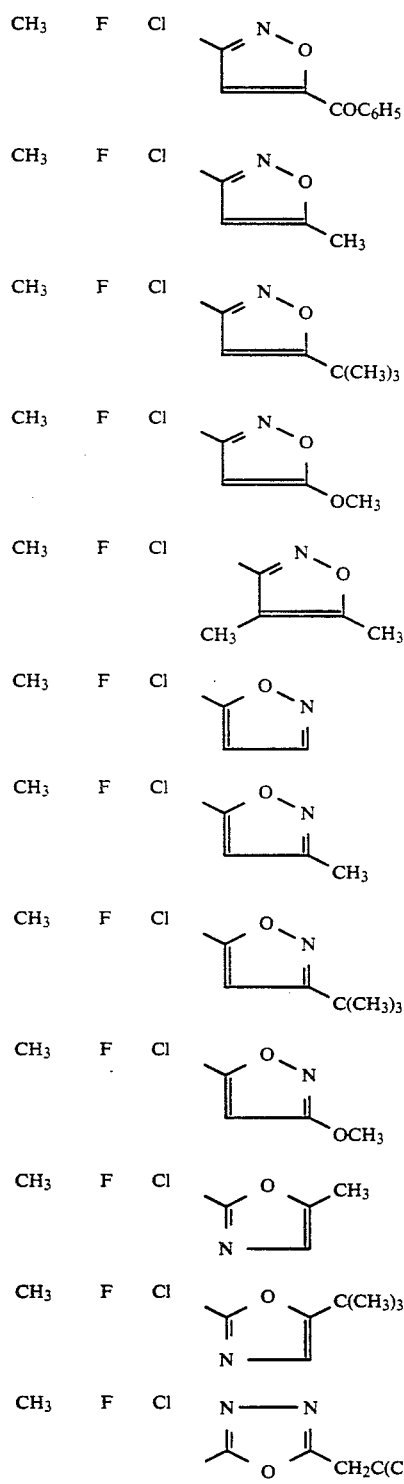
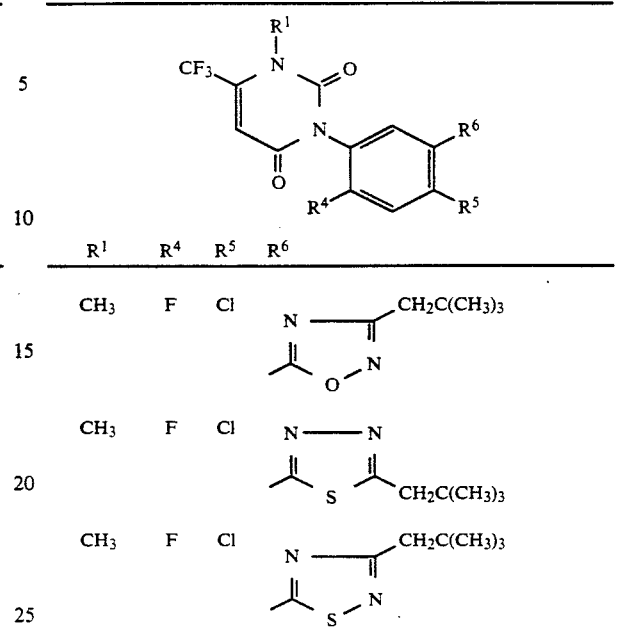
TABLE 3-C-2
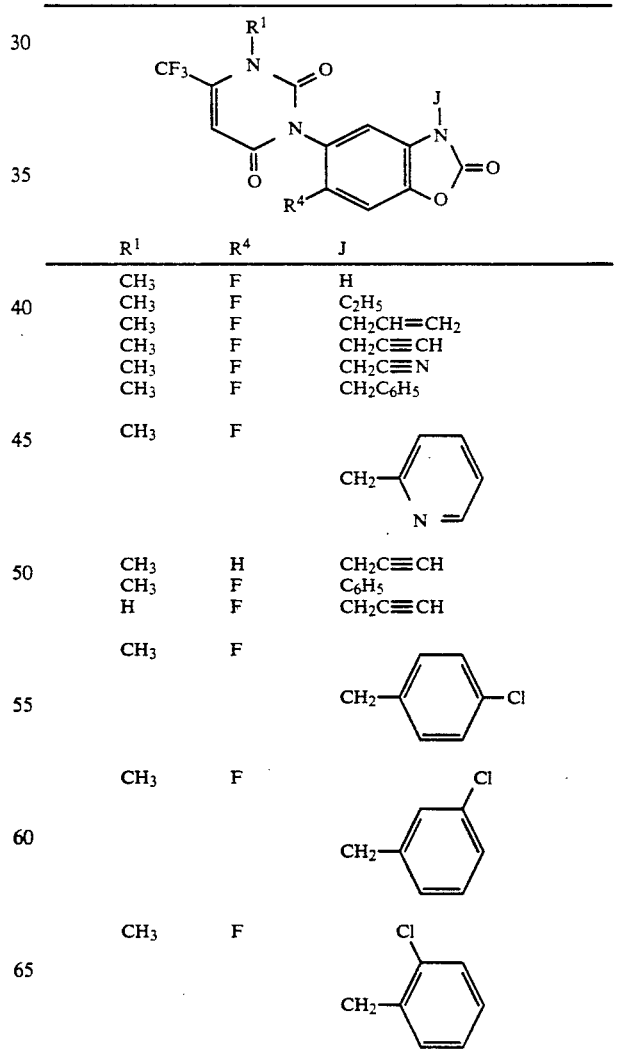
| R¹ | R⁴ | J |
|---|---|---|
| CH₃ | F | H |
| CH₃ | F | C₂H₅ |
| CH₃ | F | CH₂CH=CH₂ |
| CH₃ | F | CH₂C≡CH |
| CH₃ | F | CH₂C≡N |
| CH₃ | F | CH₂C₆H₅ |
| CH₃ | H | CH₂C≡CH |
| CH₃ | F | C₆H₅ |
| H | F | CH₂C≡CH |

TABLE 3-C-2-continued

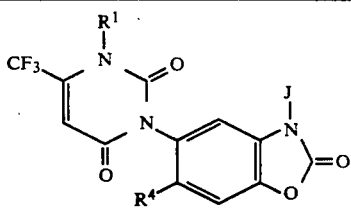

| R¹ | R⁴ | J |
|---|---|---|
| CH₃ | F | CH₂OCH₃ |
| CH₃ | Cl | CH₂C≡CH |
| CH₃ | F | CH₂CH₂CH₃ |
| CH₃ | F | CH(CH₃)C≡CH |
| CH₃ | F | CH₂OCH₂CH₃ |
| CH₃ | F | CH₂CONH₂ |
| CH₃ | F | CH₂CO₂CH₃ |
| CH₃ | F | CH₂CO₂CH₂CH₃ |
| CH₃ | F | CH(CH₃)CH=CH₂ |

TABLE 3-C-3

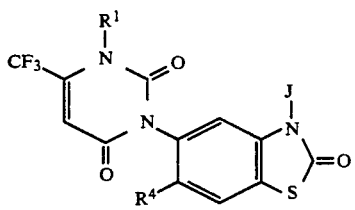

| R¹ | R⁴ | J |
|---|---|---|
| CH₃ | F | H |
| CH₃ | F | CH₃ |
| CH₃ | F | C₂H₅ |
| CH₃ | F | CH₂CH₂CH₃ |
| CH₃ | F | CH₂CH=CH₂ |
| CH₃ | F | CH₂C≡CH |
| CH₃ | F | CH₂C≡CCH₃ |
| CH₃ | F | CH₂C≡N |
| CH₃ | F | CH₂OH |
| CH₃ | F | CH₂Cl |
| CH₃ | F | CH₂CO₂CH₃ |
| CH₃ | F | CH₂CO₂C₂H₅ |
| CH₃ | F | CH₂OCH₃ |
| CH₃ | F | C₆H₅ |
| CH₃ | F | CH₂C₆H₅ |
| CH₃ | F | 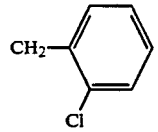 |
| CH₃ | F | 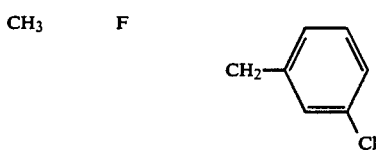 |
| CH₃ | F | 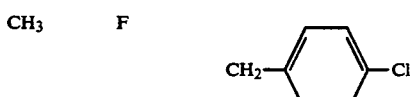 |
| CH₃ | F | 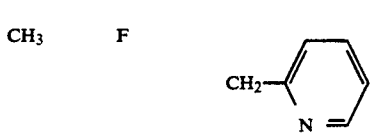 |

TABLE 3-C-3-continued

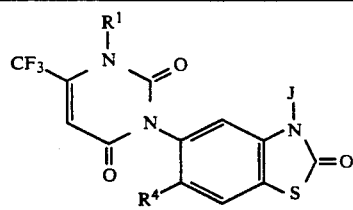

| R¹ | R⁴ | J |
|---|---|---|
| CH₃ | H | C₂H₅ |
| CH₃ | H | CH₂CH=CH₂ |
| CH₃ | H | CH₂C≡CH |
| CH₃ | H | CH₂OCH₃ |
| CH₃ | H | CH₂C₆H₅ |
| H | F | CH₂C≡CH |
| H | F | CH₂C₆H₅ |
| CH₃ | F | CH(CH₃)C≡CH |
| CH₃ | F | CH₂CH₂C≡CH |
| CH₃ | F | CH(CH₃)CH₂CH₃ |
| CH₃ | F | CH(CH₃)CH=CH₂ |
| CH₃ | F | CH₂OCH₂CH₃ |
| CH₃ | F | CH₂CH₂OCH₃ |
| CH₃ | F | CH(CH₃)OCH₃ |
| CH₃ | F | CH(CH₃)OCH₂CH₃ |
| CH₃ | F | o-CH₃-benzyl |
| CH₃ | F | m-CH₃-benzyl |
| CH₃ | F | p-CH₃-benzyl |
| CH₃ | F | o-CF₃-benzyl |
| CH₃ | F | m-CF₃-benzyl |
| CH₃ | F | p-CF₃-benzyl |
| CH₃ | F | o-CH₃-phenyl |
| CH₃ | F | m-CH₃-phenyl |
| CH₃ | F | p-CH₃-phenyl |
| CH₃ | F | o-Cl-phenyl |
| CH₃ | F | m-Cl-phenyl |
| CH₃ | F | p-Cl-phenyl |
| CH₃ | F | o-CF₃-phenyl |
| CH₃ | F | m-CF₃-phenyl |
| CH₃ | F | p-CF₃-phenyl |
| CH₃ | F | o-Cl-benzyl |
| CH₃ | F | m-Cl-benzyl |
| CH₃ | F | p-Cl-benzyl |
| H | F | H |

TABLE 3-C-4

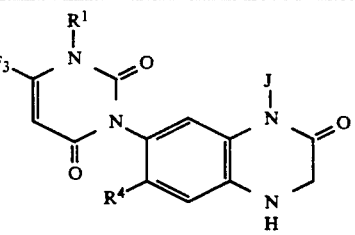

| R¹ | R⁴ | J |
|---|---|---|
| CH₃ | F | CH₃ |
| CH₃ | F | C₂H₅ |
| CH₃ | F | CH₂CH=CH₂ |
| CH₃ | F | CH₂C≡CH |
| CH₃ | F | CH₂C₆H₅ |
| CH₃ | F | H |
| CH₃ | F | C₆H₅ |
| CH₃ | F | CH₂C≡N |
| CH₃ | H | C₂H₅ |
| CH₃ | H | CH₂C≡CH |
| CH₃ | H | CH₂C₆H₅ |
| CH₃ | H | CH₂CH=CH₂ |
| CH₃ | F | 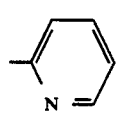 |

TABLE 3-C-4-continued

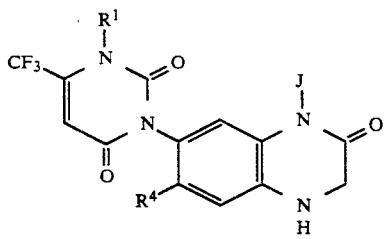

| R¹ | R⁴ | J |
|---|---|---|
| CH₃ | F | CH₂CO₂C₂H₅ |
| H | F | CH₂C≡CH |
| CH₃ | F | CH(CH₃)C≡CH |
| CH₃ | F | CH₂C≡CCH₃ |
| CH₃ | F | CH₂CH₂C≡CH |
| CH₃ | F | CH(CH₃)CH=CH₂ |
| CH₃ | F | CH₂CH₂CH₃ |
| CH₃ | F | CH(CH₃)CH₂CH₃ |
| CH₃ | F | o-CH₃-benzyl |
| CH₃ | F | m-CH₃-benzyl |
| CH₃ | F | p-CH₃-benzyl |
| CH₃ | F | o-Cl-benzyl |
| CH₃ | F | m-Cl-benzyl |
| CH₃ | F | p-Cl-benzyl |
| CH₃ | F | o-CH₃-phenyl |
| CH₃ | F | m-CH₃-phenyl |
| CH₃ | F | p-CH₃-phenyl |
| CH₃ | F | o-Cl-phenyl |
| CH₃ | F | m-Cl-phenyl |
| CH₃ | F | p-Cl-phenyl |
| CH₃ | F | CH₂OCH₃ |
| CH₃ | F | CH₂OCH₂CH₃ |
| CH₃ | F | CH(CH₃)OCH₃ |
| CH₃ | F | CH(CH₃)OCH₂CH₃ |
| H | F | H |
| H | H | H |
| H | F | CH(CH₃)C≡CH |
| H | F | CH₂C≡N |
| H | F | CH₂C₆H₅ |

TABLE 3-C-5

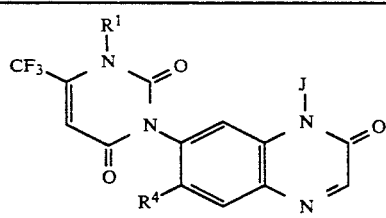

| R¹ | R⁴ | J |
|---|---|---|
| CH₃ | F | H |
| CH₃ | F | CH₃ |
| CH₃ | F | C₂H₅ |
| CH₃ | F | CH₂CH=CH₂ |
| CH₃ | F | CH₂C≡CH |
| CH₃ | F | CH₂C₆H₅ |
| CH₃ | F | CH₂C≡N |
| CH₃ | F | CH₂OCH₃ |
| CH₃ | H | CH₂C≡CH |
| CH₃ | H | CH₂C₆H₅ |
| H | F | CH₂C≡CH |
| H | H | CH₂C≡CH |
| CH₃ | H | C₂H₅ |
| H | H | C₂H₅ |
| H | F | C₂H₅ |
| CH₃ | F | CH₂CH₂CH₃ |
| CH₃ | F | CH(CH₃)C≡CH |
| CH₃ | F | CH(CH₃)CH=CH₂ |
| CH₃ | F | CH₂CO₂CH₃ |
| CH₃ | F | C₆H₅ |
| CH₃ | F | o-CH₃-benzyl |
| CH₃ | F | m-CH₃-benzyl |

TABLE 3-C-5-continued

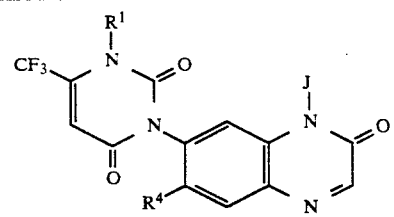

| R¹ | R⁴ | J |
|---|---|---|
| CH₃ | F | p-CH₃-benzyl |
| H | F | H |
| H | H | H |
| H | F | CH₂CH₂CH₃ |
| H | F | CH₂C₆H₅ |
| H | F | CH₂C≡N |

TABLE 3-C-6

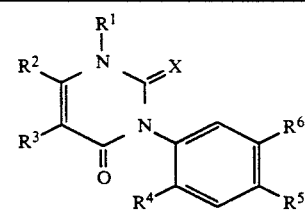

| X | R¹ | R² | R³ | R⁴ | R⁵ | R⁶ |
|---|---|---|---|---|---|---|
| S | CH₃ | CF₃ | H | F | Cl | C(CH₃)NOCH₂CO₂CH₂CH₃ |
| S | CH₃ | CF₃ | H | F | Cl | C(OCH₃)NOCH₂CO₂CH₂CH₃ |
| S | CH₃ | CF₃ | H | F | Cl | C(CH₃)NNCHCO₂CH₂CH₃ |
| S | CH₃ | CF₃ | H | F | Cl | CH₂OCH₂CO₂CH₂CH₃ |
| S | CH₃ | CF₃ | H | F | Cl | CH₂NHCH₂CO₂CH₂CH₃ |
| S | CH₃ | CF₃ | H | F | Cl | NHSO₂CH₃ |
| S | CH₃ | CF₃ | H | F | Cl | NHSO₂CH₂CH₃ |
| S | CH₃ | CF₃ | H | F | Cl | NHSO₂CH₂CH₂CH₃ |
| O | CH₃ | CF₃ | Cl | F | Cl | C(CH₃)NOCH₂CO₂CH₂CH₃ |
| O | CH₃ | CF₃ | CH₃ | F | Cl | C(CH₃)NOCH₂CO₂CH₂CH₃ |
| O | CH₃ | CF₃ | CH₃ | F | Cl | C(CH₂OCH₃)NOCH₂CO₂CH₂CH₃ |
| O | CH₃ | CF₃ | H | F | CN | C(CH₃)NOCH₂CO₂CH₂CH₃ |
| O | CH₃ | CF₃ | CH₃ | F | Cl | NHSO₂CH₂CH₃ |
| O | CH₃ | CF₃ | CH₃ | F | Cl | CH₂OCH₂CO₂CH₂CH₃ |
| O | CH₃ | CF₃CF₂ | H | F | Cl | C(CH₃)NOCH₂CO₂CH₂CH₃ |
| S | CH₃ | CF₃ | H | F | Cl | 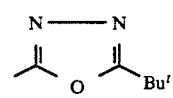 |
| S | CH₃ | CF₃ | H | F | Cl | 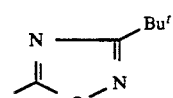 |
| S | CH₃ | CF₃ | H | F | Cl | 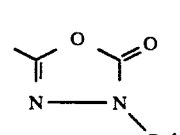 |
| S | CH₃ | CF₃ | H | F | Cl | 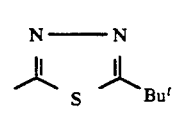 |
| S | CH₃ | CF₃ | H | F | Cl | 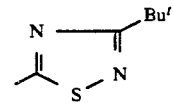 |

TABLE 3-C-6-continued

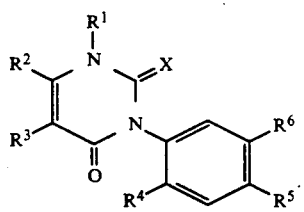

| X | R¹ | R² | R³ | R⁴ | R⁵ | R⁶ |
|---|---|---|---|---|---|---|
| O | CH₃ | CF₃CF₂ | H | F | Cl | (N—N with CH₃, O, Buᵗ) |
| O | CH₃ | CF₃CF₂ | H | F | Cl | (N with Buᵗ, O, N) |
| O | CH₃ | CF₃CF₂ | H | F | Cl | (O, N-Buᵗ, C=O) |
| O | CH₃ | CF₃CF₂ | H | F | Cl | (N—N with S, Buᵗ) |
| O | CH₃ | CF₃CF₂ | H | F | Cl | (N, Buᵗ, S, N) |

TABLE 3-C-7

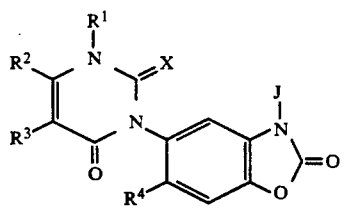

| X | R¹ | R² | R³ | R⁴ | J |
|---|---|---|---|---|---|
| S | CH₃ | CF₃ | H | F | CH₂C≡CH |
| S | CH₃ | CF₃ | H | F | CH₂CH₃ |
| S | CH₃ | CF₃ | H | F | CH₂CH=CH₂ |
| O | CH₃ | CF₃CF₂ | H | F | CH₂C≡CH |
| O | CH₃ | CF₃CF₂ | H | F | CH₂CH₃ |
| O | CH₃ | CF₃CF₂ | H | F | CH₂CH=CH₂ |
| O | CH₃ | CF₃ | Cl | F | CH₂C≡CH |
| O | CH₃ | CF₃ | CH₃ | F | CH₂C≡CH |
| O | CH₃ | CF₃ | CH₃ | F | CH₂CH₃ |
| O | CH₃ | CF₃ | H | F | CH(CH₃)C≡CH |

TABLE 3-C-8

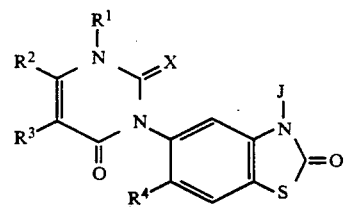

| X | R¹ | R² | R³ | R⁴ | J |
|---|---|---|---|---|---|
| S | CH₃ | CF₃ | H | F | CH₂C≡CH |
| S | CH₃ | CF₃ | H | F | CH₂CH₃ |
| S | CH₃ | CF₃ | H | F | CH₂CH₂CH₃ |
| S | CH₃ | CF₃ | H | F | CH(CH₃)C≡CH |
| S | CH₃ | CF₃ | H | F | CH₂OCH₃ |
| S | CH₃ | CF₃ | H | F | CH₂C₆H₅ |
| O | CH₃ | CF₃ | F | F | CH₂C≡CH |
| O | CH₃ | CF₃ | Cl | F | CH₂C≡CH |
| O | CH₃ | CF₃ | Br | F | CH₂C≡CH |
| O | CH₃ | CF₃ | I | F | CH₂C≡CH |
| O | CH₃ | CF₃ | CH₃ | F | CH₂C≡CH |
| O | CH₃ | CF₃ | CH₂CH₃ | F | CH₂C≡CH |
| O | CH₃ | CF₃CF₂ | H | F | CH₂C≡CH |
| O | CH₃ | CF₃CF₂ | H | F | CH(CH₃)C≡CH |
| O | CH₃ | CF₃CF₂ | H | F | CH₂CH=CH₂ |
| O | CH₃ | CF₃CF₂ | H | F | CH(CH₃)C≡CH |
| S | CH₃ | CF₃CF₂ | H | F | CH₂C≡CH |
| O | CH₃ | CF₃CF₂ | H | H | CH₂C≡CH |
| O | CH₃ | CF₃CF₂ | H | F | CH₂CH₂CH₃ |
| O | CH₃ | CF₃CH₂ | H | F | CH₂C≡CH |
| O | CH₃ | CF₃CH₂ | H | F | CH(CH₃)C≡CH |
| O | CH₃ | CF₃CH₂ | H | F | CH₂CH₃ |
| O | CH₃ | CF₃CH₂ | H | F | CH₂CH₂CH₃ |
| S | CH₃ | CF₃ | H | H | CH₂C≡CH |
| S | CH₃ | CF₃ | H | H | H |
| S | CH₃ | CF₃CF₂ | H | F | H |
| O | CH₃ | CCl₃ | H | F | CH₂C≡CH |
| O | CH₃ | HCF₂ | H | F | CH₂C≡CH |

TABLE 3-C-9

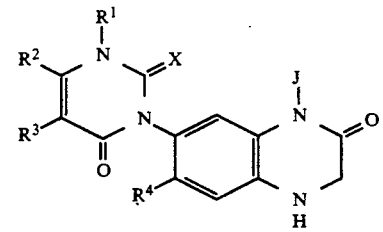

| X | R¹ | R² | R³ | R⁴ | J |
|---|---|---|---|---|---|
| S | CH₃ | CF₃ | H | F | CH₂C≡CH |
| S | CH₃ | CF₃ | H | F | CH(CH₃)C≡CH |
| S | CH₃ | CF₃ | H | F | CH₂CH₃ |
| S | CH₃ | CF₃ | H | F | CH₂CH₂CH₃ |
| S | CH₃ | CF₃ | H | F | CH₂CH=CH₂ |
| O | CH₃ | CF₃ | F | F | CH₂C≡CH |
| O | CH₃ | CF₃ | Cl | F | CH₂C≡CH |
| O | CH₃ | CF₃ | Br | F | CH₂C≡CH |
| O | CH₃ | CF₃ | CH₃ | F | CH₂C≡CH |
| O | CH₃ | CF₃ | CH₂CH₃ | F | CH₂C≡CH |
| O | CH₃ | CF₃ | CH(CH₃)₂ | F | CH₂C≡CH |
| O | CH₃ | CF₃CF₂ | H | F | H |
| O | CH₃ | CF₃CF₂ | H | F | CH₂C≡CH |
| S | CH₃ | CF₃ | H | H | H |
| S | CH₃ | CF₃ | H | H | CH₂C≡CH |
| O | CH₃ | HCF₂ | H | F | CH₂C≡CH |
| O | CH₃ | CCl₃ | H | F | CH₂C≡CH |
| O | CH₃ | CCl₃ | H | F | H |
| O | H | CCl₃ | H | F | CH₂C≡CH |

TABLE 3-C-10

[Structure: pyrimidine-type compound with substituents R¹, R², R³, R⁴, X, J on benzene ring system with N-containing heterocycles]

| X | R¹ | R² | R³ | R⁴ | J |
|---|----|----|----|----|----|
| S | CH$_3$ | CF$_3$ | H | F | H |
| S | CH$_3$ | CF$_3$ | H | F | CH$_2$C≡CH |
| S | CH$_3$ | CF$_3$ | H | F | CH$_2$CH$_3$ |
| S | CH$_3$ | CF$_3$ | H | F | CH$_2$CH$_2$CH$_3$ |
| O | CH$_3$ | CF$_3$ | F | F | CH$_2$C≡CH |
| O | CH$_3$ | CF$_3$ | Cl | F | CH$_2$C≡CH |
| O | CH$_3$ | CF$_3$ | Br | F | CH$_2$C≡CH |
| O | CH$_3$ | CF$_3$ | CH$_3$ | F | CH$_2$C≡CH |
| O | CH$_3$ | CF$_3$CF$_2$ | H | F | CH$_2$C≡CH |
| O | CH$_3$ | HCF$_2$ | H | F | CH$_2$C≡CH |
| O | CH$_3$ | CCl$_3$ | H | F | CH$_2$C≡CH |

Shown below are the examples of formulations using the compounds of the present invention. It should be understood, however, that the formulations coming within the concept of the present invention are not limited to those shown below. In the following descriptions of Formulation Examples, all "parts" are by weight unless otherwise noted.

| Formulation Example 1: Wettable powder | |
|---|---|
| Compound A-1 of the present invention | 50 parts |
| Zeeklite PFP (kaolin type clay, mfd. by Zeeklite Industries Co., Ltd.) | 43 parts |
| Sorpol 5050 (anionic surfactant, mfd. by Toho Chemical Co., Ltd.) | 2 parts |
| Runox 1000 C (anionic surfactant, mfd. by Toho Chemical Co., Ltd.) | 3 parts |
| Carplex #80 (anti-freezing agent) (white carbon, mfd. by Shionogi Pharmaceutical Co., Ltd.) | 2 parts |

The above substances are uniformly mixed and ground to formulate a wettable powder.

| Formulation Example 2: Emulsifiable concentrate | |
|---|---|
| Compound A-1 of the present invention | 3 parts |
| Xylene | 76 parts |
| Isophorone | 15 parts |
| Sorpol 3005 X (mixture of nonionic surfactant and anionic surfactant, mfd. by Toho Chemical Co., Ltd.) | 6 parts |

The above substances are uniformly mixed to prepare an emulsifiable concentrate.

| Formulation Example 3: Flowable | |
|---|---|
| Compound A-1 of the present invention | 35 parts |
| Agrizole S-711 (nonionic surfactant, mfd. by Kao Corporation) | 8 parts |
| Runox 1000 C (anionic surfactant, mfd. by Toho Chemical Co., Ltd.) | 0.5 parts |
| 1% Rodopol water (thickener, mfd. by Rhone-Poulenc) | 20 parts |
| Ethylene glycol (anti-freezing agent) | 8 parts |
| Water | 28.5 parts |

The above substances are uniformly mixed to formulate a flowable.

| Formulation Example 4: Granular wettable powder (dry flowable) | |
|---|---|
| Compound A-1 of the present invention | 75 parts |
| Isobam No. 1 (anionic surfactant, mfd. by Kuraray Isoprene Chemical Co., Ltd.) | 10 parts |
| Vanilex N (anionic surfactant, mfd. by Sanyo Kokusaku Pulp K.K.) | 5 parts |
| Carplex #80 (white carbon, mfd. by Shionogi Pharmaceutical Co., Ltd.) | 10 parts |

The above substances are uniformly mixed and pulverized to prepare a dry flowable.

| Formulation Example 5: Wettable powder | |
|---|---|
| Compound B-1 of the present invention | 50 parts |
| Zeeklite PFP (kaolin type clay, mfd. by Zeeklite Ind. Co., Ltd.) | 43 parts |
| Sorpol 5050 (anionic surfactant, mfd. by Toho Chemical Co., Ltd.) | 2 parts |
| Runox 1000 C (anionic surfactant, mfd. by Toho Chemical Co., Ltd.) | 3 parts |
| Carplex #80 (anti-freezing agent) (white carbon, mfd. by Shionogi Pharm. Co., Ltd.) | 2 parts | the above substances are uniformly mixed and ground to form a wettable powder.

| Formulation Example 6: Emulsifiable concentrate | |
|---|---|
| Compound B-1 of the present invention | 3 parts |
| Xylene | 76 parts |
| Isophorone | 15 parts |
| Sorpol 3005 X (mixture of nonionic surfactant and anionic surfactant, mfd. by Toho Chemical Co., Ltd.) | 6 parts |

The above substances are uniformly mixed to prepare an emulsifiable concentrate.

| Formulation Example 7: Flowable | |
|---|---|
| Compound B-1 of the present invention | 35 parts |
| Agrizole S-711 (nonionic surfactant, mfd. by Kao Corp.) | 8 parts |
| Runox 1000 C (anionic surfactant, mfd. by Toho Chemical Co., Ltd.) | 0.5 parts |
| 1% Rodopol water (thickener, mfd. by Rhone-Poulenc) | 20 parts |
| Ethylene glycol (anti-freezing agent) | 8 parts |
| Water | 28.5 parts |

The above substances are uniformly mixed to prepare a flowable.

| Formulation Example 8: Granules | |
|---|---|
| Compound B-1 of the present invention | 0.1 parts |
| Bentonite | 55.0 parts |
| Talc | 44.9 parts |

The above substances are uniformly mixed and ground, then kneaded with stirring by adding a small amount of water, granulated by an extrusion granulator and dried to form granules.

| Formulation Example 9: Granular wettable powder (dry flowable) | |
| --- | --- |
| Compound B-1 of the present invention | 75 parts |
| Isobam No. 1 (anionic surfactant, mfd. by Kuraray Isoprene Chemical Co., Ltd.) | 10 parts |
| Vanilex N (anionic surfactant, mfd. by Sanyo Kokusaku Pulp K.K.) | 5 parts |
| Carplex #80 (white carbon, mfd. by Shionogi Pharm. Co., Ltd.) | 10 parts |

The above substances are uniformly mixed and pulverized to obtain a dry flowable.

| Formulation Example 10: Wettable powder | |
| --- | --- |
| Compound C-1 of the present invention | 50 parts |
| Zeeklite PFP (kaolin type clay, mfd. by Zeeklite Industries Co., Ltd.) | 43 parts |
| Sorpol 5050 (anionic surfactant, mfd. by Toho Chemical Co., Ltd.) | 2 parts |
| Runox 1000 C (anionic surfactant, mfd. by Toho Chemical Co., Ltd.) | 3 parts |
| Carplex #80 (anti-freezing agent) (white carbon, mfg. by Shionogi Pharm. Co., Ltd.) | 2 parts |

The above substances are uniformly mixed and ground to form a wettable powder.

| Formulation Example 11: Emulsifiable concentrate | |
| --- | --- |
| Compound C-1 of the present invention | 3 parts |
| Xylene | 76 parts |
| Isophorone | 15 parts |
| Sorpol 3005 X (mixture of nonionic surfactant and anionic surfactant, mfd. by Toho Chemical Co., Ltd.) | 6 parts |

The above substances are uniformly mixed to prepare an emulsifiable concentrate.

| Formulation Example 12: Flowable | |
| --- | --- |
| Compound C-1 of the present invention | 35 parts |
| Agrizole S-711 (nonionic surfactant, mfd. by Kao Corporation) | 8 parts |
| Runox 1000 C (anionic surfactant, mfd. by Toho Chemical Co., Ltd.) | 0.5 parts |
| 1% Rodopol water (thickener, mfd. by Rhone-Poulenc) | 20 parts |
| Ethylene glycol (anti-freezing agent) | 8 parts |
| Water | 28.5 parts |

The above substances are uniformly mixed to prepare a flowable.

| Formulation Example 13: Granules | |
| --- | --- |
| Compound C-1 of the present invention | 0.1 parts |
| Bentonite | 55.0 parts |
| Talc | 44.9 parts |

The above substances are uniformly mixed and ground, then kneaded with stirring by adding a small amount of water, granulated by an extrusion granulator and dried to form granules.

| Formulation Example 14: Granular wettable powder (dry flowable) | |
| --- | --- |
| Compound C-1 of the present invention | 75 parts |
| Isobam No. 1 (anionic surfactant, mfd. by Kuraray Isoprene Chemical Co., Ltd.) | 10 parts |
| Vanilex N (anionic surfactant, mfd. by Sanyo Kokusaku Pulp K.K.) | 5 parts |
| Carplex #80 (white carbon, mfd. by Shionogi Pharm. Co., Ltd.) | 10 parts |

The above substances are uniformly mixed and pulverized to form a dry flowable.

In practical use of the above formulations, in the case of wettable powder, emulsifiable concentrate, flowable and granular wettable powder, they are diluted 50 to 1,000 times with water and then applied so that the active ingredient will be supplied at a rate of 0.0001 to 10 kg per hectare.

The utility of the compounds of the present invention as an active ingredient of herbicides will be clearly appreciated from the results of the test examples described below.

TEST EXAMPLE 1

Test on herbicidal effect by soil treatment

Sterilized diluvial soil was placed in a 15 cm×22 cm×6 cm plastic case. Then the seeds of barnyardgrass (*Echinochloa crus-galli*), crabgrass (*Dicitaria adscendens*), annual sedge (*Cyperus microiria*), black nightshade (*Solanum nigrum*), hairly galinsoga (*Galinsoga ciliate*), fieldcress (*Rorippa indica*), rice (*Oryza sativa*), corn (*Zea mays*), wheat (*Triticum aestivum*), soybean (*Glycine max*) and cotton (*Cossipium herbaceum*) were sown mixedly in the case and covered up about 1 cm with soil, and then a test liquid herbicide was sprayed uniformly over the soil surface by a small-sized sprayer so that the active ingredient would be supplied at the predetermined rate. Each test liquid herbicide was prepared by diluting with water a formulation prepared according to the relevant Formulation Examples described above. Three weeks after application (spraying) of the test liquid herbicide, its herbicidal effects on said various species of weeds and crops were examined and evaluated according to the following standard ratings. The results are shown in Tables 4-A,1, 4-A,2, 4-B, 4-C-1 and 4-C-2.

Standard ratings

5: Growth control rate is more than 90%. (Plants were almost completely withered.)
4: Growth control rate is 70-90%.
3: Growth control rate is 40-70%.
2: Growth control rate is 20-40%.
1: Growth control rate is less than 5%. (Almost non-effective.)

The growth control rate was determined from the following formula after measuring the above-ground plant portion weight in the treated area and that in the non. treated area:

Growth control rate =

$$\left( 1 - \frac{\text{above-ground plant portion weight in treated area}}{\text{above-ground plant portion weight in non-treated area}} \right) \times 100$$

TEST EXAMPLE 2

Test on herbicidal effect by foliage treatment

In a 15 cm×22 cm×6 cm plastic case containing sterilized diluvial soil, the seeds of barnyardgrass (*Echinochloa crus-galli*), crabgrass (*Digitaria adscendens*), annual sedge (*Cyperus microiria*), black nightshade (*Solanum nigrum*), hairly galinsoga (*Galinsoga ciliate*), fieldcress (*Rorippa indica*), rice (*Oryza sativa*), corn (*Zea mays*), wheat (*Triticum aestivum*), soybean (*Glycine max*), cotton (*Cossipium herbaceum*) and sugar beet (*Beta vulgaris*) were sown spotwise and covered up about 1 cm with soil. When the plants grew to the 2- to 3-foliate stage, the test liquid herbicide was uniformly sprayed to the foliage of the plants so that the active ingredient would be supplied at the predetermined rate.

Each test liquid herbicide was prepared by diluting with water a formulation prepared according to the relevant Formulation Examples described above, and was sprayed to the whole foliage of the weeds by a small-sized sprayer. Four weeks after spray of the test liquid herbicide, its herbicidal effects on said species of weeds and useful plants were examined and evaluated according to the same standard ratings as used in Test Example 1. The results are shown in Tables 5-A-1, 5-A-2, 5-B, 5-C-1 and 5-C-2.

TEST EXAMPLE 3

Test on herbicidal effect in irrigated field

Alluvial soil was placed in 1/5000 are Wagner pots, and then water was poured thereinto to knead the soil and to form the miniature simulations of paddy field with 2 cm deep water above the soil. Then the seeds of barnyardgrass (*Echinochloa crus-galli*), ducksalad (*Monochoria vaginalis*), toothcup (*Rotala indica*) and bullrush (*Scirpus juncoides*) were sown mixedly in said pots. Also, the tubes of perennial flat sedge (*Cyperus serotinus*) and arrowhead (*Sacittaria pygmaea*) were placed in the soil bed, and then the 2.5.foliate rice seedlings were transplanted. The pots were placed in a 25° to 30° C. greenhouse to allow normal growth of the plants. On the 2nd day after seeding, the diluted herbicide liquid to be tested was dropped onto the water surface in each pot with a measuring pipette so that the predetermined amount of compound would be supplied. Three weeks after application of the liquid herbicide, its herbicidal effects on rice and said species of weeds were examined and evaluated according to the same standard ratings as used in Test Example 1. The results are shown in Table 6.

The underlined symbols in the table represent the following:
N: barnyardgrass (*Echinochloa crus-galli*)
M: crabgrass (*Digitaria adscendens*)
K: annual sedge (*Cyperus microiria*)
H: black nightshade (*Solanum nigrum*)
D: hairly galinsoga (*Galinsoga ciliate*)
I: fieldcress (*Rorippa indica*)
R: rice (*Oryza sativa*)
T: corn (*Zea mays*)
W: wheat (*Triticum aestivum*)
S: soybean (*Glycine max*)
C: cotton (*Cossipium herbaceum*)
B: sugar beet (*Beta vulgaris*)

Bromacil having the following structure was used as control compound:

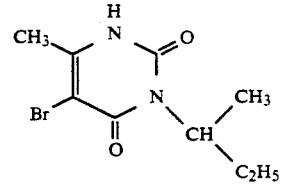

TABLE 4-A-1

| Compound No. | Application amount (g/ha) | N | M | K | H | D | I |
|---|---|---|---|---|---|---|---|
| A-1 | 10 | 5 | 5 | 5 | 5 | 5 | 5 |
|  | 20 | 5 | 5 | 5 | 5 | 5 | 5 |
|  | 40 | 5 | 5 | 5 | 5 | 5 | 5 |

TABLE 4-A-2

| Compound No. | Application amount (g/ha) | N | M | K | H | D | I | R | T | W | S | C |
|---|---|---|---|---|---|---|---|---|---|---|---|---|
| A-3 | 10 | 5 | 5 | 5 | 5 | 5 | 5 | 2 | 1 | 1 | 0 | 1 |
|  | 20 | 5 | 5 | 5 | 5 | 5 | 5 | 4 | 3 | 2 | 0 | 2 |
|  | 40 | 5 | 5 | 5 | 5 | 5 | 5 | 5 | 5 | 0 | 4 |
| A-4 | 10 | 5 | 5 | 5 | 5 | 5 | 5 | 0 | 1 | 0 | 2 | 2 |
|  | 20 | 5 | 5 | 5 | 5 | 5 | 5 | 1 | 2 | 1 | 3 | 3 |
|  | 40 | 5 | 5 | 5 | 5 | 5 | 5 | 3 | 4 | 3 | 4 | 4 |
| A-6 | 10 | 5 | 5 | 5 | 5 | 5 | 5 | 3 | 3 | 1 | 1 | 1 |
|  | 20 | 5 | 5 | 5 | 5 | 5 | 5 | 4 | 4 | 2 | 2 | 2 |
|  | 40 | 5 | 5 | 5 | 5 | 5 | 5 | 5 | 5 | 4 | 3 | 4 |
| A-8 | 40 | 3 | 5 | 5 | 5 | 5 | 5 | 1 | 0 | 0 | 0 | 0 |
|  | 80 | 4 | 5 | 5 | 5 | 5 | 5 | 2 | 1 | 1 | 0 | 0 |
|  | 160 | 5 | 5 | 5 | 5 | 5 | 5 | 3 | 3 | 2 | 1 | 2 |
| A-10 | 40 | 2 | 2 | 4 | 5 | 2 | 5 | 0 | 1 | 0 | 0 | 0 |
|  | 80 | 3 | 4 | 5 | 5 | 4 | 5 | 1 | 2 | 1 | 1 | 1 |
|  | 160 | 3 | 5 | 5 | 5 | 5 | 5 | 2 | 4 | 3 | 2 | 4 |
| A-12 | 10 | 3 | 3 | 5 | 5 | 4 | 5 | 3 | 3 | 2 | 0 | 1 |
|  | 20 | 4 | 4 | 5 | 5 | 5 | 5 | 4 | 4 | 3 | 1 | 2 |
|  | 40 | 5 | 5 | 5 | 5 | 5 | 5 | 5 | 4 | 2 | 4 |
| A-14 | 10 | 5 | 5 | 5 | 5 | 5 | 5 | 5 | 5 | 2 | 4 |
|  | 20 | 5 | 5 | 5 | 5 | 5 | 5 | 5 | 5 | 3 | 5 |
|  | 40 | 5 | 5 | 5 | 5 | 5 | 5 | 5 | 5 | 4 | 5 |
| A-16 | 10 | 5 | 5 | 5 | 5 | 5 | 5 | 5 | 5 | 2 | 5 |
|  | 20 | 5 | 5 | 5 | 5 | 5 | 5 | 5 | 5 | 3 | 5 |
|  | 40 | 5 | 5 | 5 | 5 | 5 | 5 | 5 | 5 | 4 | 5 |
| A-20 | 10 | 5 | 5 | 5 | 5 | 5 | 5 | 2 | 3 | 2 | 1 | 2 |
|  | 20 | 5 | 5 | 5 | 5 | 5 | 5 | 3 | 4 | 3 | 2 | 3 |
|  | 40 | 5 | 5 | 5 | 5 | 5 | 5 | 4 | 5 | 4 | 3 | 4 |
| A-22 | 10 | 5 | 5 | 5 | 5 | 5 | 5 | 3 | 5 | 5 | 0 | 3 |
|  | 20 | 5 | 5 | 5 | 5 | 5 | 5 | 4 | 5 | 5 | 1 | 4 |
|  | 40 | 5 | 5 | 5 | 5 | 5 | 5 | 5 | 5 | 3 | 5 |
| A-32 | 10 | 5 | 5 | 3 | 5 | 5 | 5 | 2 | 4 | 1 | 0 | 2 |
|  | 20 | 5 | 5 | 4 | 5 | 5 | 5 | 3 | 5 | 2 | 1 | 4 |
|  | 40 | 5 | 5 | 5 | 5 | 5 | 5 | 4 | 5 | 2 | 5 |

TABLE 4-B

| Compound No. | Application amount (g/ha) | N | M | K | H | D | I | R | T | W | S | C | B |
|---|---|---|---|---|---|---|---|---|---|---|---|---|---|
| B-1 | 10 | 5 | 5 | 5 | 5 | 5 | 5 | 0 | 0 | 0 | 0 | 2 | 4 |
|  | 20 | 5 | 5 | 5 | 5 | 5 | 5 | 1 | 1 | 0 | 0 | 3 | 5 |
|  | 40 | 5 | 5 | 5 | 5 | 5 | 5 | 2 | 2 | 1 | 1 | 4 | 5 |

TABLE 4-C-1

| Compound No. | Application amount (g/ha) | N | M | K | H | D | I |
|---|---|---|---|---|---|---|---|
| C-1 | 10 | 4 | 4 | 5 | 5 | 5 | 5 |
|  | 20 | 5 | 5 | 5 | 5 | 5 | 5 |
|  | 40 | 5 | 5 | 5 | 5 | 5 | 5 |
| Comparative compound | 40 | 2 | 0 | 2 | 4 | 5 | 4 |

TABLE 4-C-2

| Compound No. | Application amount (g/ha) | N | M | K | H | D | I | R | T | W | S | C |
|---|---|---|---|---|---|---|---|---|---|---|---|---|
| C-3 | 10 | 5 | 5 | 5 | 5 | 5 | 5 | 0 | 1 | 0 | 0 | 0 |
|  | 20 | 5 | 5 | 5 | 5 | 5 | 5 | 0 | 2 | 1 | 0 | 0 |
|  | 40 | 5 | 5 | 5 | 5 | 5 | 5 | 1 | 3 | 2 | 0 | 0 |

TABLE 5-A-1

| Compound No. | Application amount (g/ha) | N | M | K | H | D | I |
|---|---|---|---|---|---|---|---|
| A-1 | 10 | 5 | 5 | 5 | 5 | 5 | 5 |
|  | 20 | 5 | 5 | 5 | 5 | 5 | 5 |
|  | 40 | 5 | 5 | 5 | 5 | 5 | 5 |

TABLE 5-A-2

| Compound No. | Application amount (g/ha) | N M K H D I R T W S C B |
|---|---|---|
| A-3 | 10 | 5 3 5 5 5 5 4 4 2 4 4 5 |
|  | 20 | 5 4 5 5 5 5 5 5 4 5 5 5 |
|  | 40 | 5 5 5 5 5 5 5 5 5 5 5 5 |
| A-4 | 10 | 3 4 5 5 5 5 4 2 2 5 5 5 |
|  | 20 | 4 5 5 5 5 5 5 3 3 5 5 5 |
|  | 40 | 5 5 5 5 5 5 5 4 4 5 5 5 |
| A-6 | 10 | 2 2 5 5 5 5 3 2 2 4 5 5 |
|  | 20 | 4 4 5 5 5 5 4 3 2 5 5 5 |
|  | 40 | 5 5 5 5 5 5 5 4 3 5 5 5 |
| A-8 | 40 | 0 2 5 5 5 5 0 1 0 2 1 1 |
|  | 80 | 1 2 5 5 5 5 0 2 1 2 2 2 |
|  | 160 | 2 3 5 5 5 5 1 3 2 3 3 2 |
| A-10 | 40 | 2 1 5 5 3 2 1 1 2 2 5 2 |
|  | 80 | 3 2 5 5 4 4 2 2 3 3 5 3 |
|  | 160 | 5 3 5 5 5 4 4 4 4 4 5 3 |
| A-12 | 10 | 4 3 5 5 5 5 2 3 2 3 5 4 |
|  | 20 | 5 4 5 5 5 5 3 4 3 4 5 5 |
|  | 40 | 5 5 5 5 5 5 4 5 4 5 5 5 |
| A-14 | 10 | 5 5 5 5 5 5 5 5 5 5 5 5 |
|  | 20 | 5 5 5 5 5 5 5 5 5 5 5 5 |
|  | 40 | 5 5 5 5 5 5 5 5 5 5 5 5 |
| A-16 | 10 | 5 5 5 5 5 5 5 5 5 5 5 5 |
|  | 20 | 5 5 5 5 5 5 5 5 5 5 5 5 |
|  | 40 | 5 5 5 5 5 5 5 5 5 5 5 5 |
| A-20 | 10 | 3 2 3 5 5 4 4 3 3 3 5 3 |
|  | 20 | 4 3 4 5 5 5 5 4 4 4 5 4 |
|  | 40 | 5 4 5 5 5 5 5 5 5 5 5 5 |
| A-22 | 10 | 3 3 3 5 5 4 5 4 5 5 5 3 |
|  | 20 | 4 4 4 5 5 5 5 5 5 5 5 4 |
|  | 40 | 5 5 5 5 5 5 5 5 5 5 5 5 |
| A-32 | 10 | 3 3 5 5 5 5 4 4 5 5 5 4 |
|  | 20 | 4 4 5 5 5 5 5 5 5 5 5 5 |
|  | 40 | 5 5 5 5 5 5 5 5 5 5 5 5 |

TABLE 5-B

| Compound No. | Application amount (g/ha) | N | M | K | H | D | I | R | T | W | S | C | B |
|---|---|---|---|---|---|---|---|---|---|---|---|---|---|
| B-1 | 10 | 5 | 5 | 5 | 5 | 5 | 5 | 2 | 1 | 0 | 1 | 5 | 5 |
|  | 20 | 5 | 5 | 5 | 5 | 5 | 5 | 3 | 2 | 1 | 2 | 5 | 5 |
|  | 40 | 5 | 5 | 5 | 5 | 5 | 5 | 4 | 3 | 2 | 3 | 5 | 5 |

TABLE 5-C-1

| Compound No. | Application amount (g/ha) | N | M | K | H | D | I |
|---|---|---|---|---|---|---|---|
| C-1 | 10 | 4 | 5 | 5 | 5 | 5 | 5 |
|  | 20 | 5 | 5 | 5 | 5 | 5 | 5 |
|  | 40 | 5 | 5 | 5 | 5 | 5 | 5 |
| Comparative compound | 40 | 0 | 0 | 1 | 4 | 2 | 3 |

TABLE 5-C-2

| Compound No. | Application amount (g/ha) | N M K H D I R T W S C B |
|---|---|---|
| C-3 | 10 | 2 1 5 5 5 5 0 2 0 5 5 5 |
|  | 20 | 4 2 5 5 5 5 1 3 1 5 5 5 |
|  | 40 | 5 3 5 5 5 5 3 3 2 5 5 5 |

TABLE 6

| Compound No. | Application amount (g/ha) | Barnyard-grass | Bulrush | Ducksalad | Toothcup | Permnial flat sedge | Asro whead | Transplanted rice |
|---|---|---|---|---|---|---|---|---|
| A-1 | 2 | 4 | 4 | 5 | 5 | 5 | 5 | 0 |
|  | 4 | 5 | 5 | 5 | 5 | 5 | 5 | 0 |
|  | 8 | 5 | 5 | 5 | 5 | 5 | 5 | 0 |
| C-3 | 5 | 5 | 4 | 5 | 5 | 2 | 4 | 0 |
|  | 10 | 5 | 5 | 5 | 5 | 3 | 5 | 0 |
|  | 20 | 5 | 5 | 5 | 5 | 4 | 5 | 0 |

What is claimed is:

1. An uracil derivatives represented by the formula (I):

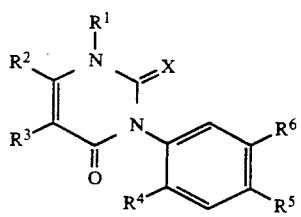 (I)

wherein
$R^1$ represents hydrogen, $C_{1-3}$ alkyl, hydroxymethyl or $C_{1-3}$ haloalkyl,
$R^2$ represents $C_{1-6}$ haloalkyl,
$R^3$ represents hydrogen, $C_{1-6}$ alkyl, $C_{1-6}$ haloalkyl, hydroxymethyl, halogen or nitro,
$R^4$ represents hydrogen or halogen,
$R^5$ represents halogen, nitro or cyano,
$R^6$ represents $-S-B^1$ [wherein $B^1$ represents hydrogen, $C_{1-5}$ alkyl, $C_{3-6}$ cycloalkyl, $C_{2-4}$ alkenyl, $C_{3-4}$ alkynyl, cyanomethyl, hydroxymethyl, chloromethyl, benzyl,

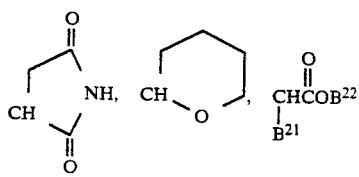

[in which $B^{21}$ represents hydrogen, $C_{1-3}$ alkyl, methylthio, phenylthio or methoxymethyl, and $B^{22}$ represents hydrogen, sodium, potassium, ammonium, isopropylammonium, $C_{1-5}$ alkyl, $C_{2-5}$ alkenyl, $C_{3-5}$ alkynyl, $C_{3-6}$ cycloalkyl, $C_{3-6}$ cycloalkyl-$C_{1-2}$ alkyl, $C_{2-3}$ haloalkyl, phenethyl,α-methylbenzyl, 3-dimethylaminopropyl, phenyl which may be substituted with one or more substituent (the substituent is at least one of halogen, $C_{1-4}$ alkyl, $C_{1-3}$ alkoxyl, $C_{1-2}$ alkylamino, dimethylamino, $C_{1-2}$ alkoxycarbonyl, $C_{2-3}$ acyl, $C_{1-2}$ haloalkyl or $C_{1-2}$ haloalkyloxyl) or benzyl which may be substituted with one or more substituent (the substituent is at least one of halogen, $C_{1-4}$ alkyl, $C_{1-3}$ alkoxyl, $C_{1-2}$ alkylamino, dimethylamino, $C_{2-3}$ acyl, trifluoroacetylamino, $C_{1-2}$ alkoxy-carbonyl, methylsulfonyl, trifluoromethyl-sulfonyl, $C_{1-2}$ haloalkyl or $C_{1-2}$ haloalkyloxyl)], $CH_2\text{-}(CH_2\text{-})_n CO_2B^{22}$ (wherein $B^{22}$ is the same meaning as defined above, and n is an integer of 1 to 4), $CH_2-Y-B^{23}$ (wherein $B^{23}$ is hydrogen, $C_{1-5}$ alkyl, cyanomethyl, $C_{2-5}$ acyl, chloroacetyl or dimethylcarbamoyl, and Y is oxygen or sulfur), $CH_2-Y-CH(B^{21})CO_2B^{22}$ (wherein $B^{21}$, $B^{22}$ and Y are the same meanings as defined above), or $CH_2-Y-CH_2\text{-}(CH_2\text{-})_n CO_2B^{22}$ (wherein $B^{22}$, n and Y are the same meanings as defined above)];

[wherein $D^{21}$ represents hydrogen, $C_{1-3}$ alkyl, $C_{1-3}$ alkoxyl or $C_{1-3}$ alkoxy-$C_{1-2}$ alkyl, and $D^{22}$ represents hydrogen, $C_{1-4}$ alkyl, $C_{3-6}$ cycloalkyl, $C_{2-3}$ haloalkyl, phenyl or benzyl];

[Wherein $D^{21}$ and $D^{22}$ are the same meanings as defined above, and $D^{23}$ represents hydrogen or $C_{1-3}$ alkyl];

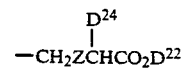

[wherein $D^{22}$ is the same meaning as defined above, $D^{24}$ represents hydrogen, $C_{1-3}$ alkyl or $C_{1-3}$ alkoxy-$C_{1-2}$ alkyl, and Z represents oxygen, sulfur or NH];

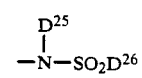

[Wherein $D^{25}$ represents hydrogen, sodium, $C_{1-4}$ alkyl, $C_{2-5}$ alkenyl, $C_{3-5}$ alkynyl, $C_{2-5}$ acyl, $C_{1-4}$ alkylsulfonyl or $C_{1-3}$ alkoxy-$C_{1-2}$ alkyl, and $D^{26}$ represents $C_{1-4}$ alkyl or $C_{1-3}$ haloalkyl];

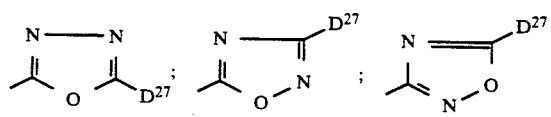

[wherein $D^{27}$ represents hydrogen, $C_{1-6}$ alkyl, $C_{3-6}$ cycloalkyl, $C_{1-3}$ haloalkyl, $C_{1-4}$ alkoxyl, $C_{1-4}$ alkylthio, $C_{1-4}$ alkoxy-carbonyl, mercapto, hydroxyl, $C_{1-3}$ alkoxy-$C_{1-2}$ alkyl, $C_{1-4}$ alkylamino, $ND^{28}(D^{29})$ (wherein $D^{28}$ and $D^{29}$ represent independently $C_{1-4}$ alkyl), dimethylcarbamoyl, $CONHSO_2CH_3$, $C_{1-4}$ alkylsulfonyl, or $N(D^{30})SO_2D^{31}$ (wherein $D^{30}$ represents hydrogen, sodium, $C_{1-4}$ alkyl, $C_{1-4}$ alkylsulfonyl, $C_{1-3}$ alkoxy-$C_{1-2}$ alkyl, and $D^{31}$ represents $C_{1-4}$ alkyl or $C_{1-3}$ haloalkyl)];

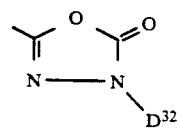

[wherein $D^{32}$ represents $C_{1-6}$ alkyl or $C_{3-6}$ cycloalkyl];

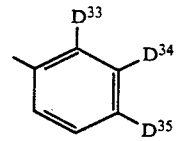

[wherein $D^{33}$, $D^{34}$ and $D^{35}$ represent independently hydrogen or $C_{1-6}$ alkyl];

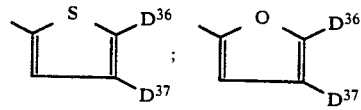

[wherein $D^{36}$ and $D^{37}$ represent independently hydrogen, $C_{1-6}$ alkyl or dimethylamino];

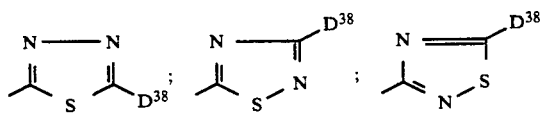

[wherein $D^{38}$ represents hydrogen, halogen, mercapto, hydroxyl, $C_{1-6}$ alkyl, $C_{3-6}$ cycloalkyl, $C_{1-3}$ haloalkyl, $C_{1-4}$ alkoxyl, $C_{1-4}$ alkylthio, $C_{1-4}$ alkoxycarbonyl, dimethylcarbamoyl, $C_{1-3}$ alkoxy-$C_{1-2}$ alkyl, $C_{1-4}$ alkylsulfonyl, phenyl, benzyl or $N(D^{39})SO_2D^{31}$ (wherein $D^{31}$ is the same meaning as defined above, and $D^{39}$ represents hydrogen, $C_{1-4}$ alkyl, sodium, potassium, $C_{1-4}$ alkylsulfonyl or $C_{1-3}$ alkoxy-$C_{1-2}$ alkyl)];

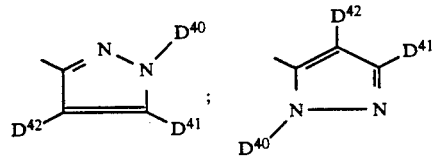

[wherein $D^{40}$ represents hydrogen, $C_{1-6}$ alkyl, $C_{3-6}$ cycloalkyl, phenyl, benzyl or 2-pyridyl, $D^{41}$ represents hydrogen, halogen, mercapto, hydroxyl, amino, $C_{1-6}$ alkyl, $C_{1-4}$ alkylamino, $ND^{28}(D^{29})$ (wherein $D^{28}$ and $D^{29}$ are the same meanings as defined above), $C_{1-4}$ alkylthio, $CO_2D^{28}$ (wherein $D^{28}$ is the same meaning as defined above), $C_{1-4}$ alkylsulfonyl, $C_{1-4}$ alkoxyl or $N(D^{39})SO_2D^{31}$ (wherein $D^{31}$ and $D^{39}$ are the same meanings as defined above), and $D^{42}$ represents hydrogen, halogen, nitro, amino, cyano, $C_{1-4}$ alkylamino, $N(D^{28})D^{29}$ (wherein $D^{28}$ and $D^{29}$ are the same meanings as defined above), $C_{1-4}$ alkylcarbonyl or $C_{1-4}$ alkoxy-carbonyl];

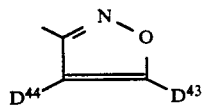

[wherein $D^{43}$ represents hydrogen, hydroxyl, methoxy, amino, benzoyl or $C_{1-4}$ alkyl, and $D^{44}$ represents hydrogen, cyano, acetyl, $C_{1-4}$ alkyl, carboxyl or $C_{1-4}$ alkoxy-carbonyl];

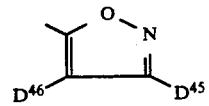

[wherein $D^{45}$ and $D^{46}$ represent independently hydrogen, phenyl, hydroxyl, methoxy or $C_{1-4}$ alkyl]; or

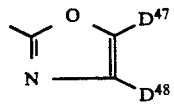

[wherein $D^{47}$ and $D^{48}$ represent independently hydrogen or $C_{1-4}$ alkyl], and X represents oxygen or sulfur.

2. An uracil derivative according to claim 1, wherein said uracil derivative is represented by the formula III:

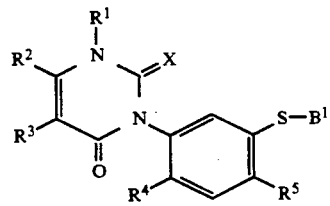

wherein
$R^1$ represents hydrogen, $C_{1-3}$ alkyl, hydroxymethyl or halomethyl,
$R^2$ represents $C_{1-6}$ haloalkyl,
$R^3$ represents hydrogen, $C_{1-6}$ alkyl, $C_{1-6}$ haloalkyl, hydroxymethyl, halogen or nitro,
$R^4$ represents hydrogen or halogen,
$R^5$ represents halogen, nitro or cyano,
$B^1$ represents hydrogen, $C_{1-5}$ alkyl, $C_{3-6}$ cycloalkyl, $C_{2-4}$ alkenyl, $C_{3-4}$ alkynyl, cyanomethyl, hydroxymethyl, chloromethyl, benzyl,

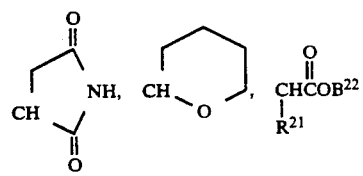

[wherein $B^{21}$ represents hydrogen, $C_{1-3}$ alkyl, methylthio, phenylthio or methoxymethyl, and $B^{22}$ represents hydrogen, sodium, potassium, ammonium, isopropylammonium, $C_{1-5}$ alkyl, $C_{2-5}$ alkenyl, $C_{3-5}$ alkynyl, $C_{3-6}$ cycloalkyl, $C_{3-6}$ cycloalkyl-$C_{1-2}$ alkyl, $C_{2-3}$ haloalkyl, phenethyl, α-methylbenzyl, 3-dimethylaminopropyl, phenyl which may be substituted with one or more substituent (the substituent is at least one of halogen, $C_{1-4}$ alkyl, $C_{1-3}$ alkoxyl, $C_{1-2}$ alkylamino, dimethylamino, $C_{1-2}$ alkoxy-carbonyl, $C_{2-3}$ acyl, $C_{1-2}$ haloalkyl or $C_{1-2}$ haloalkyloxyl), or benzyl which may be substituted with one or more substituent (the substituent is at least one of halogen, $C_{1-4}$ alkyl, $C_{1-3}$ alkoxyl, $C_{1-2}$ alkylamino, dimethylamino, $C_{2-3}$ acyl, trifluoroacetylamino, $C_{1-2}$ alkoxy-carbonyl, methylsulfonyl, trifluoro-methylsulfonyl, $C_{1-2}$ haloalkyl or $C_{1-2}$ haloalkyloxyl)], $CH_2\text{-}(CH_2)_n\text{-}CO_2B^{22}$ [wherein $B^{22}$ is the same meaning as defined above, and n is an integer of 1 to 4], $CH_2\text{-}Y\text{-}B^{23}$ [wherein $B^{23}$ represents hydrogen, $C_{1-5}$ alkyl, cyanomethyl, $C_{2-5}$ acyl, chloroacetyl or dimethylcarbamoyl, and Y is oxygen or sulfur], $CH_2\text{-}Y\text{-}CH(B^{21})CO_2B^{22}$ [wherein $B^{21}$, $B^{22}$ and Y are the same meanings as defined above] or $CH_2\text{-}Y\text{-}CH_2\text{-}(CH_2)_n\text{-}CO_2B^{22}$ [wherein $B^{22}$, n and Y are the same meanings as defined above], and X represents oxygen or sulfur.

3. An uracil derivative according to claim 13, wherein said uracil derivative is represented by the formula IV:

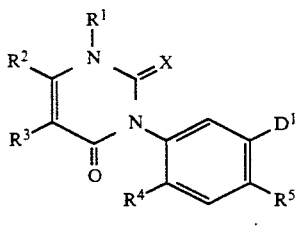
(IV)

wherein
$R^1$ represents hydrogen, $C_{1-3}$ alkyl or $C_{1-3}$ haloalkyl,
$R^2$ represents $C_{1-6}$ haloalkyl,
$R^3$ represents hydrogen, $C_{1-6}$ alkyl, $C_{1-6}$ haloalkyl, hydroxymethyl, halogen or nitro,
$R^4$ represents hydrogen or halogen,
$R^5$ represents halogen, nitro or cyano,
$D^1$ represents

[wherein $D^{21}$ represents hydrogen, $C_{1-3}$ alkyl, $C_{1-3}$ alkoxyl or $C_{1-3}$ alkoxy-$C_{1-2}$ alkyl, and $D^{22}$ represents hydrogen, $C_{1-4}$ alkyl, $C_{3-6}$ cycloalkyl, $C_{2-3}$ haloalkyl, phenyl or benzyl],

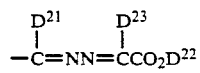

[wherein $D^{21}$ and $D^{22}$ are the same meanings as defined above, and $D^{23}$ represents hydrogen or $C_{1-3}$ alkyl],

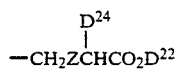

[wherein $D^{22}$ is the same meaning as defined above, and $D^{24}$ represents hydrogen, $C_{1-3}$ alkyl or $C_{1-3}$ alkoxy-$C_{1-2}$ alkyl, and Z represents oxygen, sulfur or NH],

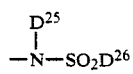

[wherein $D^{25}$ represents hydrogen, sodium, $C_{1-4}$ alkyl, $C_{2-5}$ alkenyl, $C_{3-5}$ alkynyl, $C_{2-5}$ acyl, $C_{1-4}$ alkylsulfonyl or $C_{1-3}$ alkoxy-$C_{1-2}$ alkyl, and $D^{26}$ represents $C_{1-4}$ alkyl or $C_{1-3}$ haloalkyl],

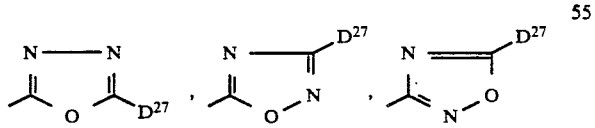

[wherein $D^{27}$ represents hydrogen, $C_{1-6}$ alkyl, $C_{3-6}$ cycloalkyl, $C_{1-3}$ haloalkyl, $C_{1-4}$ alkoxyl, $C_{1-4}$ alkylthio, $C_{1-4}$ alkoxy-carbonyl, mercapto, hydroxyl, $C_{1-3}$ alkoxy-$C_{1-2}$ alkyl, $C_{1-4}$ alkylamino, $ND^{28}(D^{29})$ (wherein $D^{28}$ and $D^{29}$ represent each independently $C_{1-4}$ alkyl), dimethylcarbamoyl, $CONHSO_2CH_3$, $C_{1-4}$ alkylsulfonyl or $N(D^{30})SO_2D^{31}$ (wherein $D^{30}$ represents hydrogen, sodium, $C_{1-4}$ alkyl, $C_{1-4}$ alkylsulfonyl or $C_{1-3}$ alkoxy-$C_{1-2}$ alkyl, and $D^{31}$ represents $C_{1-4}$ alkyl or $C_{1-3}$ haloalkyl)],

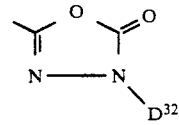

[wherein $D^{32}$ represents $C_{1-6}$ alkyl or $C_{3-6}$ cycloalkyl],

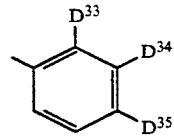

[wherein $D^{33}$, $D^{34}$ and $D^{35}$ represent each independently hydrogen or $C_{1-6}$ alkyl],

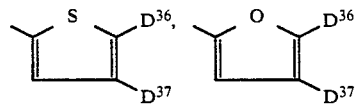

[wherein $D^{36}$ and $D^{37}$ represent each independently hydrogen, $C_{1-6}$ alkyl or dimethylamino],

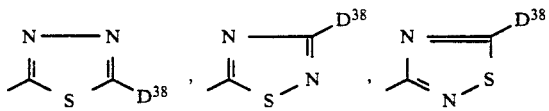

[wherein $D^{28}$ represents hydrogen, halogen, mercapto, hydroxyl, $C_{1-6}$ alkyl, $C_{3-6}$ cycloalkyl, $C_{1-3}$ haloalkyl, $C_{1-4}$ alkoxyl, $C_{1-4}$ alkylthio, $C_{1-4}$ alkoxycarbonyl, dimethylcarbamoyl, $C_{1-3}$ alkoxy-$C_{1-2}$ alkyl, $C_{1-4}$ alkylamino, $ND^{29}(D^{29})$ (wherein $D^{28}$ and $D^{29}$ are the same meanings as defined above), $CONHSO_2CH_3$, $C_{1-4}$ alkylsulfonyl, phenyl, benzyl or $N(D^{39})SO_2D^{31}$ (wherein $D^{31}$ is the same meaning as defined above, and $D^{39}$ represents hydrogen, $C_{1-4}$ alkyl, sodium, potassium, $C_{1-4}$ alkylsulfonyl or $C_{1-3}$ alkoxy-$C_{1-2}$ alkyl],

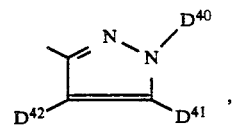

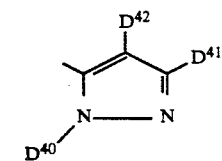

[wherein $D^{40}$ represents hydrogen, $C_{1-6}$ alkyl, $C_{3-6}$ cycloalkyl, phenyl, benzyl or 2-pyridyl, $D^{41}$ represents hydrogen, halogen, mercapto, hydroxyl, amino, $C_{1-6}$ alkyl, $C_{1-4}$ alkylamino, $ND^{28}(D^{29})$ (wherein $D^{28}$ and $D^{29}$ are the same meanings as given above), $D_{1-4}$ alkylthio, $CO_2D^{28}$ (wherein $D^{28}$ is the same meaning as defined above), $C_{1-4}$ alkylsulfonyl, $C_{1-4}$ alkoxyl or $N(D^{39})SO_2D^{31}$ (wherein $D^{31}$ and $D^{39}$ are the same meanings as defined above), and $D^{42}$ represents hydrogen, halogen, nitro, amino, cyano, $C_{1-4}$ alkylamino, $N(D^{28})D^{29}$ (wherein $D^{28}$ and $D^{29}$ are the same meanings as given above), $C_{1-4}$ alkylcarbonyl or $C_{1-4}$ alkoxycarbonyl],

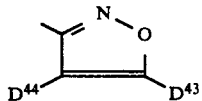

[wherein $D^{43}$ represents hydrogen, hydroxyl, methoxy, amino, benzoyl or $C_{1-4}$ alkyl, and $D^{44}$ represents hydrogen, cyano, acetyl, $C_{1-4}$ alkyl, carboxyl or $C_{1-4}$ alkoxy-carbonyl],

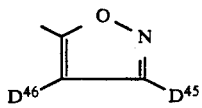

[wherein $D^{45}$ and $D^{46}$ represent each independently hydrogen, phenyl, hydroxyl, methoxy or $C_{1-4}$ alkyl], or

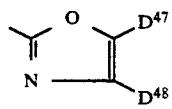

[wherein $D^{47}$ and $D^{48}$ represent each independently hydrogen or $C_{1-4}$ alkyl), and X represents oxygen or sulfur.

4. A herbicidal composition comprising a herbicidally effective amount of an uracil derivative as claimed in claim 1 and a herbicidally acceptable carrier or diluent therefor.

5. A herbicidal composition according to claim 16 wherein said uracil derivative is a compound as claimed in claim 2.

6. A herbicidal composition according to claim 16 wherein said uracil derivative is a compound as claimed in claim 3.

7. A method for killing weeds or inhibiting growth of weeds, comprising applying a herbicidally effective amount of an uracil derivative as claimed in claim 1.

8. A method according to claim 7 wherein said uracil derivative is a compound as claimed in claim 14.

9. A method according to claim 7 wherein said uracil derivative is a compound as claimed in claim 15.

* * * * *

UNITED STATES PATENT AND TRADEMARK OFFICE
CERTIFICATE OF CORRECTION

PATENT NO. : 5,127,935

DATED : JULY 7, 1992

INVENTOR(S) : JUN SATOW ET AL

It is certified that error appears in the above-identified patent and that said Letters Patent is hereby corrected as shown below:

On title page,

Item [30], under "Foreign Application Priority Data", delete "1-168688" and insert --2-168683.

Signed and Sealed this

Twenty-fourth Day of August, 1993

Attest:

BRUCE LEHMAN

Attesting Officer   Commissioner of Patents and Trademarks